US010183986B2

(12) United States Patent
Chou et al.

(10) Patent No.: US 10,183,986 B2
(45) Date of Patent: Jan. 22, 2019

(54) TRIMERIC COLLAGEN SCAFFOLD ANTIBODIES

(75) Inventors: Min-Yuan Chou, Taipei County (TW); Chia-Yu Fan, Hsinchu (TW); Chuan-Chuan Huang, Taipei County (TW); Hsiu-Chuan Li, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 2505 days.

(21) Appl. No.: 11/987,498

(22) Filed: Nov. 30, 2007

(65) Prior Publication Data

US 2008/0176247 A1 Jul. 24, 2008

Related U.S. Application Data

(63) Continuation-in-part of application No. 11/609,410, filed on Dec. 12, 2006, now abandoned.

(60) Provisional application No. 60/750,746, filed on Dec. 15, 2005.

(51) Int. Cl.

| | |
|---|---|
| ***C07K 16/00*** | (2006.01) |
| ***G01N 33/53*** | (2006.01) |
| ***C07H 21/04*** | (2006.01) |
| ***C07K 14/78*** | (2006.01) |
| ***C07K 16/24*** | (2006.01) |
| ***C07K 16/28*** | (2006.01) |
| ***C07K 16/32*** | (2006.01) |

(52) U.S. Cl.

CPC ............ *C07K 14/78* (2013.01); *C07K 16/241* (2013.01); *C07K 16/2809* (2013.01); *C07K 16/2863* (2013.01); *C07K 16/32* (2013.01); *C07K 2317/31* (2013.01); *C07K 2317/622* (2013.01); *C07K 2317/626* (2013.01); *C07K 2317/73* (2013.01); *C07K 2317/74* (2013.01); *C07K 2317/76* (2013.01); *C07K 2317/92* (2013.01); *C07K 2318/10* (2013.01); *C07K 2318/20* (2013.01); *C07K 2319/00* (2013.01); *C07K 2319/33* (2013.01); *C07K 2319/70* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 5,208,020 | A | 5/1993 | Chari et al. |
| 5,223,409 | A | 6/1993 | Ladner et al. |
| 5,475,092 | A | 12/1995 | Chari et al. |
| 5,585,089 | A | 12/1996 | Queen et al. |
| 5,585,499 | A | 12/1996 | Chari et al. |
| 5,693,761 | A | 12/1997 | Queen et al. |
| 5,693,762 | A | 12/1997 | Queen et al. |
| 5,846,545 | A | 12/1998 | Chari et al. |
| 6,187,907 | B1 | 2/2001 | Chen et al. |
| 6,190,886 | B1 | 2/2001 | Hoppe et al. |
| 6,232,107 | B1 | 5/2001 | Bryan et al. |
| 6,235,883 | B1 | 5/2001 | Jakobovits |
| 6,277,600 | B1 | 8/2001 | Tomita et al. |
| 7,268,116 | B2 | 9/2007 | Liang |
| 7,279,329 | B2 | 10/2007 | Chou et al. |
| 2004/0197876 | A1 | 10/2004 | Tschopp et al. |
| 2005/0172342 | A1 | 8/2005 | Karatzas et al. |
| 2005/0196830 | A1 | 9/2005 | Gruskin et al. |
| 2005/0202537 | A1 | 9/2005 | Liang |
| 2007/0087413 | A1 | 4/2007 | Liang |
| 2007/0117755 | A1 | 5/2007 | Liang |
| 2007/0264687 | A1 | 11/2007 | Chou et al. |
| 2009/0299034 | A1* | 12/2009 | Cejas et al. .................. 530/324 |
| 2010/0062977 | A1* | 3/2010 | Serra et al. ..................... 514/12 |

FOREIGN PATENT DOCUMENTS

| | | | |
|---|---|---|---|
| EP | 0 125 023 | A1 | 11/1984 |
| EP | 0 173 494 | A2 | 3/1986 |
| EP | 0 184 187 | A2 | 6/1986 |
| EP | 0 519 596 | A1 | 12/1992 |
| EP | 0 171 496 | B1 | 5/1993 |
| EP | 1 293 514 | A1 | 3/2003 |
| EP | 1 454 917 | A2 | 9/2004 |
| EP | 1 798 240 | A1 | 6/2007 |
| JP | 10-500298 | A | 1/1998 |
| JP | 2000-125872 | A | 5/2000 |
| JP | 2004-242638 | A | 9/2004 |
| JP | 2005-508628 | T | 4/2005 |
| JP | 2007-181458 | A | 7/2007 |
| WO | WO 87/02671 | A1 | 5/1987 |
| WO | WO 90/02809 | A1 | 3/1990 |
| WO | WO 91/00906 | A1 | 1/1991 |

(Continued)

OTHER PUBLICATIONS

Koide, "Designed triple helical peptides as tools for collagen biochemistry and matrix engineering" Phil. Trans. R. Soc B, 362:1281-91, 2007.*

(Continued)

*Primary Examiner* — Maher M Haddad

(74) *Attorney, Agent, or Firm* — Finnegan, Henderson, Farabow, Garrett & Dunner LLP

(57) ABSTRACT

A collagen scaffold domain, including a collagenous or collagen-like domain, which directs self-trimerization is provided. The collagen scaffold domain can be fused to one or more heterologous domains, such as an antibody domain. Methods for generating and using the scaffold domains and fusion proteins are also provided.

35 Claims, 20 Drawing Sheets

Specification includes a Sequence Listing.

(56) References Cited

FOREIGN PATENT DOCUMENTS

| | | | |
|---|---|---|---|
| WO | WO 91/10741 | A1 | 7/1991 |
| WO | WO 91/17271 | A1 | 11/1991 |
| WO | WO 92/01047 | A1 | 1/1992 |
| WO | WO 92/03917 | A1 | 3/1992 |
| WO | WO 92/03918 | A1 | 3/1992 |
| WO | WO 92/09690 | A2 | 6/1992 |
| WO | WO 92/15679 | A1 | 9/1992 |
| WO | WO 92/18619 | A1 | 10/1992 |
| WO | WO 92/20791 | A1 | 11/1992 |
| WO | WO 93/01288 | A1 | 1/1993 |
| WO | WO 94/04678 | A1 | 3/1994 |
| WO | WO 95/31540 | A1 | 11/1995 |
| WO | WO 98/56906 | A1 | 12/1998 |
| WO | WO 2005/037852 | A2 | 4/2005 |
| WO | WO 2005/070966 | A2 | 8/2005 |
| WO | WO 2006/089690 | A1 | 8/2006 |

OTHER PUBLICATIONS

Cuesta, "Comment on "Production of multivalent protein binders using a self-trimerization collagen-like peptide scaffold"," FASEB J. 22: 3417-3418 (2008).

Fan et al., "Production of multivalent protein binders using a self-trimerizing collagen-like peptide scaffold," FASEB J. 22: 3795-3804 (2008).

Sanchez-Arevalo Lobo et al., "Enhanced antiangiogenic therapy with antibody-collagen XVIII NC1 domain fusion proteins engineered to exploit matrix remodeling events," Int. J. Cancer 119:455-462 (2006).

Abramowicz et al., "Release of tumor necrosis factor, interleukin-2, and gamma-interferon in serum after injection of OKT3 monoclonal antibody in kidney transplant recipients" *Transplantation* 47:606-608, 1989.

Adams et al., "Monoclonal antibody therapy of cancer" *Nat. Biotechnol.* 23(9):1147-1157, 2005.

Arakawa et al., "Cloning and sequencing of the VH and V kappa genes of an anti-CD3 monoclonal antibody, and construction of a mouse/human chimeric antibody" *J. Biochem.* 120(3):657-662, 1996.

Bächinger et al., "Folding mechanism of the triple helix in type-III collagen and type-III pN-collagen. Role of disulfide bridges and peptide bond isomerization" *Eur. J. Biochem.* 106:619-632, 1980.

Barbas et al., "Assembly of combinatorial antibody libraries on phage surfaces: the gene III site" *Proc. Natl. Acad. Sci. USA* 88:7978-7982, 1991.

Berg et al., "The thermal transition of a non-hydroxylated form of collagen. Evidence for a role for hydroxyproline in stabilizing the triple-helix of collagen" *Biochem. Biophys. Res. Commun.* 52:115-120, 1973.

Bird et al., "Single-chain antigen-binding proteins" *Science* 242:423-426, 1988.

Boudko et al., "Trimerization and Triple Helix Stabilization of the Collagen XIX NC2 Domain" *J. Biol. Chem.* 283:34345-34351, 2008.

Boudko et al., "Nucleation and propagation of the collagen triple helix in single-chain and trimerized peptides: transition from third to first order kinetics" *J. Mol. Biol.* 317:459-470, 2002.

Carter et al., "Humanization of an anti-p185$^{HER2}$ antibody for human cancer therapy" *Proc. Natl. Acad. Sci. USA* 89:4285-4289, 1992.

Chatenoud et al., "Systemic reaction to the anti-T-cell monoclonal antibody OKT3 in relation to serum levels of tumor necrosis factor and interferon-gamma" *N. Engl. J. Med.* 320:1420-1421, 1989.

Chopra et al., "Conformational implications of enzymatic proline hydroxylation in collagen" *Proc. Natl. Acad. Sci. USA* 79:7180-7184, 1982.

Chou, M-Y. et al., "Genomic Organization and Characterization of the Human Type XXI Collagen (COL21A1) Gene" *Genomics* 79:395-401, 2002.

Cosimi et al., "Use of monoclonal antibodies to T-cell subsets for immunologic monitoring and treatment in recipients of renal allografts" *N. Engl. J. Med.* 305:308-314, 1981.

Devereux et al., "A comprehensive set of sequence analysis programs for the VAX" *Nucleic Acids Research* 12(1):387-395, 1984.

Engel et al., "The triple helix in equilibrium with coil conversion of collagen-like polytripeptides in aqueous and nonaqueous solvents. Comparison of the thermodynamic parameters and the binding of water to (L-Pro-L-Pro-Gly)n and (L-Pro-L-Hyp-Gly)n" *Biopolymers* 16:601-622, 1977.

Fietzek et al., "The primary structure of collagen" *Int. Rev. Connect. Tissue Res.* 7:1-60, 1976.

Frank et al., "Collagen triple helix formation can be nucleated at either end" *J. Biol. Chem.* 278(10):7747-7750, 2003.

Frank et al., "Stabilization of short collagen-like triple helices by protein engineering" *J. Mol. Biol.* 308(5):1081-1089, May 18, 2001.

Goldman et al., "Evolution of renal function during treatment of kidney graft rejection with OKT3 monoclonal antibody" *Transplantation* 50:158-159, 1990.

Goldstein et al., "A randomized clinical trial of OKT3 monoclonal antibody for acute rejection of cadaveric renal transplants. Ortho Multicenter Transplant Study Group" *N. Engl. J. Med.* 313:337-342, 1985.

Gram et al., "In vitro selection and affinity maturation of antibodies from a naive combinatorial immunoglobulin library" *Proc. Natl. Acad, Sci. USA* 89:3576-3580, 1992.

Graversen et al., "Mutational analysis of affinity and selectivity of kringle-tetranectin interaction. Grafting novel kringle affinity ontp the trtranectin lectin scaffold" *J. Biol. Chem.* 275(48):37390-37396, 2000.

Gribskov et al., "Sigma factors from *E. coli, B. subtilis*, phage SP01, and phage T4 are homologous proteins" *Nucleic Acids Research* 14(16):6745-6763, 1986.

Griffiths et al., "Human anti-self antibodies with high specificity from phage display libraries" *EMBO Journal* 12(2):725-1993.

Håkansson et al., "Collectin structure: a review" *Protein Sci.* 9:1607-1617, 2000.

Håkansson et al., "Crystal structure of the trimeric alpha-helical coiled-coil and the three lectin domains of human lung surfactant protein D" *Structure* 7:255-264, 1999.

Harbury et al., "A switch between two-, three-, and four-stranded coiled coils in GCN4 leucine zipper mutants" *Science* 262:1401-1407, 1993.

Holler et al., "Two adjacent trimeric Fas ligands are required for Fas signaling and formation of a death-inducing signaling complex" *Mol. Cell Biol.* 23:1428-1440, 2003.

Holliger et al., "Engineered antibody fragments and the rise of single domains" *Nature Biotechnol.* 23(9):1126-1136, 2005.

Hoogenboom et al., "Multi-subunit proteins on the surface of filamentous phage: methodologies for displaying antibody (Fab) heavy and light chains" *Nucleic Acis Research* 19(15):4133-4137, 1991.

Hoppe et al., "A parallel three stranded alpha-helical bundle at the nucleation site of collagen triple-helix formation" *FEBS Lett.*, 344:191-195, 1994.

Huang et al., "A trimeric anti-HER2/neu ScFv and tumor necrosis factor-alpha fusion protein induces HER2/neu signaling and facilitates repair of injured epithelia" *J. Pharm. Exp. Ther.* 316(3):983-991, 2006.

Huston et al., "Protein engineering of antibody binding sites: recovery of specific activity in an anti-digoxin single-chain Fv analogue produced in *Escherichia coli*" *Proc. Natl. Acad. Sci. USA*, 85:5879-5883, 1988.

Ito et al., "Development of an artificial antibody system with multiple valency using an Fv fragment fused to a fragment of protein A" *J. Biol. Chem.* 268(27):20668-20675, 1993.

Koide, T. et al., "Synthesis of heterotrimeric collagen models containing Arg residues in Y-positions and analysis of their conformational stability" *Bioorg. Med. Chem. Lett.*,14:125-128, 2004.

Kung et al., "Monoclonal antibodies defining distinctive human T cell surface antigens" *Science* 206:347-349, 1979.

(56) References Cited

OTHER PUBLICATIONS

Li, H-C. et al., "Assembly of homotrimeric type XXI minicollagen by coexpression of prolyl 4-hydroxylase in stably transfected *Drosophila melanogaster* S2 cells" *Biochem. Biophys. Res. Commun.* 336:375-385, 2005.
Liu et al., "Generation and characterization of a novel tetravalent anti-CD22 antibody with improved antitumor activity and pharmacokinetics" *Int. Immunopharmacol.* 6:791-799, 2006.
Lynn et al., "Antigenicity and immunogenicity of collagen" *J. Biomed. Mater. Res. B Appl. Biomater.* 71:343-354, 2004.
Mazzorana et al., "Collagenous Sequence governs the Trimeric Assembly of Collagen XII" *J. Biol. Chem.* 276:27989-27998, 2001.
Miller et al., "Design, construction, and in vitro analyses of multivalent antibodies" *J. Immunol.* 170:4854-4861, 2003.
Mizuno et al., "Thermal stability and folding of collagen triple helices" *Conn. Tissue* 35:207-217, 2003.
Mohs et al., "Mechanism of stabilization of a bacterial collagen triple helix in the absence of hydroxyproline" *J. Biol. Chem.* 282:29757-29765, 2007.
Morrison et al., "Chimeric human antibody molecules: mouse antigen-binding domains with human constant region domains" *Proc. Natl. Acad. Sci. USA* 81:6851-6855, 1984.
Needleman et al., "A general method applicable to the search for similarities in the amino acid sequence of two proteins" *J. Mol. Biol.* 48:443-453, 1970.
Nishimura et al., "Recombinant human-mouse chimeric monoclonal antibody specific for common acute lymphocytic leukemia antigen" *Cancer Research* 47:999-1005, 1987.
Ortega et al., "New functional roles for non-collagenous domains of basement membrane collagens" *J. Cell Sci.* 115:4201-4214, 2002.
Ottl et al., "Disulfide-Bridged Heterotrimeric Collagen Peptides Containing the Collagenase Cleavage Site of Collagen Type I. Synthesis and Conformational Properties" *J. Am. Chem. Soc.* 121(4):653-661, 1999.
Persikov et al., "Amino acid propensities for the collagen triple-helix" *Biochemistry* 39:14960-14967, 2000.
Persikov et al., "Prediction of collagen stability from amino acid sequence" *J. Biol. Chem.* 280(19):19343-19349, 2005.
Persikov et al. "Equilibrium thermal transitions of collagen model peptides" *Protein Sci.* 13:893-902, 2004.
Prockop et al. "Collagens: molecular biology, diseases, and potentials for therapy" *Annu. Rev. Biochem.* 64:403-434, 1995.
Queen et al., "A humanized antibody that binds to the interleukin 2 receptor" *Proc. Natl. Acad. Sci. USA* 86:10029-10033, 1989.
Riechmann et al., "Reshaping human antibodies for therapy" *Nature* 332:323-327, 1988.
Rosenbloom et al., "Hydroxyproline content determines the denaturation temperature of chick tendon collagen" *Arch. Biochem. Biophys.* 158:478-484, 1973.
Sakakibara et al., "Synthesis of (Pro-Hyp-Gly)n of defined molecular weights. Evidence for the stabilization of collagen triple helix by hydroxypyroline" *Biochim. Biophys. Acta* 303:198-202, 1973.
Shaw et al., "FACIT collagens: diverse molecular bridges in extracellular matrices" *Trends Biochem. Sci.* 16:191-194, 1991.
Sheriff et al., "Human mannose-binding protein carbohydrate recognition domain trimerizes through a triple alpha-helical coiled-coil" *Nat. Struct. Biol.* 1:789-794, 1994.
Shopes, "A genetically engineered human IgG mutant with enhanced cytolytic activity" *J. Immunol.* 148:2918-2922, 1992.
Shuford et al., "Effect of light chain V region duplication on IgG oligomerization and in vivo efficacy" *Science* 252:724-727, 1991.
Smith et al., "Comparison of biosequences" *Adv. Appl. Math.* 2:482-489, 1981.
Smith, R. et al., "Localized expression of an anti-TNF single-chain antibody prevents development of collagen-induced arthritis" *Gene Ther.* 10(15):1248-1257, 2003.
Söder, S. et al., "The NC1 domain of human collagen IV is necessary to initiate triple helix formation" *Biochem. Biophys. Res. Comm.* 325:276-280, 2004.
Sun et al., "Chimeric antibody with human constant regions and mouse variable regions directed against carcinoma-associated antigen 17-1A." *Proc. Natl. Acad. Sci. USA* 84:214-218, 1987.
Toussaint et al., "Possible nephrotoxicity of the prophylactic use of OKT3 monoclonal antibody after cadaveric renal transplantation" *Transplantation* 48:524-526, 1989.
Tuaillon et al., "Human immunoglobulin heavy-chain minilocus recombination in transgenic mice: gene-segment use in mu and gamma transcripts" *Proc. Natl. Acad. Sci. USA* 90:3720-3724, 1993.
Wada et al., "Codon usage tabulated from the GenBank genetic sequence data" *Nucleic Acids Research* 20:2111-2118, 1992.
Weis et al., "Trimeric structure of a C-type mannose-binding protein" *Structure* 2:1227-1240, 1994.
Wolff et al., "Monoclonal antibody homodimers: enhanced antitumor activity in nude mice" *Cancer Res.* 53:2560-2565, 1993.
Wolff et al., "Human monoclonal antibody homodimers. Effect of valency on in vitro and in vivo antibacterial activity" *J. Immunol.* 148:2469-2474, 1992.
Yang et al., "Gly-Pro-Arg confers stability similar to Gly-Pro-Hyp in the collagen triple-helix of host-guest peptides" *J. Biol. Chem.* 272:28837-28840, 1997.
European Patent Application No. 08250284.0 entitled "Trimeric collagen scaffold antibodies", filed Jan. 23, 2008, by Industrial Technology Research Institute, Inventors: Chou et al.: Extended European Search Report with Opinion, dated Nov. 4, 2008, 10 pages.
European Patent Application No. 06291927.9 entitled "Recombinant triplex scaffold-based polypeptides", filed Dec. 14, 2006, by Industrial Technology Research Institute, Inventors: Chou et al.: Extended European Search Report with Opinion, dated May 10, 2007, 6 pages.
European Patent Application No. 10075641.0 entitled "Recombinant triplex scaffold-base polypeptides", filed Dec. 14, 2006, by Industrial Technology Research Institute, Inventors: Chou et al.: Extended European Search Report with Opinion, dated Mar. 20, 2012, 6 pages.
European Patent Application No. 10075642.8 entitled "Recombinant triplex scaffold-base polypeptides", filed Dec. 14, 2006, by Industrial Technology Research Institute, Inventors: Chou et al.: Extended European Search Report with Opinion, dated Mar. 27, 2012, 7 pages.
Kadler, K.E. et al., "Collagens at a glance," *J. Cell Sci.* 120:1955-1958, 2007.
Bornstein, "The Incomplete Hydroxylation of Individual Prolyl Residues in Collagen" *J. Biol. Chem.* 1967, 242:2572:2574.

* cited by examiner

A

Collagen Scaffold Antibody

B

OKT3mC21x528

Bispecific T-cell engager

A

B

A

B

A

B

A

B

C

A

B

C

A

B

C

A

B

C

A

B

C

A

B

C

A

B

TRIMERIC COLLAGEN SCAFFOLD ANTIBODIES

CROSS REFERENCE TO RELATED APPLICATION

This application is a continuation-in-part of U.S. application Ser. No. 11/609,410, filed Dec. 12, 2006, which was published as U.S. Patent Application Publication No. 2007/0264687, now abandoned, which claims priority to U.S. Application No. 60/750,746, filed Dec. 15, 2005, which are both incorporated herein by reference.

BACKGROUND OF THE INVENTION

Field of the Invention

Protein-based binding reagents have various uses in therapeutic or diagnostic application. Antibodies have proven to be an excellent paradigm for such reagents. Indeed, a number of monoclonal antibodies (mAbs) have been successfully used for treating cancers, infectious diseases, and inflammatory diseases (Adams et al., *Nat. Biotechnol.* 2005 September; 23:1147-57.).

Description of the Related Art

Antibody affinity is a key factor in the success of an antibody as a therapeutic agent. An antibody with high affinity allows the antibody to compete effectively with the natural ligand for the targeted receptor to reduce dosage, toxicity, and cost. Multimerization of antigen binding sites has been shown to be an effective means of increasing the overall strength of the binding of an antibody to an antigen which is defined as the antibody avidity (functional affinity) (Miller et al., *J Immunol* 170:4854-4861, 2003; Rheinnecker et al., *J Immunol* 157:2989-2997, 1996; Shopes, *J Immunol* 148:2918-2922, 1992; Shuford et al., *Science* 252:724-727, 1991; Wolff et al., *J Immunol* 148:2469-2474, 1992). Multivalent antibodies have increased antitumor activity in vivo (Liu et al., *Int Immunopharmacol* 6:79 1-799, 2006; Wolff et al., *Cancer Res* 53:2560-2565, 1993). Due to the bivalent nature of immunoglobulin G (IgG), conventional and engineered IgG cannot be used for simultaneous binding to more than two different antigens. Thus, there is a need for multivalent or multi-specific protein-based binding reagents.

In some cases, avoiding the effector function, such as antibody-dependent cell-mediated cytotoxicity (ADCC) and complement dependent cytotoxicity (CDC), through engineering the Fc region is necessary to reduce mitogenicity side-effects. For example, the murine anti-human CD3 mAb (Orthoclone OKT3, muromonab-CD3), is a potent immunosuppressive agent targeting the T-cell receptor (TCR/CD3 complex on human T cells. It has been used during the last two decades to prevent or treat allograft rejection (Cosimi et al., *N Engl J Med* 305:308-314, 1981; Group, *N Engl J Med* 313:337-342, 1985; Kung et al., *Science* 206:347-349, 1979). However, one major drawback to the use of this therapy is the systemic release of cytokines such as TNF-α, IL-2, and IFN-γ, which result in a series of adverse mitogenic effects, including flu-like symptoms, respiratory distress, neurological symptoms, and acute tubular necrosis (Abramowicz et al., *Transplantation* 47:606-608, 1989; Chatenoud et al., *N Engl J Med* 320:1420-1421, 1989; Goldman et al., *Transplantation* 50:158-159, 1990; Toussaint et al., *Transplantation* 48:524-526, 1989). Since the mitogenic activity of OKT3 and other anti-CD3 mAbs depends upon extensive TCR/CD3 cross-linking via binding to FcR-positive cells (e.g. monocytes), recent efforts have been devoted to developing nonmitogenic forms of anti-CD3 antibodies by altering binding to FcR. Thus, there is a need for protein-based binding reagents that have high affinity, low mitogenic effect, and high in vivo stability.

Collagen is the most abundant protein in mammals. It is an extracellular matrix protein that contains one or more triple-helical regions (collagenous domains) with a repeating triplet sequence Gly-X-Y, where X and Y are frequently proline (amino acid code, P or Pro) and hydroxyproline (amino acid code, O or Hyp). The presence of such triplets allows three collagen polypeptide chains (α-chains) to fold into a triple-helical conformation. Many collagen-like proteins with collagenous domains are present in human serum and serve as an innate immune system in protection from infectious organisms. These include complement protein C1q, macrophage receptors, collectin family proteins-mannose binding lectin (MBL), ficolins and surfactant proteins A and D (SP-A and SP-D). A common structural feature among these "defense collagen" molecules is that all of them are in multi-trimeric protein units with a target-binding domain at the C-terminus. Consequently, multimerization significantly increases the functional affinity of the binding domain of these defense collagen molecules.

Trimerization of heterologous fusion proteins containing collagenous domain(s) has been accomplished by employing either a homogeneous or heterologous trimerization domain fused to the collagenous domain to drive the collagen triplex formation. Examples of a trimer-oligomerizing domain include a C-propeptide of procollagens, a coiled-coil neck domain of collectin family proteins, a C-terminal portion of FasL and a bacteriophage T4 fibritin foldon domain (Frank et al., (2001) *J Mol Biol* 308: 1081-1089; Holler et al., (2003) *Mol Cell Biol* 23: 1428-1440; Hoppe et al., (1994) *FEBS Lett* 344: 191-195).

The trimeric assembly of fibrillar collagens (types I, II, III, IV, V, and XI) and collectin family proteins are initiated by trimeric association of their large globular C-terminal domains (C-propeptides, ~250 amino acids) and C-terminal coiled-coil neck domains (~35 amino acids), respectively, following by propagation of the collagen domain(s) in a zipper-like fashion from the C to the N terminus (Bachinger et al., (1980) *Eur J Biochem* 106: 619-632; Hakansson et al., (1999) *Structure* 7: 255-264; Hakansson and Reid, (2000) *Protein Sci* 9: 1607-1617; Prockop and Kivirikko, (1995) *Annu Rev Biochem* 64: 403-434; Sheriff et al., (1994) *Nat Struct Biol* 1: 789-794; Weis and Drickamer, (1994) *Structure* 2: 1227-1240).

The sequence Gly-Pro-Hyp is the most stabilizing and most common triplet in collagen and the peptide $(\text{Gly-Pro-Hyp})_{10}$ (SEQ ID NO: 19) can self-associate into a highly stable triple helical structure (Chopra and Ananthanarayanan, (1982) *Proc Natl Acad Sci USA* 79: 7180-7184; Engel et al., (1977) Biopolymers 16: 601-622; Sakakibara et al., (1973) *Biochim Biophys Acta* 303: 198-202; Yang et al., (1997) *J Biol Chem* 272: 28837-28840). In contrast to chemically synthesized $(\text{Gly-Pro-Hyp})_{10}$ (SEQ ID NO: 19) peptide, the $(\text{Gly-Pro-Pro})_{10}$ (SEQ ID NO: 20) peptide does not self-assemble into a stable triple-helix under physiological conditions (Engel et al., (1977) *Biopolymers* 16: 601-622). For obtaining a thermally stable $(\text{Gly-Pro-Pro})_{10}$ (SEQ ID NO: 20) triplex, two approaches have been described. First, a interchain disulfide-bonded $(\text{Gly-Pro-Pro})_{10}$ (SEQ ID NO: 20) triplex was obtained in vitro by a redox-shuffling process of a disulfide knot of type III collagen either C- or N-terminal adjacent to the collagen-like peptide at 20° C. (Boudko et al., (2002) *J Mol Biol* 317: 459-470; Frank et al., (2003) *J Biol Chem* 278: 7747-7750). Second, a stable heterologous trimerizing foldon domain derived from bacteriophage T4 fibritin was fused to the C-terminus of (Gly-Pro-Pro)$_{10}$ (SEQ ID NO: 20) peptide to drive the trimerization and correct folding of the collagen-like peptide in a P4H-deficient *E. coli* expression system (Frank et al., (2001) *J Mol Biol* 308: 1081-1089). Many studies have examined the melting temperatures/stability of G-X-Y repeats. Frank et al., (2001); Persikov et al., (2000) *Biochemistry* 39, 14960-14967; Persikov et al., (2004) *Protein Sci.* 13: 893-902; and Mohs et al., (2007) *J. Biol. Chem.* 282: 29757-29765. Based on these studies, the stability of various repeat structures can be predicted.

The approaches described above are limited in their use because they may not support normal trimerizing and folding of a heterologous polypeptide, and may introduce a hetero-antigenetic fragment associated with the risk of an immune response that could severely limit potential therapeutic applications. Thus, what is needed is an in vivo expression system capable of forming a thermally stable triple helical structure that drives the formation of a trimeric fusion protein, enabling use of such trimerized polypeptides both in vitro and in vivo.

The recombinant expression of collagens and hydroxyproline-containing peptides with functional triple-helix conformation requires specific post-translational enzymes, in particular prolyl 4-hydroxylase (P4H) (Prockop and Kivirikko, (1995) *Annu Rev Biochem* 64: 403-434). Prolines specified in the Y position of Gly-X-Y motif of collagen are generally post-translationally modified to 4-hydroxyproline by prolyl 4-hydroxylase (P4H) to stabilize the triple-helical structure of collagen. In the absence of proline hydroxylation, the essential triple helical conformation of collagen is thermally unstable at below physiological temperatures (Berg and Prockop, (1973) *Biochem Biophys Res Commun* 52: 115-120; Rosenbloom et al., (1973) *Arch Biochem Biophys* 158: 478-484). Procaryotes do not possess any P4H activity. Yeasts and insect cells exhibit insufficient enzyme activity to achieve recombinant collagen expression unless exogenous P4H genes (both $\alpha$ and $\beta$ subunits) are introduced simultaneously to form an active $\alpha_2\beta_2$ tetramer.

The non-fibrillar FACIT (fibril-associated collagen with interrupted triple-helices) collagens (types IX, XII, XIV, XVI, XIX, XX, XXI and XXII) are a subgroup within the collagen family. They appear to connect with fibrillar collagens and other matrix components or cells (Shaw and Olsen, (1991) *Trends Biochem Sci* 16: 191-194). In FACITs, the two conserved cysteines, separated by four amino acids, are located at the junction of the COL1 and NC1 domains and are responsible for interchain disulfide bonding among the three assembled collagen chains (Mazzorana et al., (2001) *J Biol Chem* 276: 27989-27998), which is hereby specifically incorporated by reference in its entirety.

Type XII and XXI minicollagens comprising the extreme C-terminal collagenous (COL1) and noncollagenous (NC1) domains, along with the two subunits of human P4H genes have been co-expressed in a baculovirus-infected *Trichoplusia ni* and *Drosophila* S2 insect cells, respectively (Mazzorana et al., (2001) *J Biol Chem* 276: 27989-27998; Li et al., (2005) *Biochem Biophys Res Commun* 336: 375-385). Formation of interchain disulfide-bonded minicollagen XII and XXI depends on the hydroxyproline content of collagen chains, suggesting that the folding of the triple helix precedes the formation of the disulfide bonds. Insufficient prolyl hydroxylation in minicollagen XXI leads to the production of interchain disulfide-bonded dimers and intrachain disulfide-bonded monomers (Li et al., (2005) *Biochem Biophys Res Commun* 336: 375-385). Constructs containing the entire COL1 domain of chicken collagen XII could form trimers. Mazzorana et al. have shown that constructs containing the entire NC1 domain of chicken collagen XII and the only the five terminal G-X-Y repeats of the COL1 domain could not form trimers. The presence of five additional C-terminal G-X-Y repeats of the COL1 domain allowed the formation of trimers. The constructs used by Mazzorana contained a short fragment of human c-myc protein as a tag. As such, Mazzorana did not address the effect of trimerization with these sequences on the folding or functionality of an attached molecule or the effect of a larger attached molecule on self-trimerization.

BRIEF SUMMARY OF THE INVENTION

This invention relates to compositions, methods, and kits comprising trimeric antibodies. The antibodies can have high avidity, low mitogenic effects, and high in vivo stability. The antibodies can be multivalent or multi-specific.

The invention encompasses a trimeric soluble antibody comprising three polypeptides, wherein each polypeptide comprises a collagen scaffold domain comprising at least 10, G-X-Y repeats; wherein G is glycine, X is any amino acid, and Y is any amino acid, wherein at least 10 of the G-X-Y repeats are G-P-P or G-P-O, wherein, at least 6 of the G-X-Y repeats are G-P-O, and wherein P is proline and O is hydroxyproline; and an antibody domain, wherein the collagen-like domains of the three polypeptides interact with each other to form a trimeric soluble antibody that binds to a ligand with an avidity of at least $10^7$ $M^{-1}$ (shown by equilibrium association constant, $K_A$).

The invention also encompasses a trimeric soluble antibody comprising three polypeptides, wherein each polypeptide comprises a collagen scaffold domain comprising at least 10 G-X-Y repeats; wherein G is glycine, X is any amino acid, and Y is any amino acid; wherein at least 6 of the Y residues are hydroxyproline; and an antibody domain, wherein the collagen scaffold domains of the three polypeptides interact with each other to form a trimeric soluble antibody that specifically binds to a ligand with an avidity of at least $10^7$ $M^{-1}$.

The invention also encompasses a trimeric soluble antibody comprising three polypeptides, wherein each polypeptide comprises a collagen scaffold domain comprising at least 6, at least 7, or at least 8 G-P-O repeats and an antibody domain; wherein the collagen scaffold domains of the three polypeptides interact with each other to form a trimeric soluble antibody that specifically binds to a ligand with an avidity of at least $10^7$ $M^{-1}$.

In certain embodiments, the trimeric soluble antibody binds to its ligand with an avidity of at least $10^8$ $M^{-1}$ or with an avidity of at least $10^9$ $M^{-1}$.

In certain embodiments, the ligand for the trimeric soluble antibody is human epidermal growth factor receptor, human CD3, human HER2/neu, or human TNF-$\alpha$.

The trimeric soluble antibody can further comprise a coding sequence for a marker polypeptide. In a preferred embodiment, the marker polypeptide is a luciferase polypeptide. In another preferred embodiment, the marker polypeptide is a green fluorescent polypeptide.

In one embodiment, the collagen-like domain comprises the sequence (G-P-P/O)$_{10}$ (SEQ ID NO: 21). In one embodiment, each polypeptide comprises less than 13 G-X-Y repeats. In one embodiment, each polypeptide comprises less than 20 G-X-Y repeats. In one embodiment, each polypeptide comprises less than 30 G-X-Y repeats. In one embodiment, each polypeptide comprises less than 50 G-X-Y repeats.

In one embodiment, each polypeptide does not contain a collagen NC1 domain. In one embodiment, each polypeptide does not contain a disulfide knot. In one embodiment, each polypeptide does not contain a bacteriophage T4 fibritin foldon domain.

In one embodiment, each polypeptide has a molecular weight of less than 42 kD. In one embodiment, the trimeric soluble antibody has a molecular weight of less than 130 kD.

In one embodiment, more than ⅓ of the G-X-Y repeats are G-P-P or G-P-O. In one embodiment, more than ½ of the G-X-Y repeats are G-P-P or G-P-O. In one embodiment, more than ⅔ of the G-X-Y repeats are G-P-P or G-P-O. In one embodiment, more than ¾ of the G-X-Y repeats are G-P-P or G-P-O. In one embodiment, all of the G-X-Y repeats are G-P-P or G-P-O. In one embodiment, the collagen-like domain comprises the sequence $(G\text{-}P\text{-}P/O)_5$GKPGKP$(G\text{-}P\text{-}P/O)_6$ (SEQ ID NO: 22).

The invention encompasses a nucleic acid encoding a trimeric soluble antibody. The invention further encompasses an expression vector that expresses the trimeric soluble antibody, when introduced into a host cell. The invention also encompasses a host cell comprising an expression vector that expresses the trimeric soluble antibody.

The invention encompasses a method and kit for generating a trimeric soluble antibody comprising joining a nucleic acid encoding a collagen scaffold domain comprising 10-30 G-X-Y repeats; wherein G is glycine, X is any amino acid, and Y is any amino acid, and wherein at least 10 of the G-X-Y repeats are G-P-P; in-frame with a nucleic acid encoding an antibody domain for a ligand; and expressing the encoded polypeptide in a cell that hydroxyprolinates at least 6 of the G-P-P repeats at the Y position; wherein the hydroxyprolinated collagen-like domains of three polypeptides interact with each other to form a trimeric soluble antibody that binds to a ligand with an avidity of at least $10^7$ $M^{-1}$.

The invention encompasses a method and kit for modulating (i.e., either inhibiting or augmenting) the biological activity of a ligand comprising incubating a trimeric soluble antibody comprising three polypeptides with the ligand; wherein each polypeptide comprises a collagen scaffold domain comprising at least 10 G-X-Y repeats; wherein G is glycine, X is any amino acid, and Y is any amino acid, wherein at least 10 of the G-X-Y repeats are G-P-P or G-P-O, wherein at least 6 of the G-X-Y repeats are G-P-O, and wherein P is proline and O is hydroxyproline; and an antibody domain; wherein the hydroxyprolinated collagen-like domains of three polypeptides interact with each other to form a trimeric soluble antibody that binds to a ligand with an avidity of at least $10^7$ $M^{-1}$; and wherein the binding of the trimeric soluble antibody to the ligand inhibits the biological activity of the ligand.

The invention encompasses a method and kit for detecting a ligand comprising incubating a trimeric soluble antibody comprising three polypeptides with the ligand; wherein each polypeptide comprises a collagen scaffold domain comprising at least 10 G-X-Y repeats; wherein G is glycine, X is any amino acid, and Y is any amino acid, wherein at least 10 of the G-X-Y repeats are G-P-P or G-P-O, wherein at least 6 of the G-X-Y repeats are G-P-O, and wherein P is proline and O is hydroxyproline; and an antibody domain; wherein the hydroxyprolinated collagen-like domains of three polypeptides interact with each other to form a trimeric soluble antibody that binds to a ligand with an avidity of at least $10^7$ $M^{-1}$; and detecting the binding of the trimeric soluble antibody to the ligand.

In certain embodiments, the trimeric soluble antibody comprises a luciferase polypeptide or a green fluorescent polypeptide.

DETAILED DESCRIPTION OF THE INVENTION

Figure 1:
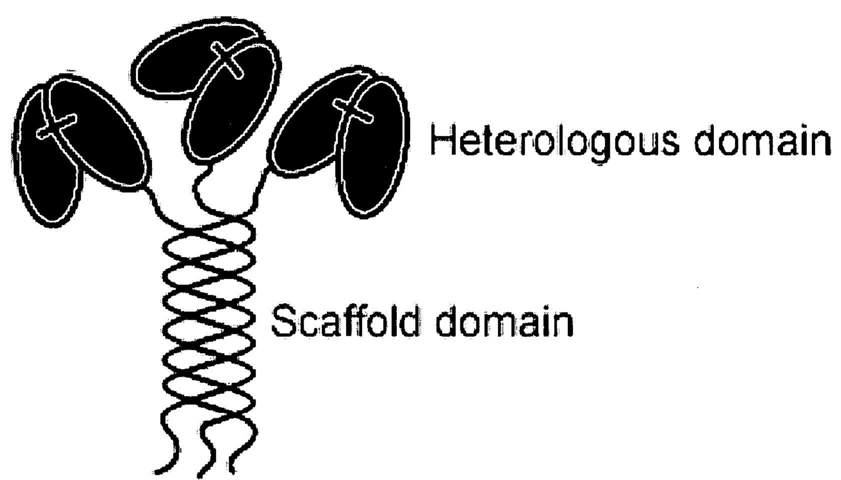
FIG. 1 is a diagram showing a protein complex that has a self-assembled triple helix coil collagen scaffold domain, such as that derived from a human type XXI minicollagen or a collagen-like domain of $(GPP)_{10}$ (SEQ ID NO: 20), and a heterologous domain.

The present invention is based, in part, on the findings that a antibody domain fused in-frame to a collagen scaffold domain allows the trimerization of the scaffold domain to generate a trimeric antibody, and the binding avidity of the resulting trimeric antibody is enhanced as compared to the divalent IgG, and monovalent scFv formats. Trimeric antibodies made according to the invention can have functional affinities (avidities) for their ligands of greater than $10^9$ $M^{-1}$.

In one embodiment, a collagen scaffold domain can be fused in-frame to a binding protein in a fusion polypeptide, such that the collagen scaffold domain drives trimerization of the fusion polypeptide, which retains its ability to bind its ligand. The binding domain can be, for example, a cytokine domain, a cytokine receptor domain, or an antibody domain. In one embodiment, the cytokine is TNF-α. In one embodiment, a collagen scaffold domain can be fused in-frame to an antibody domain to generate a trimeric antibody. In a preferred embodiment, the trimeric antibody is a soluble antibody. A soluble antibody is one that is soluble under physiological conditions. In a preferred embodiment, the soluble trimeric antibody is a secreted antibody. A secreted antibody is one that is secreted by a cell. Secretion of an antibody can be targeted by having a signal sequence on the polypeptide comprising the antibody domain.

In one embodiment, the soluble trimeric antibody has an avidity for its ligand of greater than $10^7$ $M^{-1}$. In one embodiment, the soluble trimeric antibody has an avidity for its ligand of greater than $10^8$ $M^{-1}$. In one embodiment, the soluble trimeric antibody has an avidity for its ligand of greater than $10^9$ $M^{-1}$. In certain embodiments, the soluble trimeric antibody has an avidity for its ligand between $M^{-1}$ and $10^{10}$ $M^{-1}$, between $10^7$ $M^{-1}$ and $10^9$ $M^{-1}$, between $10^7$ $M^{-1}$ and $10^8$ $M^{-1}$, between $10^8$ $M^{-1}$ and $10^{10}$ $M^{-1}$, between $10^8$ $M^{-1}$ and $10^9$ $M^{-1}$, and between $10^9$ $M^{-1}$ and $10^{10}$ $M^{-1}$.

In one embodiment, a thermally stable short collagen-like peptide, such as $(Gly\text{-}Pro\text{-}Pro)_{10}$ (SEQ ID NO: 20), is used as a scaffold domain to drive the trimerization of an antibody domain by expressing the fusion construct in a system with sufficient P4H activity. This approach facilitates the adoption of the stable triple-helical structure, which affects protein valency, stability, and function in vivo.

The present invention encompasses using a collagenous sequence, e.g., minicollagen type XII or XXI, or a collagen-like sequence, e.g., $(Gly\text{-}Pro\text{-}Pro)_{10}$ (SEQ ID NO: 20) or $(GPP)_5GKPGKP(GPP)_6$ (SEQ ID NO: 26), as a collagen scaffold domain capable of self-nucleation and propagation of the heterologous fusion proteins from either C- or N-terminal direction. The present invention avoids the need for any other trimerization structure domains.

Collagen scaffold domain fusion proteins can form a thermally stable triple helical structure by expression of the fusion construct in a prolyl 4-hydroxylase containing system. Moreover, the self-trimerization collagen scaffold of the invention allows attachment of fusion partners to either terminus, as well as to both termini, simultaneously. This has important consequences as the self-trimerization collagen scaffold may be employed to construct molecules that are able to interact (each end with a binding valency up to 3 or 6) simultaneously with two bulky binding partners. The present invention also demonstrates that the trimeric antibodies can fold correctly and exhibit high solubility, avidity, and stability.

As used herein, the term "collagen scaffold domain" is a collagenous or collagen-like domain which allows for formation of a triplex structure by itself, wherein a "triplex structure" is a covalently or non-covalently bound complex of three subunits. As used herein, the term "collagen scaffold domain" refers to the collagenous or collagen-like domains that direct self-trimerization of the scaffold domain.

As used herein, the term "collagen scaffold domain" does not refer to C-propeptides of procollagens, coiled-coil neck domains of collectin or ficolin family proteins, the C-type lectin-like domain of tetranectin, beta-galactosidase trimerization domain, the three coiled-coil helix structure of GCN4 leucine zipper mutant (Harbury et al., (1993) *Science* 262: 1401-1407), C1q and TNF domains of C1q and TNF superfamily proteins, and bacteriophage T4 fibritin foldon domains.

A "collagen scaffold antibody" or "CSA" is an antibody that includes a collagen scaffold domain fused to an antibody domain. A CSA and its coding sequence can comprise any combination of the SEQ IDs that follow. Each of these combinations is specifically contemplated. For example, the CSA can contain one or more of SEQ ID NOs 1, 3, 5 and 9.

Accordingly, one aspect of this invention features an isolated recombinant protein complex that includes a first fusion polypeptide chain containing a first collagen scaffold domain and a first antibody domain fused in-frame to one end of the first collagen scaffold domain; a second fusion polypeptide chain containing a second collagen scaffold domain; and a third fusion polypeptide chain containing a third collagen scaffold domain. The first, second, and third collagen scaffold domains are aligned to form a triple helix coil. The first collagen scaffold domain and first antibody domain are fused in-frame and on the same peptide chain.

The fusion polypeptide chain can include the sequence of an enzymatic domain or a fluorescent protein. Examples of a fluorescent protein include GFP and dsRed, as well as their variants. Examples of an enzymatic domain include that of glutathione S-transferase, luciferase, β-galactosidase, and β-lactamase.

The fusion polypeptide chain can include, or exclude, the sequence of affinity tags for the purpose of detection and purification of the fusion proteins of the invention. Examples of affinity tags include polyhistidine-tag, myc-tag, Strep-tag, FLAG, E-tag, hemagglutin tag, T7, S-tag, HSV, VSV-G, anti-Xpress, and VS-tag.

The "antibody domain" includes one or more complementary-determining regions (CDR) of an immunoglobulin. Accordingly, the antibody domain can include antigen binding parts of an antibody, such as a $V_H$ domain and an Fab. In one embodiment, the first antibody domain contains the sequence of an antigen-binding fragment or a single-chain antibody, e.g., that specific for Cluster Designation 3 (CD3), Epidermal Growth Factor Receptor (EGFR), HER2/neu or Tumor necrosis factor-alpha (TNF-α). The first polypeptide chain can further contain a second antibody domain fused in-frame to the other end of the first scaffold domain.

In one embodiment, a second fusion polypeptide chain contains a second antibody domain. In a preferred embodiment, the first and second antibody domains are identical to each other. The first and second antibody binding domains can bind to an identical binding partner or to two different binding partners. For example, the first antibody domain and second antibody domain can contain the sequences of a first single-chain antibody and a second single-chain antibody that specifically bind to CD3 and EGFR, respectively. In one embodiment, the first and second fusion polypeptide both contain the first and second antibody binding domains.

The second fusion polypeptide chain can contain a third antibody domain fused in-frame to one end of the second scaffold domain, a fourth antibody domain fused in-frame to the other end of the second scaffold domain, or both domains fused in-frame to the two ends. Similarly, the third fusion polypeptide chain can contain a fifth antibody domain fused in-frame to one end of the third scaffold domain, or a sixth antibody domain fused in-frame to the other end of the third scaffold domain, or both. All six antibody domains can be identical to or different from each other. They therefore can bind to 1, 2, 3, 4, 5, or 6 binding partners. In other words, the protein complex can be mono-, di-, tri-, tetra-, penta-, or hexa-valent.

For the first, second, and third scaffold domains to form a triple helix coil, each of the three scaffold domains contains one or more triple helix repeats, known as collagenous or collagen-like domains, each repeat containing a sequence of the following formula: $(G\text{-}X\text{-}Y)_n$ (SEQ ID NO: 33), in which G is a Gly residue; X and Y are any amino acid residues, and preferably, the amino acid proline or hydroxyproline; and n is 5 or greater. As referenced herein, a "repeat" refers to two or more sequential G-X-Y sequences.

The scaffold domain can include a perfect repeating G-X-Y triplet, interrupted by a short imperfection, in which the first position of Gly or the third position of Y residue is missing, found in many naturally occurring collagens and proteins containing collagen-like domains. For example, the scaffold domain of this invention, human type XXI mini-collagen, contains two imperfections, GF and KE, within the collagenous domain.

In certain embodiments, the collagen scaffold domain is a collagen scaffold domain comprising at least 8, at least 9, at least 10, at least 11, at least 12, at least 13, at least 14, at least 15, at least 16, at least 17, at least 18, at least 19, or at least 20 G-X-Y repeats; wherein G is glycine, X is any amino acid, and Y is any amino acid. In certain embodiments, at least 5, at least 6, at least 7, at least 8, at least 9, or at least 10 of the G-X-Y repeats are G-P-P or G-P-O. In certain embodiments, at least 5, at least 6, at least 7, at least 8, at least 9, or at least 10 of the G-X-Y repeats are G-P-O, wherein P is proline and O is hydroxyproline. The collagen scaffold domain directs self-trimerization.

In one embodiment, the collagen scaffold domain comprises the sequence $(G\text{-}P\text{-}P/O)_{10}$ (SEQ ID NO: 21). In one embodiment, the collagen scaffold domain comprises 10 G-X-Y repeats. In certain embodiments, the collagen scaffold domain comprises less than 10, 11, 12, 13, 14, 15, 16, 17, 18, 19, 20, 22, 25, 27, 30, 35, 40, 45, or 50 G-X-Y repeats. In certain embodiments, the collagen scaffold domain is less than 150, 125, 100, 90, 80, 70, 60, 50, or 40 amino acids in length. In one embodiment, the collagen scaffold domain consists essentially of 10-30 G-X-Y repeats, which cause self-trimerization.

In one embodiment, more than ⅓ of the G-X-Y repeats are G-P-P or G-P-O. In one embodiment, more than ½ of the G-X-Y repeats are G-P-P or G-P-O. In one embodiment, more than ⅔ of the G-X-Y repeats are G-P-P or G-P-O. In one embodiment, more than ¾ of the G-X-Y repeats are G-P-P or G-P-O. In one embodiment, all of the G-X-Y repeats are G-P-P or G-P-O. In one embodiment, the scaffold domain comprises the sequence $(G\text{-}P\text{-}P/O)_5$GKPGKP$(G\text{-}P\text{-}P/O)_6$ (SEQ ID NO: 22). In one embodiment, the scaffold domain comprises the sequence $(G\text{-}P\text{-}P/O)_{10}$ (SEQ ID NO: 21), where P/O indicates that the Y position is either P or O.

In a preferred embodiment, the collagen scaffold domain comprises at least 10 G-X-Y repeats, wherein at least 5, at least 6, at least 7, at least 8, at least 9, or at least 10 of the Y residues are hydroxyproline. The collagen scaffold domain directs self-trimerization.

In a preferred embodiment, the collagen scaffold domain comprises at least 5, at least 6, at least 7, at least 8, at least 9, or at least 10 G-P-O repeats and an antibody domain; wherein the collagen scaffold domains of the three polypeptides interact with each other to form a trimeric soluble antibody that specifically binds to a ligand with an avidity of at least $10^7$ $M^{-1}$. In a preferred embodiment, the collagen scaffold domain comprises 6 or 7 G-P-O repeats. The G-P-O repeats can be sequential or can be spaced apart. For example, the G-P-P repeats can be spaced as two in-frame amino acid sequences comprising 3, 4, or 5 G-P-O repeats separated by 1, 2, 3, 4, or 5, GXY repeats. In one embodiment, the collagen scaffold domain comprises $(G\text{-}P\text{-}O)_3$GXY$(GPO)_4$ (SEQ ID NO: 27).

In one embodiment the collagen scaffold domain is the collagenous (COL1) domain of a non-fibrillar FACIT (fibril-associated collagen with interrupted triple-helices) collagen. Preferably, a trimeric antibody comprising the COL1 domain of a non-fibrillar FACIT does not contain the non-collagenous (NC1) domain of the FACIT. In a preferred embodiment, the COL1 domain is from types IX, XII, XIV, XVI, XIX, XX, XXI or XXII collagen. In a preferred embodiment, the trimeric antibody comprises SEQ ID NO:7.

In one embodiment, the collagen scaffold domain has at least 75%, 80%, 85%, 90%, or 95% identity with a complete COL1 domain from types IX, XII, XIV, XVI, XIX, XX, XXI or XXII collagen. In one embodiment, the collagen scaffold domain has at least 75%, 80%, 85%, 90%, or 95% identity with the G-X-Y repeats of a COL1 domain from types IX, XII, XIV, XVI, XIX, XX, XXI or XXII collagen.

In a preferred embodiment, the collagen scaffold domain has at least 75%, 80%, 85%, 90%, or 95% identity with 10, 11, 12, 13, 14, 15, 16, 17, 18, 19, 20, 21, 22, 23, 24, 25, or 30 G-X-Y repeats of a COL1 domain from types IX, XII, XIV, XVI, XIX, XX, XXI or XXII collagen. In a particularly preferred embodiment, the collagen scaffold domain has at least 75%, 80%, 85%, 90%, or 95% identity with 10 G-X-Y repeats of a COL1 domain from type XXII collagen.

In a preferred embodiment, the G-X-Y sequence of the collagen scaffold domain comprises at least 5, at least 6, at least 7, at least 8, at least 9, or at least 10 hydroxyprolines at the Y position.

The percent identity can be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

In one embodiment, the above-described first, second, and third fusion polypeptides are substantially identical, having at least 75% (e.g., any number between 75% and 100%, inclusive) sequence identity to one another. A complex formed by three identical fusion polypeptides is a homotrimer. The three fusion polypeptides can be functional equivalents. A "functional equivalent" refers to a polypeptide derivative of a common polypeptide, e.g., a protein having one or more point mutations, insertions, deletions, truncations, a fusion protein, or a combination thereof, and retaining substantially the ability to form a triple helix coil and the activity of the heterologous domain, such as binding to a ligand.

A heterologous polypeptide, nucleic acid, or gene is a polypeptide, nucleic acid, or gene that is associated with another polypeptide, nucleic acid, or gene with which it is not naturally associated. Two fused domains or sequences are heterologous to each other if they are not adjacent to each other in a naturally occurring protein or nucleic acid.

The invention also includes an isolated recombinant fusion polypeptide (e.g., each of the above-mentioned three fusion polypeptides) that contains (i) a collagen scaffold domain for forming a triple helix coil and (ii) a first heterologous domain fused in-frame to one end of the scaffold domain or a second heterologous domain fused in-frame to the other end of the scaffold domain. The heterologous domain can include one of the antibody domains mentioned above, and can be obtained by various art-recognized methods, such as phage display screening.

An "isolated" polypeptide or protein complex refers to a polypeptide or a protein complex substantially free from naturally associated molecules, i.e., it is at least 75% (i.e., any number between 75% and 100%, inclusive) pure by dry weight. Purity can be measured by any appropriate standard method, for example, by column chromatography, polyacrylamide gel electrophoresis, or HPLC analysis. An isolated polypeptide or protein complex of the invention can be purified from a natural source, produced by recombinant DNA techniques.

Preferably, the three polypeptides that trimerize to form a trimeric antibody are non-contiguous. In another embodiment, the three polypeptides that trimerize to form a trimeric antibody are contiguous, i.e, translated as a single translation product. In this embodiment, the three polypeptides can be joined by two or more flexible hinge regions.

The invention also encompasses an isolated nucleic acid that contains a sequence encoding the just-mentioned fusion polypeptide or a complement of the sequence. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of a vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention. Also within the scope of this invention is a host cell that contains the above-described nucleic acid. Examples include *E. coli* cells, insect cells (e.g., using *Drosophila* S2 cells or baculovirus-infected insect cells), yeast cells, or mammalian cells (e.g., mouse myeloma NS0 cell). See e.g., Goeddel, (1990) Gene Expression Technology: Methods in Enzymology 185, Academic Press, San Diego, Calif.

To produce a fusion polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

To produce a protein complex of this invention, one can culture a host cell containing a first, second, and third nucleic acids respectively encoding the above-mentioned first, second, and third fusion polypeptides in a medium under a condition permitting expression of polypeptides encoded by the three nucleic acids and formation of a triple helix coil between the expressed polypeptides, and purifying the protein complex from the cultured cell or the medium of the cell. Preferably, the host cell is a eukaryotic cell containing an enzymatic activity that hydroxylates a proline residue.

The details of one or more embodiments of the invention are set forth in the accompanying drawing and the description below. Other features, objects, and advantages of the invention will be apparent from the description and drawing, and from the claims.

A soluble trimeric antibody of this invention enjoys advantages over conventional antibodies. On the one hand, when two or more of the six antibody domains are identical to each other, the protein complex can have 2-6 antibody domains that are specific for one binding partner (e.g., antigen) in comparison with a conventional antibody, which has only two such domains. In other words, unlike a conventional antibody, which is only divalent for an antigen, the protein complex can be di-, tri-, tetra-, penta-, or hexavalent. As a result, it can be made to have affinities that are higher than a conventional antibody. Because of the higher affinities, smaller amounts of the protein complex and shorter incubation duration are needed than a conventional antibody to achieve the desired goals, for example, therapeutic effects, thereby lowering treatment costs and minimizing side effects (e.g., unwanted immune responses).

On the other hand, when two or more of the six domains are different from each other, a protein complex of this invention can have 2-6 antibody domains that are specific for 2-6 different binding partners. Unifying multiple binding partner sites of different specificities into one unit, it has the ability to bring together multiple binding partners and therefore have desirable uses in therapy, tissue reconstruction, and assembly of active protein machinery (e.g., a multi-subunit enzyme) at the nanometer level.

For in vivo use in a human, a trimeric antibody of this invention is preferably of human origin. For example, it can include a humanized single-chain antibody sequence fused in-frame to a collagen scaffold domain of human origin. Since many collagen-like proteins with collagenous domains are fairly stable in the blood, the scaffold domain fusion proteins should retain structural integrity in blood as well.

The sequence Gly-Pro-Hyp contributes most to the formation and stabilization of a triple helical structure and the Gly-Pro-Hyp tripeptide repeats self-assemble into a highly stable triple helix. Hence, the collagenous domain of mini-collagen XXI was substituted with a thermally stable short collagen-like peptide $(Gly\text{-}Pro\text{-}Pro)_{10}$ (SEQ ID NO: 20) as a scaffold template for the CSAs described herein, which were expressed in a mammalian system with sufficient P4H activity to facilitate the adoption of the stable triple-helical structure. Indeed, both erb_scFv-Col and OKT3_scFv-Col were assembled into a trimeric structure and erb_scFv-Col can be further oligomerized into a hexamer, presumably through the interchain disulfide crosslinking between the two C-terminal cysteine residues within the two trimers. The oligomerization of erb_scFv-Col from trimer to hexamer is an intracellular process because the reduced trimeric structure does not assemble into higher order structures at concentrations in excess of those normally found in the hexameric form of erb_scFv-Col.

Mouse myeloma NS0 cells are a good expression system for recombinant collagen or collagen-like protein production. Approximately 61% of the total number of proline residues in the Y position of a collagenous GXY triplet sequence of $(Gly\text{-}Pro\text{-}Pro)_{10}$ (SEQ ID NO: 20) is hydroxylated in recombinant erb_scFv-Col. Thus, at least 6 of the Gly-Pro-Pro repeats were hydroxylated in this system. The contribution of the prolyl hydroxylated $(Gly\text{-}Pro\text{-}Pro)_{10}$ (SEQ ID NO: 20) motif to the trimeric assembly of CSA molecules was prominent, since almost no monomeric form of the CSA was present in culture media, as examined by Western blot analysis. The presence of 2 M urea in the purified CSA sample at a temperature of up to 45° C., after 2% SDS loading buffer was added, was not strong enough to dissociate the trimeric form of the GSA, as judged from the level of melted monomers shown in FIG. 6B and FIG. 14B. In the serum stability assays, in which various erb antibody formats were incubated in human serum at 37° C. for up to 7 days, the antibody concentration used in ELISA for erb_scFv-Col was in the nanomolar range, rather than in the sub-micromolar and micromolar ranges as for the bivalent erb_scFv-Fv and the monovalent erb_scFv counterparts, respectively. Therefore, a CSA can retain its multivalent target-binding format under physiological conditions.

The thermally stable trimeric structure of CSA meets the requirement of a multi-purpose multimerizing system for future in vivo use. Many collagen-like proteins with collagenous domains are present in human serum and serve as an innate immune system in protection from infectious organisms. These include complement protein C1q, collectin family proteins—mannose binding lectin (MBL), ficolins and surfactant proteins A and D (SP-A and SP-D). A common structural feature among these "defense collagen" molecules is that all of them are in multi-trimeric protein units with a target-binding domain at the C-terminus. The driving force for the formation of these multi-trimeric structures is similar to those for fibrillar collagens. The three polypeptide chains were firstly trimerized using their coiled-coil neck domain, which is N-terminal next to the target-binding domain, then triple helical folding of the collagen-like domain proceeded in a zipper-like fashion from the C to the N terminus, before finally stacking or interchain disulfide crosslinking of the trimeric molecules using their N-terminal cysteine residues (Hakansson et al., (1999) *Structure* 7: 255-264; Hakansson and Reid, (2000)*Protein Sci* 9: 1607-1617; Sheriff et al., (1994) *Nat Struct Biol* 1: 789-794; Weis and Drickamer, (1994) *Structure* 2: 1227-1240). Consequently, multimerization significantly increases the functional affinity of the binding domain of these defense collagen molecules.

The impact of target-binding avidity was apparent when the various erb and OKT3 antibody species were compared using surface plasmon resonance (SPR) and competition flow cytometry analyses. The binding data demonstrated that increasing the valency in the CSA molecule can improve the degree and specificity of in vivo targeting, leading to enhanced target retention. The effective dosing of trivalent OKT3 CSA for the immunosuppression of T-cell activation is lower than that of the parent OKT3 IgG tested in a mixed lymphocyte reaction.

OKT3_scFv-Col does not induce T-cell proliferation or IL-2 production in human PBMCs, greatly reducing the effects of the OKT3 first dose syndrome that is caused by the release of cytokines as a result of transient T cell activation. This new anti-CD3 format may provide a potent immunosuppressive drug with reduced dosing, toxicity, and cost of therapy. Humanization of murine mAb by CDR-grafting with or without structure-based design to transform CDR residue(s) from murine to human origin often results in a reduction or loss of binding affinity (Queen et al., (1989) *Proc Natl Acad Sci USA* 86: 10029-10033; Riechmann et al., (1988) *Nature* 332: 323-327). In a preferred embodiment, the trimeric soluble antibody does not contain an Fc domain.

Affinity maturation by chain-shuffling using phage-display scFv library screening for high-affinity binders is a tedious process; yet the outcome of improving binding affinity is uncertain. Therefore, many therapeutic antibodies may be hampered by low affinity for the target antigen after humanization. In some cases, the properties of the antibody must be further refined. Polymerization of antigen-binding partners greatly increases their availability for binding to a group of specific identical ligands in very close proximity to a target cell. Different approaches have been proposed to obtain multivalent molecules for improving functional affinity. Some involve creating alternative binding proteins, based either on scaffolds with immunoglobulin (Holliger and Hudson, (2005) *Nat Biotechnol* 23: 1126-1136) or on completely different protein topologies (Binz et al., (2005) *Nat Biotechnol* 23: 1257-1268). For example, the use of Fv fragments fused with protein A Fc-binding domains (Ito and Kurosawa, (1993) *J Biol Chem* 268: 20668-20675), core-streptavidin for the formation of a tetrameric complex (Dubel et al., (1995) *J Immunol Methods* 178: 201-209), or the human tetraminization domain of transcription factor p53 (Rheinnecker et al., (1996) *J Immunol* 157: 2989-2997) has been reported. Non-IgG protein scaffold fragments, such as "anticalins" (Skerra, (2000) *Biochim Biophys Acta* 1482: 337-350), "ankyrin repeats" (Binz et al., (2004) *Nat Biotechnol* 22: 575-582), "Affibody molecules" (Nord et al., (1997) *Nat Biotechnol* 15: 772-777), and the C-type lectin-like domain of tetranectin (Christian et al. International Publication No. WO 98/56906; Graversen et al., (2000) *J Biol Chem* 275: 37390-37396) have recently been adopted to increase target binding affinity, thermal stability, and sensitivity. However, some of these molecules are either heteroantigenetic fragments or not natural components of plasma, and are associated with the risk of an immune response that could severely limit potential therapeutic applications.

A triplex-forming collagen-like peptide fusion scaffold to form a thermally stable multivalent protein binder was used to demonstrate herein that CSA is a new platform that enables improvements to the functional affinity and mitogenicity of therapeutic antibodies. More importantly, fusion of the scFv and the collagen-like scaffold domains in CSA has been proven to bring each domain to fold correctly, without compromising the target-binding activities or the trimeric assembly of the triple helical structure. The triplex-forming collagen-like domain can be used as a scaffold for existing or new protein drugs by trimerizing (even oligomerizing through collagen fibrillar stacking or interchain disulfide crosslinking of the trimeric molecules that are similar to those of the defense collagen family) the active protein in a fusion protein approach, which involves protein hormones, cytokines, lymphokines, growth factors, lectins, enzymes and soluble receptor fragments; or adhesion molecules, such as selectins and integrins.

A protein complex or polypeptide of the invention can be obtained by recombinant technology. One can introduce into suitable host cells nucleic acids encoding polypeptides of the complex and express the polypeptides under a condition permitting expression of polypeptides encoded by the nucleic acids and formation of a triple helix coil between the polypeptides. To facilitate formation of the triple helix coil scaffold, one can co-express in the host cells prolyl 4-hydroxylase (P4H), a key enzyme in the biosynthesis of collagen.

A heterologous protein domain can contain a "binding domain," which includes, but is not limited to, an antibody or a fragment thereof (e.g., an antigen-binding fragment thereof). The term "antibody" as used herein refers to an immunoglobulin molecule or immunologically active portion thereof, i.e., an antigen-binding portion. It refers to a protein comprising at least one, and preferably two, heavy (H) chain variable regions ($V_H$), and at least one and preferably two light (L) chain variable regions ($V_L$). Thus, an "antibody domain" refers to an antibody or an antigen binding portion of an antibody, and includes $V_H$, $V_L$, or Fab domains, Fv fragments of single-chain antibodies (scFv), and VHH domains (see WO 94/4678).

The $V_H$ and $V_L$ regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat et al. (1991) *Sequences of Proteins of Immunological Interest, Fifth Edition*, U.S. Department of Health and Human Services, NIH Publication No. 91-3242, and Chothia et al. (1987) *J. Mol. Biol.* 196:901-917, which are incorporated herein by reference. Each $V_H$ and $V_L$ is normally composed of three CDR's and four FRs, arranged from amino-terminus to carboxy-terminus in the following order: FR1, CDR1, FR2, CDR2, FR3, CDR3, FR4. The antibody can further include a heavy and light chain constant region, to thereby form a heavy and light immunoglobulin chain, respectively. The heavy chain constant region is comprised of three domains, $C_{H1}$, $C_{H2}$, and $C_{H3}$. The light chain constant region is comprised of one domain, $C_L$. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, and IgG4), delta, epsilon, and mu constant region genes, as well as the myriad immunoglobulin variable region genes. Full-length immunoglobulin "light chains" (about 25 kD or 214 amino acids) are encoded by a variable region gene at the $NH_2$-terminus (about 110 amino acids) and a kappa or lambda constant region gene at the COOH-terminus. Full-length immunoglobulin "heavy chains" (about 50 kD or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or "antibody portion," or "fragment"), as used herein, refers to one or more fragments of a full-length antibody that retain the ability to specifically bind to its ligand, or antigen, e.g., EGFR or CD3 polypeptide or a fragment thereof.

Examples of antigen-binding fragments of the antibody include, but are not limited to: (i) a Fab fragment, a monovalent fragment consisting of the $V_L$, $V_H$, $C_L$, and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR), and (vii) $V_L$ or $V_H$ domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single-chain Fv (scFv); see e.g., Bird et al. (1988) *Science* 242:423-426; and Huston et al. (1988) *Proc. Natl. Acad. Sci. USA* 85:5879-5883). Such single-chain antibodies are also encompassed within the term "antigen-binding fragment" of an antibody. These antibody fragments can be obtained using conventional techniques known to those with skill in the art, and the fragments are screened for utility in the same manner as are intact antibodies.

An antibody can be a monoclonal antibody. In one embodiments, the antibody can be recombinantly produced, e.g., produced by phage display or by combinatorial methods. Phage display and combinatorial methods for generating antibodies are known in the art (see e.g., Ladner et al. U.S. Pat. No. 5,223,409; Kang et al. International Publication No. WO 92/18619; Dower et al. International Publication No. 25 WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9: 1370-1372; Hay et al. (1992) *Hum Antibod Hybridomas* 3: 81-85; Huse et al. (1989) *Science* 246: 1275-1281; Griffths et al. (1993) *EMBO J.* 12: 725-734; Hawkins et al. (1992) *J Mol Biol* 226: 889-896; Clackson et al. (1991) *Nature* 352: 624-628; Gram et al. (1992) *Proc Natl Acad Sci USA* 89: 3576-3580; Garrad et al. (1991)

*Bio/Technology* 9: 1373-1377; Hoogenboom et al. (1991) *Nuc Acid Res* 19: 41334137; and Barbas et al. (1991) *Proc Natl Acad Sci USA* 88: 7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), or camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT 15 publication WO 91/10741; Lonberg et al. International Application WO 92/03918; Kay et al. International Application 92/03917; Lonberg, et al. (1994) *Nature* 368: 856-859; Green, L. L. et al. (1994) *Nature Genet.* 7: 13-21; Morrison et al. (1994) *Proc. Natl. Acad. Sci. USA* 81: 6851-6855; Bruggeman et al. (1993) *Year Immunol* 7: 33-40; Tuaillon et al. 1993 *Proc. Natl. Acad. Sci. USA* 90: 3720-3724; Bruggeman et al. (1991) *Eur J Immunol* 21: 1323-1326).

An antibody can be one in which the variable region, or a portion thereof, e.g., the CDR's, are generated in a non-human organism, e.g., a rat or mouse. Chimeric, CDR-grafted, and humanized antibodies can be used. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fe constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184, 187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988) *Science* 240: 1041-1043); Liu et al. (1987) *Proc. Natl. Acad. Sci. USA* 84: 3439-3443; Liu et al., (1987) *J Immunol.* 139:3521-3526; Sun et al. (1987) *Proc. Natl. Acad. Sci. USA* 84: 214-218; Nishimura et al., (1987) *Canc. Res.* 47: 999-1005; Wood et al. et al (1985) *Nature* 314: 446-449; and Shaw et al., (1988) *J. Natl Cancer Inst.* 80: 1553-1559).

A humanized or CDR-grafted antibody will have at least one or two but generally all three recipient CDR's (of heavy and/or light immunoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto. As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., (1985) *Science* 229: 1202-1207, by Oi et al., (1986) *Bio Techniques* 4: 214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a polypeptide of interest or fragment thereof. The recombinant DNA encoding the humanized antibody, or fragment thereof, can then be cloned into an appropriate expression vector.

Humanized antibodies in which specific amino acids have been substituted, deleted, or added can also be fused to the scaffold. Preferred humanized antibodies have amino acid substitutions in the framework region, such as to improve binding to an antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR. Criteria for selecting amino acids from the donor are described in U.S. Pat. No. 5,585,089, the contents of which are hereby incorporated by reference. Other techniques for humanizing antibodies are described in Padlan et al. EP 519596 A1.

In one embodiment, each polypeptide of a trimeric antibody does not contain a collagen NC1 domain. In one embodiment, each polypeptide of a trimeric antibody does not contain a disulfide knot. In one embodiment, each polypeptide of a trimeric antibody does not contain a bacteriophage T4 fibritin foldon domain.

Preferably, the scaffold of a trimeric antibody is of a minimal size. In one embodiment, the collagen-like domain comprises the sequence $(G\text{-}P\text{-}P/O)_{10}$ (SEQ ID NO: 21). In one embodiment, each polypeptide comprises less than 13 G-X-Y repeats. In certain embodiments, the trimeric antibody comprises less than 11, 12, 13, 14, 15, 16, 17, 18, 19, 20, 22, 25, 27, 30, 35, 40, 45, or 50 G-X-Y repeats. In certain embodiments, each polypeptide of a trimeric antibody has a molecular weight of less than 35, 37, 39, 40, 41, 42, 43, 44, 45, 46, 47, 48, 49, or 50 kD. In one embodiment, the trimeric soluble antibody has a molecular weight of less than 105, 110, 115, 120, 125, 130, 135, 140, 145, or 150 kD.

In a preferred embodiment, the trimeric soluble antibody comprises three polypeptides, wherein each polypeptide comprises a collagen scaffold domain comprising at least 10 G-X-Y repeats, and wherein at least 5, at least 6, at least 7, at least 8, at least 9, or at least 10 of the Y residues are hydroxyproline; and an antibody domain, wherein the collagen-like domains of the three polypeptides interact with each other to form a trimeric soluble antibody that specifically binds to a ligand with an avidity of at least $10^7$ $M^{-1}$.

The invention also includes a nucleic acid which encodes a fusion polypeptide that forms a protein complex of this invention. The nucleic acid can be screened from phage display library or isolated (e.g., by RT-PCR) from cell lines expressing the above-described suitable antibodies or antibody derivatives. The nucleic acid can be functionally ligated into an expression vector. Cells transformed with the nucleic acid or vector can be used to produce the fusion polypeptide or protein complex of this invention. Cells useful for producing an antibody include insect cells and mammalian cells. These cells include, but are not limited to myeloma NS0 cells, CHO cells, and lymphatic cells.

The invention encompasses methods for generating a trimeric soluble antibody by joining a nucleic acid comprising a collagen scaffold domain with nucleic acid comprising an antibody domain, for example, using conventional molecular techniques. The collagen scaffold domain can be joined directly to the antibody domain or can be separated by additional sequences, such as nucleotide sequences encoding a hinge region. The nucleic acid can be expressed in a cell system that allows for hydroxyprolination, such as NS0 cells.

In one embodiment, the invention encompasses a method for generating a trimeric soluble antibody by joining a nucleic acid encoding a collagen-like domain in-frame with a nucleic acid encoding an antibody domain. In a preferred embodiment, the collagen-like domain comprises more than 10 G-X-Y repeats. In one embodiment, the collagen-like domain comprises 10-30 G-X-Y repeats; wherein G is glycine, X is any amino acid, and Y is any amino acid, and wherein at least 10 of the G-X-Y repeats are G-P-P. In one embodiment, the collagen-like domain is joined in-frame with a nucleic acid encoding an antibody domain for a ligand; and expressing the encoded polypeptide in a cell that hydroxyprolinates at least 5, at least 6, at least 7, at least 8, at least 9, or at least 10 of the G-P-P repeats at the Y position; wherein the hydroxyprolinated collagen-like domains of three polypeptides interact with each other to form a trimeric soluble antibody that specifically binds to the ligand with an avidity of at least $10^7$ $M^{-1}$.

In one embodiment, the soluble trimeric antibody has an avidity for its ligand of greater than $10^7$ $M^{-1}$. In one embodiment, the soluble trimeric antibody has an avidity for its ligand of greater than $10^8$ $M^{-1}$. In one embodiment, the soluble trimeric antibody has an avidity for its ligand of greater than $10^9$ $M^{-1}$. In certain embodiments, the soluble trimeric antibody has an avidity for its ligand between $10^7$ $M^{-1}$ and $10^{10}$ $M^{-1}$, between $10^7$ $M^{-1}$ and $10^9$ $M^{-1}$, between $10^7$ $M^{-1}$ and $10^8$ $M^{-1}$, between $10^8$ $M^{-1}$ and $10^{10}$ $M^{-1}$, between $10^8$ $M^{-1}$ and $10^9$ $M^{-1}$, and between $10^9$ $M^{-1}$ and $10^{11}$ $M^{-1}$.

In one embodiment, the ligand for the trimeric soluble antibody is human epidermal growth factor receptor. In one embodiment, the ligand for the trimeric soluble antibody is human HER2/neu. In one embodiment, the ligand for the trimeric soluble antibody is human CD3. In one embodiment, the ligand for the trimeric soluble antibody is human HER2/neu. In one embodiment, the ligand for the trimeric soluble antibody is human TNF-α.

Scaffold domain proteins and scaffold domain fusion proteins can be expressed from vectors, preferably expression vectors, containing a nucleic acid encoding a polypeptide of the invention. As used herein, the term "vector" refers to a nucleic acid molecule capable of transporting another nucleic acid to which it has been linked and can include a plasmid, cosmid, or viral vector. The vector can be capable of autonomous replication or it can integrate into a host DNA. Viral vectors include, e.g., replication defective retroviruses, adenoviruses, and adeno-associated viruses. Expression of proteins in prokaryotes is most often carried out in *E. coli* with vectors containing constitutive or inducible promoters directing the expression of either fusion or non-fusion proteins.

Fusion vectors can add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase.

Typical fusion expression vectors include pGEX (Pharmacia Biotech Inc; Smith, D. B. and Johnson, K. S. (1988) *Gene* 67: 31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119 128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20: 2111 2118). Such alteration of nucleic acid sequences of the invention can be carried out by standard DNA synthesis techniques.

A host cell can be any prokaryotic or eukaryotic cell. The proteins of the invention can be expressed in bacterial cells (such as *E. coli*), insect cells, yeast, or mammalian cells (such as Chinese hamster ovary cells (CHO) or COS cells (African green monkey kidney cells CV-1 origin SV40 cells; Gluzman (1981) *Cell* 23:175 182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

The invention encompasses a method for inhibiting the biological activity of a ligand comprising incubating a trimeric soluble antibody comprising three polypeptides with a ligand; wherein the binding of the trimeric soluble antibody to the ligand inhibits the biological activity of the ligand. In a preferred embodiment, each polypeptide comprises a collagen scaffold domain comprising at least 10 G-X-Y repeats; wherein G is glycine, X is any amino acid, and Y is any amino acid, wherein at least 10 of the G-X-Y repeats are G-P-P or G-P-O, wherein at least 5, at least 6, at least 7, at least 8, at least 9, or at least 10 of the G-X-Y repeats are G-P-O, and wherein P is proline and O is hydroxyproline; and an antibody domain; wherein the hydroxyprolinated collagen-like domains of three polypeptides interact with each other to form a trimeric soluble antibody that binds to a ligand with an avidity of at least $10^7$ $M^{-1}$.

In one embodiment, the soluble trimeric antibody has an avidity for its ligand of greater than $10^7$ $M^{-1}$. In one embodiment, the soluble trimeric antibody has an avidity for its ligand of greater than $10^8$ $M^{-1}$. In one embodiment, the soluble trimeric antibody has an avidity for its ligand of greater than $10^9$ $M^{-1}$. In certain embodiments, the soluble trimeric antibody has an avidity for its ligand between $10^7$ $M^{-1}$ and $10^{11}$ $M^{-1}$, between $10^7$ $M^{-1}$ and $10^9$ $M^{-1}$, between $10^7$ $M^{-1}$ and $10^8$ $M^{-1}$, between $10^8$ $M^{-1}$ and $10^{10}$ $M^{-1}$, between $10^5$ $M^{-1}$ and $10^9$ $M^{-1}$, and between $10^9$ $M^{-1}$ and $10^{10}$ $M^{-1}$.

In certain embodiments, the ligand for the trimeric soluble antibody is human epidermal growth factor receptor, human HER2/neu, human CD3, human HER2/neu, or human TNF-α.

A protein complex of this invention may be conjugated to a therapeutic moiety such as a cytotoxin, a therapeutic agent, or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, and 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Radioactive ions contemplated in embodiments of the invention include, but are not limited to, $^{111}$Indium, $^{113}$Indium, $^{99}$Rhenium, $^{105}$Rhenium, $^{101}$Rhenium, $^{99}$Mtechnetium, $^{121}$Mtellurium, $^{122}$Mtellurium, $^{125}$Mtellurium, $^{165}$Thulium, 167Thulium, $^{168}$Thulium, $^{123}$Iodine, $^{125}$Iodine, $^{126}$Iodine, $^{131}$Iodine, $^{133}$Iodine, $^{81}$Krypton, $^{33}$Xenon, $^{90}$Yttrium, $^{213}$Bismuth, $^{77}$Bromine, $^{18}$Fluorine, $^{95}$Ruthenium, $^{97}$Ruthenium, $^{103}$Ruthenium, $^{105}$Ruthenium, $^{107}$Mercury, $^{203}$Mercury, $^{67}$Gallium, $^{68}$Gallium, $^{35}$Sulphur, and $^{14}$Carbon.

The conjugates can be used for modifying a given biological response by administering the conjugate to a host. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

In further embodiments of the invention, a scaffold domain fusion protein can be conjugated to a polymer. Such polymers include, but are not limited to polyethylene glycol, polypropylene glycol, and polyoxyethylated polyol.

The above-described protein complexes and conjugates, based on the specificity of the heterologous binding domains, can be used for treating various disorders, including cancers, inflammation diseases, metabolism diseases, fibrosis diseases, and cardiovascular diseases. The invention therefore features a method of treating such a disorder, e.g., by administering to a subject in need thereof an effective amount of a protein complex of the invention to treat the disorder. Subjects to be treated can be identified as having, or being at risk for acquiring, a condition characterized by the disorder. This method can be performed alone or in conjunction with other drugs or therapy.

Because of the multi-specific feature of a protein complex of this invention, one can use it to bridge molecules or cells that are normally are not associated with each other. This feature is particularly useful for cell-based therapies. In one example, one heterologous domain in the protein complex is capable of activating cytotoxic cells (e.g., cytotoxic T cells) by specifically binding to an effector antigen on the cytotoxic cells, while another heterologous domain specifically binds to a target antigen on a pathogen cell or a malignant cell to be destroyed. In this way, the protein complex can treat a disorder caused by the pathogen or malignant cells.

The term "treating" is defined as administration of a composition to a subject with the purpose to cure, alleviate, relieve, remedy, prevent, or ameliorate a disorder, the symptom of the disorder, the disease state secondary to the disorder, or the predisposition toward the disorder. An "effective amount" is an amount of the composition that is capable of producing a medically desirable result, e.g., as described above, in a treated subject.

Activation of the cytotoxic T cell may occur via binding of the CD3 antigen as an effector antigen on the surface of the cytotoxic T cell by a protein complex of the invention. Other lymphoid cell-associated effector antigens include the human CD16 antigen, NKG2D antigen, NKp46 antigen, CD2 antigen, CD28 antigen, CD25 antigen, CD64 antigen, and CD89 antigen. Binding to these effector antigens leads to activation of effector cells such as monocytes, neutrophilic granulocytes, and dendritic cells. These activated cells then exert a cytotoxic or an apoptotic effect on target cells.

The target antigen is an antigen which is uniquely expressed on a target cell associate with a disease condition, but which is not expressed, expressed at a low level, or non-accessible in a healthy condition. Examples of such target antigens associates with malignant cells include EpCAM, CCR5, CD19, HER 2/neu, HER3, HER4, EGFR, PSMA, CEA, MUC-1 (mucin), MUC2, MUC3, MUC4, MUC5.sub.AC, MUC5.sub.B, MUC7, beta-hCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-α precursor, STEAP, mesothelin, A33 Antigen, Prostate Stem Cell Antigen (PSCA), Ly-6, desmoglein 4, E-cadherin neoepitope, Fetal Acetylcholine Receptor, CD25, CA 19-9 marker, CA-125 marker and Muellerian Inhibitory Substance (MIS) Receptor type II, sTn (sialylated Tn antigen; TAC-72), FAP (fibroblast activation antigen), endosialin, EGFRvIII, LG, SAS, and CD63.

In one in vivo approach, a therapeutic composition (e.g., a composition containing a protein complex the invention) is administered to a subject. Generally, the complex is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Suitable dosages are in the range of 0.01-100.0 mg/kg or more specifically 0.1-100, 0.1-75, 0.1-50, 0.1-25, 0.1-10, 0.5-100, 0.5-75, 0.5-50, 0.5-25, 0.5-10, 1-100, 1-75, 1-50, or 1-25 mg/kg. Preferable dosages include 1-10, 10-100, 10-75, 10-50, 10-25, 25-50, 50-75, 25-100, 25-50, 50-100, or 75-100 mg/kg. Most preferably, dosages can range from 1-2, 3-4, 5-6, 7-8, or 9-10 mg/kg. Therapeutic compositions of the invention can be administered daily, one time, two times, or three times or more per week for between about 1 to 10 weeks, preferably between 2 to 8 weeks, more preferably between about 3 to 7 weeks, and even more preferably for about 4, 5, or 6 weeks. Variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

The pharmaceutically acceptable carrier includes a solvent, a dispersion medium, a coating, an antibacterial and antifungal agent, and an isotonic and absorption delaying agent. Specifically, these agents can include saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH of the pharmaceutical composition can be adjusted with acids or bases, such as hydrochloric acid or sodium hydroxide.

Also within the scope of this invention is a pharmaceutical composition that contains a pharmaceutically acceptable carrier and an effective amount of a protein complex of the invention. The pharmaceutical composition can be used to treat the disorders listed above. The pharmaceutically acceptable carrier includes a solvent, a dispersion medium, a coating, an antibacterial and antifungal agent, and an isotonic and absorption delaying agent. The pharmaceutical composition can be formulated into dosage forms for different administration routes utilizing conventional methods.

The efficacy of a composition of this invention can be evaluated both in vitro and in vivo. For in vivo studies, the composition can be injected into an animal (e.g., a mouse model) and its therapeutic effects are then accessed. Based on the results, an appropriate dosage range and administration route can be determined.

As used herein, the terms "directed against" and "specifically binds to" mean that the antibody or fragment of an antibody has an avidity of at least $10^{-6}$ M for its ligand.

In an embodiment of the invention, the first scaffold domain fusion protein is a fusion of the $(GPP)_{10}$ (SEQ ID NO: 20) to an antibody directed against the EGFR. In further embodiment of the invention, the collagen scaffold domain fusion protein is a fusion of the $(GPP)_{10}$ (SEQ ID NO: 20) to a fragment of an antibody directed against the EGFR, wherein the fragment can be, but is not limited to, an scFv, $V_L$, $V_H$, or Fab fragment.

In another embodiment of the invention, the first collagen scaffold domain fusion protein is a fusion of the $(GPP)_{10}$ (SEQ ID NO: 20) to an antibody directed against CD3. In further embodiment of the invention, the collagen scaffold domain fusion protein is a fusion of the $(GPP)_{10}$ (SEQ ID NO: 20) to a fragment of an antibody directed against CD3, wherein the fragment can be, but is not limited to, an scFv, $V_L$, $V_H$, or Fab fragment.

In yet another embodiment of the invention, the first scaffold domain fusion protein is a dual-specific fusion protein of the $(GPP)_{10}$ (SEQ ID NO: 20) with either an antibody or fragment of an antibody against EGFR and an antibody or fusion protein directed against CD3. The antibody or fragment of antibody directed against EGFR can be fused to the N-terminus of the $(GPP)_{10}$ (SEQ ID NO: 20) and the antibody or fragment of an antibody directed against CD3 can be fused to the C-terminus of the $(GPP)_{10}$ (SEQ ID NO: 20). This embodiment includes, but is not limited to the dual-specific collagen scaffold domain fusion protein 763CSAOKT3. In another embodiment of the invention, the antibody or fragment of antibody directed against CD3 can be fused to the N-terminus of the $(GPP)_{10}$ (SEQ ID NO: 20) and the antibody or fragment of an antibody directed against EGFR can be fused to the C-terminus of the $(GPP)_{10}$ (SEQ ID NO: 20).

In yet other embodiments of the invention, a first collagen scaffold domain fusion protein is a fusion between $(GPP)_{10}$ (SEQ ID NO: 20) and an antibody or a fragment of an antibody directed against EGFR, wherein the antibody or fragment of antibody is fused to either the N-terminus or C-terminus of the $(GPP)_{10}$ (SEQ ID NO: 20). A second scollagen caffold domain fusion protein can be a fusion between $(GPP)_{10}$ (SEQ ID NO: 20) and an antibody or a fragment of an antibody directed against CD3, wherein the antibody or fragment of antibody is fused to either the N-terminus or C-terminus of the $(GPP)_{10}$ (SEQ ID NO: 20).

In an embodiment of the invention, the anti-EGFR scFv collagen scaffold domain protein is 763_scFv-Col.

In an embodiment of the invention, the anti-CD3 scFv collagen scaffold domain fusion protein is OKT3_scFv-Col.

In another embodiment of the invention, the first collagen scaffold domain fusion protein is a fusion of the $(GPP)_{10}$ (SEQ ID NO: 20) to an antibody directed against TNF-α. In a further embodiment of the invention, the collagen scaffold domain fusion protein is a fusion of the $(GPP)_{10}$ (SEQ ID NO: 20) to a fragment of an antibody directed against the TNF-α, wherein the fragment can be, but is not limited to, an scFv, $V_L$, $V_H$, or Fab fragment.

In an embodiment of the invention, the anti-TNF-α scFv collagen scaffold domain fusion protein is 357_scFv-Col.

In yet another embodiment of the invention, the first collagen scaffold domain fusion protein is a dual-specific fusion protein of the $(GPP)_{10}$ (SEQ ID NO: 20) with both an antibody or fragment of an antibody directed against TNF-α, EGFR and an antibody or fusion protein directed against CD3. The antibody or fragment of antibody directed against TNF-α, EGFR can be fused to the N-terminus of the $(GPP)_{10}$ SEQ ID NO: 20) and the antibody or fragment of an antibody directed against CD3 can be fused to the C-terminus of the $(GPP)_{10}$ (SEQ ID NO: 20). In another embodiment of the invention, the antibody or fragment of antibody directed against CD3 can be fused to the N-terminus of the $(GPP)_{10}$ (SEQ ID NO: 20) and the antibody or fragment of an antibody directed against TNF-α, EGFR can be fused to the C-terminus of the $(GPP)_{10}$ (SEQ ID NO: 20).

In yet other embodiments of the invention, a first collagen scaffold domain fusion protein is a fusion between $(GPP)_{10}$ (SEQ ID NO: 20) and an antibody or a fragment of an antibody directed against TNF-α, wherein the antibody or fragment of antibody is fused to either the N-terminus or C-terminus of the $(GPP)_{10}$ (SEQ ID NO: 20). A second scaffold domain fusion protein can be a fusion between $(GPP)_{10}$ (SEQ ID NO: 20) and an antibody or a fragment of an antibody directed against CD3, wherein the antibody or fragment of antibody is fused to either the N-terminus or C-terminus of the $(GPP)_{10}$ (SEQ ID NO: 20).

In yet another embodiment of the invention, the first collagen scaffold domain fusion protein is a dual-specific fusion protein of the $(GPP)_{10}$ (SEQ ID NO: 20) with both an antibody and fragment of an antibody against EGFR and an antibody or fusion protein directed against CD3. The antibody or fragment of antibody directed against EGFR can be fused to the N-terminus of the $(GPP)_{10}$ (SEQ ID NO: 20) and the antibody or fragment of an antibody directed against CD3 can be fused to the C-terminus of the $(GPP)_{10}$ (SEQ ID NO: 20). In another embodiment of the invention, the antibody or fragment of antibody directed against CD3 can be fused to the N-terminus of the $(GPP)_{10}$ (SEQ ID NO: 20) and the antibody or fragment of an antibody directed against EGFR can be fused to the C-terminus of the $(GPP)_{10}$ (SEQ ID NO: 20).

In yet other embodiments of the invention, a first collagen scaffold domain fusion protein is a fusion between $(GPP)_{10}$ (SEQ ID NO: 20) and an antibody or a fragment of an antibody directed against EGFR, wherein the antibody or fragment of antibody is fused to either the N-terminus or C-terminus of the $(GPP)_{10}$ (SEQ ID NO: 20). A second collagen scaffold domain fusion protein can be a fusion between $(GPP)_{10}$ (SEQ ID NO: 20) and an antibody or a fragment of an antibody directed against CD3, wherein the antibody or fragment of antibody is fused to either the N-terminus or C-terminus of the $(GPP)_{10}$ (SEQ ID NO: 20).

In further embodiments of the invention, a collagen scaffold domain fusion protein can include fusion to a marker protein. Marker proteins include, but are not limited to, luciferase, green fluorescent protein, and enhanced green fluorescent protein. These embodiments include, but are not limited to, the collagen scaffold domain fusion proteins h4D5CSA-Luc, which is directed to HER2/neu.

Collagen scaffold domain fusion proteins that include marker proteins can be used in diagnostic and molecular imaging. In embodiments of the invention, collagen scaffold domain fusion proteins that include marker proteins or radioactive ions, or other fusion moieties, can be packaged in a kit including the scaffold domain fusion protein and other reagents necessary for imaging of specific molecules. These reagents can include, but are not limited to, reagents for the preparation of biological samples and reagents for the visualization of the marker protein.

The invention encompasses a method for detecting a ligand comprising incubating a trimeric soluble antibody comprising three polypeptides with the ligand and detecting the binding of the trimeric soluble antibody to the ligand. In a preferred embodiment, each polypeptide comprises a collagen scaffold domain comprising at least 10 G-X-Y repeats; wherein G is glycine, X is any amino acid, and Y is any amino acid, wherein at least 10 of the G-X-Y repeats are G-P-P or G-P-O, wherein at least 5, at least 6, at least 7, at least 8, at least 9, or at least 10 of the G-X-Y repeats are G-P-O, and wherein P is proline and O is hydroxyproline; and an antibody domain; wherein the hydroxyprolinated collagen-like domains of three polypeptides interact with each other to form a trimeric soluble antibody that binds to a ligand with an avidity of at least $10^7$ $M^-$. In a preferred embodiment, each polypeptide comprises a collagen scaffold domain comprising at least 10 G-X-Y repeats; wherein G is glycine, X is any amino acid, and Y is any amino acid, wherein at least 5, at least 6, at least 7, at least 8, at least 9, or at least 10 of the G-X-Y repeats are G-X-O, wherein O is hydroxyproline; and an antibody domain; wherein the hydroxyprolinated collagen scaffold domains of three polypeptides interact with each other to form a trimeric soluble antibody that binds to a ligand with an avidity of at least $10^7$ $M^{-1}$.

In one embodiment, the soluble trimeric antibody has an avidity for its ligand of greater than $10^7$ $M^{-1}$. In one embodiment, the soluble trimeric antibody has an avidity for its ligand of greater than $10^8$ $M^{-1}$. In one embodiment, the soluble trimeric antibody has an avidity for its ligand of greater than $10^9$ $M^{-1}$. In certain embodiments, the soluble trimeric antibody has an avidity for its ligand between $10^7$ $M^{-1}$ and $10^{10}$ $M^{-1}$, between $10^7$ $M^{-1}$ and $10^9$ $M^{-1}$, between $10^7$ $M^{-1}$ and $10^8$ $M^{-1}$, between $10^8$ $M^{-1}$ and $10^{10}$ $M^{-1}$, between $10^8$ $M^{-1}$ and $10^9$ $M^{-1}$, and between $10^9$ $M^{-1}$ and $10^{10}$ $M^{-1}$.

In certain embodiments, the trimeric soluble antibody comprises a luciferase polypeptide.

Embodiments of the invention include a recombinant protein complex comprising a first fusion polypeptide chain containing a first collagen scaffold domain and a first heterologous domain fused to one end of the first scaffold domain; a second fusion polypeptide chain containing a second collagen scaffold domain; and a third fusion polypeptide chain containing a third scaffold domain; wherein the first, second, and third scaffold domains are aligned to form a triple helix coil.

In further embodiments, the invention provides for a protein complex wherein the first fusion polypeptide chain further contains a second heterologous domain fused to the other end of the first collagen scaffold domain. Other embodiments of the invention included protein complex wherein the first heterologous domain contains the sequence of a first single-chain antibody that specifically binds to CD3 or a second heterologous domain that contains the sequence of a second single-chain antibody that specifically binds EGFR.

In further embodiments of the invention, the protein complex includes a second fusion polypeptide chain comprising a third heterologous domain fused to one end of the second scaffold domain, and a second fusion polypeptide chain comprising a fourth heterologous domain fused to the other end of the second scaffold domain, a third fusion polypeptide chain contains a fifth heterologous domain fused to one end of the third scaffold domain and a sixth heterologous domain fused to the other end of the third scaffold domain, wherein each repeat contains a sequence of $(GPP)_{10}$ (SEQ ID NO: 20).

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Selection of Phage Library for Anti-EGFR Antibody Domain

An erb phagemid containing an epidermal growth factor receptor extracellular domain (EGFR-ECD)-binding variable fragment (scFv) was isolated by screening a human single fold scFv phage display libraries (Tomlinson I+J; kindly provided by I. M. Tomlinson and G. Winter, MRC Laboratory of Molecular Biology, Cambridge, UK). Selections were performed using immunotubes (Maxisorp; Nunc, Roskilde, Denmark) coated with 10 μg of purified recombinant extracellular domain of EGF receptor (EGFR-ECD; Research Diagnostics, Inc.). Blocking, panning, washing, elution, and reamplification of eluted phage were carried out according to the manufacturer's protocol. A numbers of clones were identified. After confirmation by Western Blotting and ELISA, one clone, erb_scFv, was selected for further experiment. The cDNA encoding erb_scFv was obtained and ligated into an expression vector by a standard method. Listed below are the polypeptide sequence of erb_scFv (SEQ ID NO:1) and the nucleotide sequence encoding it (SEQ ID NO:2).

```
                                          SEQ ID NO: 1
MetAlaGluValGlnLeuLeuGluSerGlyGlyGlyLeuValGlnPro

GlyGlySerLeuArgLeuSerCysAlaAlaSerGlyPheThrPheSer

SerTyrAlaMetSerTrpValArgGlnAlaProGlyLysGlyLeuGlu

TrpValSerAspIleGlyAlaSerGlySerAlaThrSerTyrAlaAsp

SerValLysGlyArgPheThrIleSerArgAspAsnSerLysAsnThr

LeuTyrLeuGlnMetAsnSerLeuArgAlaGluAspThrAlaValTyr

TyrCysAlaLysSerThrThrThrPheAspTyrTrpGlyGlnGlyThr

LeuValThrValserSerGlyGlyGlyGlySerGlyGlyGlyGlySer

GlyGlyGlyGlySerThrAspIleGlnMetThrGlnSerProSerSer

LeuSerAlaSerValGlyAspArgValThrIleThrCysArgAlaSer

GlnSerIleSerSerTyrLeuAsnTrpTyrGlnGlnLysProGlyLys
```

-continued

```
AlaProLysLeuLeuIleTyrAspAlaSerAlaLeuGlnSerGlyVal

ProSerArgPheSerGlySerGlySerGlyThrAspPheThrLeuThr

IleSerSerLeuGlnProGluAspPheAlaThrTyrTyrCysGlnGln

TyrAlaAspTyrProThrThrPheGlyGlnGlyThrLysValGluIle

LysArg
```

```
                                          SEQ ID NO: 2
ATGGCCGAGGTGCAGCTGTTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAGATATTGGTGCTTCTGGTTCTGCTACATCTTACGCAGACTCCGTGAA

GGGCCGGTTCACCATCTCCAGAGACAATTCCAAGAACACGCTGTATCTGC

AAATGAACAGCCTGAGAGCCGAGGACACGGCCGTATATTACTGTGCGAAA

TCTACTACTACTTTTGACTACTGGGGCCAGGGAACCCTGGTCACCGTCTC

GAGCGGTGGAGGCGGTTCAGGCGGAGGTGGCAGCGGCGGTGGCGGGTCGA

CGGACATCCAGATGACCCAGTCTCCATCCTCCCTGTCTGCATCTGTAGGA

GACAGAGTCACCATCACTTGCCGGGCAAGTCAGAGCATTAGCAGCTATTT

AAATTGGTATCAGCAGAAACCAGGGAAAGCCCCTAAGCTCCTGATCTATG

ATGCATCCGCTTTGCAAAGTGGGGTCCCATCAAGGTTCAGTGGCAGTGGA

TCTGGGACAGATTTCACTCTCACCATCAGCAGTCTGCAACCTGAAGATTT

TGCAACTTACTACTGTCAACAGTATGCTGATTATCCTACTACGTTCGGCC

AAGGGACCAAGGTGGAAATCAAACGG
```

The expression vector was then expressed in insect cell line *Drosophila* S2. The anti-EGFR erb_scFv was purified and subjected to Western Blot analysis and ELISA to confirm its specificity against EGFR.

Example 2

CD3 Antibody Domain

RT-PCR was conducted to obtain from hybridoma cell lines cDNAs encoding the heavy chain variable region ($V_H$) and light chain variable region ($V_L$) of anti-CD3 monoclonal antibody OKT3. Then, the two cDNAs were ligated to generate a fusion sequence that encodes a fusion protein of $V_H$-$V_L$ of OKT3. Listed below are the polypeptide sequence of this fusion protein (SEQ ID NO: 3) and the cDNA sequence encoding it (SEQ ID NO: 4).

```
                                          SEQ ID NO: 3
ValGlnLeuGlnGlnSerGlyAlaGluLeuAlaArgProGlyAlaSer

ValLysMetSerCysLysAlaSerGlyTyrThrPheThrArgTyrThr

MetHisTrpValLysGlnArgProGlyGlnGlyLeuGluTrpIleGly

TyrIleAsnProSerArgGlyTyrThrAsnTyrAsnGlnLysPheLys

AspLysAlaThrLeuThrThrAspLysSerSerSerThrAlaTyrMet

GlnLeUSerSerLeuThrSerGluAspSerAlaValTyrTyrCysAla

ArgTyrTyrAspAspHisTyrCysLeuAspTyrTrpGlyGlnGlyThr

ThrValThrValSerSerGlyGlyGlyGlySerGlyGlyGlyGlySer

GlyGlyGlyGlySerAspIleValLeuThrGlnSerProAlaIleMet
```

-continued

```
SerAlaSerProGlyGluLysValThrMetThrCysSerAlaSerSer

SerValSerTyrMetAsnTrpTyrGlnGlnLysSerGlyThrSerPro

LysArgTrpIleTyrAspThrSerLysLeuAlaSerGlyValProAla

HisPheArgGlySerGlySerGlyThrSerTyrSerLeuThrIleSer

GlyMetGluAlaGluAspAlaAlaThrTyrTyrCysGlnGlnTrpSer

SerAsnProPheThrPheGlySerGlyThrLysLeuGluLeuLysArg
```

SEQ ID NO: 4

```
GTCCAGCTGCAGCAGTCAGGGGCTGAACTGGCAAGACCTGGGGCCTCAGT

GAAGATGTCCTGCAAGGCTTCTGGCTACACCTTTACTAGGTACACGATGC

ACTGGGTAAAACAGAGGCCTGGACAGGGTCTGGAATGGATTGGATACATT

AATCCTAGCCGTGGTTATACTAATTACAATCAGAAGTTCAAGGACAAGGC

CACATTGACTACAGACAAATCCTCCAGCACAGCCTACATGCAACTGAGCA

GCCTGACATCTGAGGACTCTGCAGTCTATTACTGTGCAAGATATTATGAT

GATCATTACTGCCTTGACTACTGGGGCCAAGGGACCACGGTCACCGTCTC

CTCAGGTGGAGGCGGTTCAGGCGGAGGTGGCTCTGGCGGTGGCGGATCGG

ACATTGTGCTAACCCAGTCTCCAGCAATCATGTCTGCATCTCCAGGGGAG

AAGGTCACCATGACCTGCAGTGCCAGCTCAAGTGTAAGTTACATGAACTG

GTACCAGCAGAAGTCAGGCACCTCCCCCAAAAGATGGATTTATGACACAT

CCAAACTGGCTTCTGGAGTCCCTGCTCACTTCACCGGCAGTGGGTCTGGG

ACCTCTTACTCTCTCACAATCAGCGGCATGGAGGCTGAAGATGCTGCCAC

TTATTACTGCCAGCAGTGGAGTAGTAACCCATTCACGTTCGGCTCGGGGA

CCAAGCTGGAGCTGAAACGA
```

Example 3

EGFR Antibody Domain

The same procedures were performed to obtain cDNAs encoding $V_H$ and $V_L$ of anti-EGFR monoclonal antibody 528 and a fusion sequence that encodes a fusion protein of $V_H$-$V_L$ of the anti-EGFR 528. The 528 monoclonal antibody binds to EGFR on cellular membranes, e.g., on human epidermoid carcinoma A431 cells. The polypeptide sequence of this 528 single-chain antibody (SEQ ID NO: 5) and the cDNA sequence encoding it (SEQ ID NO: 6) are listed below.

SEQ ID NO: 5

```
ValLysLeuGlnGluSerGlySerGluMetAlaArgProGlyAlaSer

ValLysLeuProCysLysAlaSerGlyAspThrPheThrSerTyrTrp

MetHisTrpValLysGlnArgHisGlyHisGlyProGluTrpIleGly

AsnIleTyrProGlySerGlyGlyThrAsnTyrAlaGluLysPheLys

AsnLysValThrLeuThrValAspArgSerSerArgThrValTyrMet

HisLeuSerArgLeuThrSerGluAspPheAlaValTyrTyrCysThr

ArgSerGlyGlyProTyrPhePheAspTyrTrpGlyGlnGlyThrThr

ValThrValSerSerGlyGlyGlyGlySerGlyGlyGlyGlySerGly

GlyGlyGlySerMetThrGlnThrProLeuSerLeuProValSerLeu
```

-continued

```
GlyAspGlnAlaSerIleSerCysArgSerSerGlnAsnIleValHis

AsnAsnGlyIleThrTyrLeuGluTrpTyrLeuGlnArgProGlyGln

SerProLysLeuLeuIleTyrLysValSerAspArgPheSerGlyVal

ProAspArgPheSerGlySerGlySerGlyThrAspPheThrLeuLys

IleSerArgValGluAlaGluAspLeuGlyIleTyrTyrCysPheGln

GlySerHisHisProProThrPheGlyGlyGlyThrLysLeuGlu
```

SEQ ID NO: 6

```
GTCAAGCTGCAGGAGTCAGGGTCTGAGATGGCGAGGCCTGGAGCTTCAGT

GAAGCTGCCCTGCAAGGCTTCTGGCGACACATTCACCAGTTACTGGATGC

ACTGGGTGAAGCAGAGGCATGGACATGGCCCTGAGTGGATCGGAAATATT

TATCCAGGTAGTGGTGGTACTAACTACGCTGAGAAGTTCAAGAACAAGGT

CACTCTGACTGTAGACAGGTCCTCCCGCACAGTCTACATGCACCTCAGCA

GGCTGACATCTGAGGACTTTGCGGTCTATTATTGTACAAGATCGGGGGGT

CCCTACTTCTTTGACTACTGGGGCCAAGGGACCACGGTCACCGTCTCCTC

AGGTGGAGGCGGTTCAGGCGGAGGTGGCTCTGGCGGTGGCGGATCGATGA

CCCAAACTCCACTCTCCCTGCCTGTCAGTCTTGGAGATCAAGCCTCCATC

TCTTGCAGATCTAGTCAGAACATTGTACATAATAATGGAATCACCTATTT

AGAATGGTACCTGCAAAGGCCAGGCCAGTCTCCAAAGCTCCTGATCTACA

AAGTTTCCGACCGATTTTCTGGGGTCCCAGACAGGTTCAGTGGCAGTGGA

TCAGGGACAGATTTCACACTCAAGATCAGCAGAGTAGAGGCTGAGGATCT

GGGAATTTATTACTGCTTTCAAGGTTCACATCATCCTCCCACGTTCGGCG

GGGGGACCAAGCTGGAA
```

Example 4

Fusion of Antibody Domains to Human Minicollagen XXI

The cDNAs encoding the above-described anti-EGFR erb, OKT3 $V_H$-$V_L$, and anti-EGFR 528$V_H$-$V_L$ were respectively fused in-frame to the human minicollagen) XXI cDNA containing a hinge region of human IgG, EPKSCDKTHTCPPCPRSIP (SEQ ID NO: 28), at the 5' end and a histidine tag sequence at the 3' end. Shown below are the scaffold domain of human minicollagen XXI polypeptide and cDNA sequences (SEQ ID NO: 7 and 8, respectively).

SEQ ID NO: 7:

```
GlyGlyArgGluProLysSerCysAspLysThrHisThrCysProPro

CysProArgSerIleProGlyProProGlyProIleGlyProGluGly

ProArgGlyLeuProGlyLeuProGlyArgAspGlyValProGlyLeu

ValGlyValProGlyArgProGlyValArgGlyLeuLysGlyLeuPro

GlyArgAsnGlyGluLysGlySerGlnGlyPheGlyTyrProGlyGlu

GlnGlyProProGlyProProGlyProGluGlyProProGlyIleSer

LysGluGlyProProGlyAspProGlyLeuProGlyLysAspGlyAsp

HisGlyLysProGlyIleGlnGlyGlnProGlyProProGlyIleCys
```

-continued

```
AspProSerLeuCysPheSerValIleAlaArgArgAspProPheArg

LysGlyProAsnTyrSer

(note: Pro = Proline or Hydroxyproline)

SEQ ID NO: 8:
GGCGGCCGCGAGCCCAAATCTTGTGACAAAACTCACACATGCCCACCGTG

CCCAAGATCTATTCCTGGGCCACCTGGTCCGATAGGCCCAGAGGGTCCCA

GAGGATTACCTGGTTTGCCAGGAAGAGATGGTGTTCCTGGATTAGTGGGT

GTCCCTGGACGTCCAGGTGTCAGAGGATTAAAAGGCCTACCAGGAAGAAA

TGGGGAAAAAGGGAGCCAAGGGTTTGGGTATCCTGGAGAACAAGGTCCTC

CTGGTCCCCCAGGTCCAGAGGGCCCTCCTGGAATAAGCAAAGAAGGTCCT

CCAGGAGACCCAGGTCTCCCTGGCAAAGATGGAGACCATGGAAAACCTGG

AATCCAAGGGCAACCAGGCCCCCCAGGCATCTGCGACCCATCACTATGTT

TTAGTGTAATTGCCAGAAGAGATCCGTTCAGAAAAGGACCAAACTATAGT
```

OKT3mC21fd containing an amino-terminal anti-CD3 scFv derived from OKT3 IgG, a hinge region of human IgG, a human minicollagen XXI polypeptide, followed by a T4 fibritin foldon domain and a histidine tag was constructed. The bacteriophage T4 fibritin foldon domain, which consists of 27 amino acids, NH2-GYIPEAPRDGQAYVRKDGEV-VVLLSTFL-COOH (SEQ ID NO: 29), and forms a β-propeller-like structure with a hydrophobic interior, was sufficient to drive the trimerization and correct folding of the collagen domain (Frank et al., (2001) *J Mol Biol* 308: 1081-1089).

Figure 2:
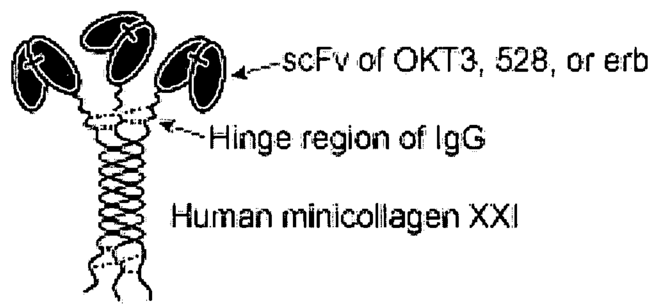
FIGS. 2A and 2B are respectively (A) a schematic representation of a trimeric collagen scaffold antibody (CSA) that contains an amino-terminal scFv derived from OKT3 (anti-CD3), 528 (anti-EGFR), or erb (anti-EGFR), which are respectively fused in-frame to a hinge region of human IgG, a collagen scaffold domain of human type XXI minicollagen, followed by a histidine tag. Dashed lines: interchain disulfide-bonds; and (B) a depiction of Western blotting results of the protein complex. OKT3mC21 contains an amino-terminal anti-CD3 scFv derived from OKT3 IgG, a hinge region of human IgG, a human minicollagen XXI polypeptide, followed by a histidine tag; OKT3mC21fd contains an amino-terminal anti-CD3 scFv derived from OKT3 IgG, a hinge region of human IgG, a human minicollagen XXI polypeptide, followed by a T4 fibritin foldon domain and a histidine tag. The culture media from the stably transfected *Drosophila* S2 cells was electrophoresed on a SDS-PAGE under non-reducing conditions and then immunoblotted with a monoclonal antibody to the C-terminal of type XXI collagen, 3E2. T: interchain disulfide-bonded trimers; Mt: monomers containing intrachain disulfide-bonded trimers.
Figure 2:
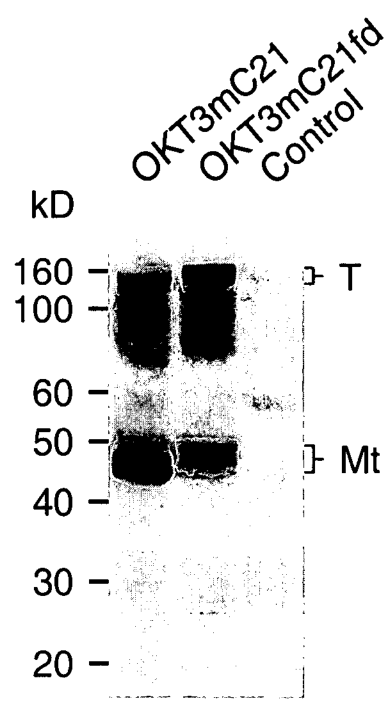
Figure 3:
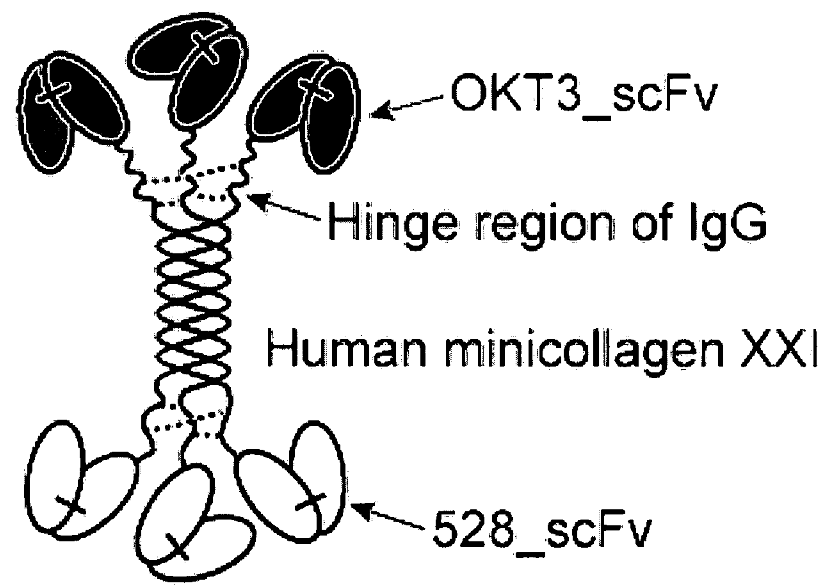
FIG. 3 is a diagram showing a bispecific trimeric CSA, containing an amino-terminal OKT3 single-chain antibody (OKT3_scFv), a hinge region of human IgG, a collagen scaffold domain of human type XXI minicollagen, followed by a C-terminal 528 single-chain antibody (528_scFv).

The resulting expression vectors for both OKT3mC21 and OKT3mC21fd were transfected into *Drosophila* S2 cells carrying a stably expressed human prolyl 4-hydroxylase genes, respectively. The cells were cultured in the presence blasticidin to select blasticidin-resistant cells. Cell culture supernatants were collected and analyzed by Western blotting with monoclonal antibody 3E2, which recognizes the C-terminal NC1 domain of α1(XXI) collagen. As shown in FIG. 2, it was found that both OKT3mC21 and OKT3mC21fd formed a trimeric structure (indicated as T) under non-reducing conditions. Intrachain disulfide-bonded trimer (indicated as Mt) was also detected in both OKT3mC21 and OKT3mC21fd. The results demonstrate that the heterologous fusion protein of OKT3_scFv does not affect the trimerization property of the scaffold domain of minicollagen XXI, even without any trimerizing structure such as the T4 foldon domain.

Example 5

Fusion of Antibody Domains to a Collagen-Like Domain

The collagenous domain of minicollagen XXI was substituted with a thermally stable short collagen-like peptide $(Gly\text{-}Pro\text{-}Pro)_{10}$ (SEQ ID NO: 20) as a scaffold template for the CSAs. Eight fusion polypeptides: erb_scFv-Col, OKT3_scFv-Col, 763_scFv-Col, 357_scFv-Col, erb_scFv-$GPP_{10}$, Col-erb_scFv, 763CSA-OKT3, and h4D5CSA-Luc were generated. Another collagen-like peptide, $(GPP)_5$GK-PGKP$(GPP)_6$ (SEQ ID NO: 26)), was used as trimerizing scaffold for the construction of 763_CSA2. These scaffold domain fusion proteins were stably expressed as soluble secretory proteins in mouse myeloma NS0 cells.

Construction of Recombinant Plasmids

The cDNA coding for the scFv of erb was PCR amplified from the erb phagemid. A sequence encoding murine IgG2a anti-CD3 mAb OKT3 (Ortho Pharmaceutical Corporation) was obtained by reverse transcription product from OKT3 hybridoma (ATCC, CRL-8001). The cDNAs for the $V_H$ and $V_L$ of the OKT3 mAb were obtained by RT-PCR based on the published nucleotide sequence. The scFv PCR fusion of erb and OKT3 were generated by joining the $V_H$ and $V_L$ chains with a glycine-linker $(GGGGS)_3$ (SEQ ID NO: 30).

The cDNAs coding for the $V_L$ and $V_H$ of mAb 763 were PCR amplified using primer sets derived from the cDNAs of panitumumab (Vectibix, Amgen, Inc) based on the published nucleotide sequence (U.S. Pat. No. 6,235,883). The scFv PCR fusion of 763 was generated by joining the $V_L$ and $V_H$ chains with a glycine-linker $(GGGGS)_3$ (SEQ ID NO: 30).

RT-PCR was conducted to obtain cDNAs encoding the light chain variable region ($V_L$) and heavy chain variable region ($V_H$) of an anti-TNF-α monoclonal antibody 357, derived from the hybridoma 357-101-4 cell line (ECACC No. 92030603), a mouse anti-human TNF-α mAb with strong neutralizing activities. Then, the two cDNAs were joined with a glycine-linker $(GGGGS)_3$ (SEQ ID NO: 30) (italics) to generate a fusion sequence that encodes a fusion protein of 357 scFv. Listed below are the polypeptide sequence of this fusion protein (SEQ ID NO: 9) and the cDNA sequence encoding it (SEQ ID NO: 10).

SEQ ID NO: 9

GluIleValLeuThrGlnSerProProIleMetSerAlaSerProGly

GluLysValThrMetThrCysSerAlaSerSerSerValSerPheMet

TyrTrpTyrGlnGlnLysProGlySerSerProArgLeuLeuIleTyr

AspAlaSerIleLeuAlaSerGlyValProValArgPheSerGlySer

GlySerGlyThrSerTyrSerLeuThrIleSerArgMetGluAlaGlu

AspValAlaThrTyrTyrCysGlnGlnTrpSerAspTyrSerProArg

ThrPheGlyGlyGlyThrLysLeuGluIle*GlyGlyGlyGlySerGly*

*GlyGlyGlySerGlyGlyGlyGlySer*ValLysLeuGlnGluSerGly

GlyGlyTrpValGlnProGlyGlySerMetLysLeuSerCysIleAla

SerGlyPheThrPheSerAsnTyrTrpMetAsnTrpValArgGlnSer

ProGluLysGlyLeuGluTrpValAlaGluValArgLeuGlnSerAsp

AsnPheThrThrHisTyrAlaGluSerValLysGlyArgPheThrIle

SerArgAspAspSerLysSerGlyValTyrLeuGlnMetAsnAsnLeu

GlyAlaGluAspThrGlyIleTyrTyrCysThrProPheAlaTyrTrp

GlyGlnGlyThrThrValThrValSerSer

```
SEQ ID NO: 10
GAAATTGTGCTGACCCAGTCTCCACCGATCATGTCTGCTTCTCCAGGGGA

GAAGGTCACCATGACCTGCAGTGCCAGCTCAAGTGTAAGTTTCATGTACT

GGTACCAGCAGAAGCCAGGATCCTCCCCCAGACTCCTGATTTATGACGCA

TCCATCCTGGCTTCTGGAGTCCCTGTTCGCTTCAGTGGCAGTGGGTCTGG

GACCTCTTACTCTCTCACAATCAGCCGAATGGAGGCTGAAGATGTTGCCA

CTTATTACTGCCAACAATGGAGTGATTACTCACCCAGGACGTTCGGTGGA

GGCACCAAGCTGGAAATTGGGGGAGGCGGTTCAGGCGGAGGTGGCTCTGG

CGGTGGCGGATCGGTGAAACTGCAGGAGTCTGGAGGAGGCTGGGTGCAAC

CTGGAGGATCCATGAAACTCTCCTGTATTGCCTCTGGATTCACTTTCAGT
```

-continued

AACTACTGGATGAACTGGGTCCGCCAGTCTCCAGAGAAGGGGCTTGAGTG

GGTTGCTGAAGTTAGATTGCAATCTGATAATTTTACAACACATTATGCGG

AGTCTGTGAAAGGGAGGTTCACCATCTCAAGAGATGATTCCAAAAGTGGT

GTCTACCTGCAAATGAACAACTTAGGAGCTGAAGACACTGGCATTTATTA

TTGTACCCCGTTTGCTTATTGGGGCCAAGGGACCACGGTCACCGTCTCCT

CA

To generate scFv-Col, the coding region of scFv-Col included an N-terminal scFv nucleotide sequence and a C-terminal gene coding for a peptide sequence of EPKSCDKTHTCPPCPRSIP$(GPP)_{10}$GICDPSLCFSVIARRDPFRKGPNY (SEQ ID NO: 11), which includes a hinge region of human IgG (italics), a collagen-like scaffold domain (in boldface), and the NC1 domain of type XXI collagen. Shown below are the synthetic collagen scaffold-containing polypeptide and cDNA sequences (SEQ ID NOs: 11 and 12, respectively).

SEQ ID NO: 11:
GluProLysSerCysAspLysThrHisThrCysProProCysProArg

SerIleProGlyProProGlyProProGlyProProGlyProProGly

ProProGlyProProGlyProProGlyProProGlyProProGlyPro

ProGlyIleCysAspProSerLeuCysPheSerValIleAlaArgArg

AspProPheArgLysGlyProAsnTyr

SEQ ID NO: 12:
GAGCCCAAATCTTGTGACAAAACTCACACATGCCCACCGTGCCCAAGATC

TATTCCTGGGCCACCTGGTCCCCCAGGTCCTCCAGGACCCCCAGGGCCCC

CAGGCCCCCCCGGGCCGCCTGGACCCCCAGGGCCACCAGGCCCCCCAGGC

ATCTGCGACCCATCACTATGTTTTAGTGTAATTGCCAGAAGAGATCCGTT

CAGAAAAGGACCAAACTAT

This synthetic sequence (SEQ ID NO: 12) was prepared by overlapping PCR and the PCR product flanking with NotI and XhoI sites was cloned into the expression vector pSecTag2/Hygro (Invitrogen) at the same sites. The scFvs of erb, OKT3, 763 and 357 were then cloned in-frame to the above C-terminal collagen scaffold-containing construct at AscI and NotI sites to make the expression constructs of erb_scFv-Col, OKT3_scFv-Col, 763_scFv-Col and 357_scFv-Col, respectively.

Next, erb_scFv-$GPP_{10}$ was generated to demonstrate that the collagen-scaffold peptide of the CSA, $(GPP)_{10}$ (SEQ ID NO: 20), by itself can drive the formation of a non-covalently bound trimeric fusion protein, without the aid of interchain crosslinking amino acid residues (such as Cys and Lys) present within or flanking the collagen-like domain. The coding region of erb_scFv-$GPP_{10}$ included an N-terminal nucleotide sequence of erb_scFv and a C-terminal synthetic gene coding for a peptide sequence of GSP$(GPP)_{10}$GPSSGG (SEQ ID NO: 31), which includes a collagen-like scaffold domain (in boldface). Shown below are the synthetic collagen scaffold-containing polypeptide and cDNA sequence (SEQ ID NOs: 13 and 14, respectively).

SEQ ID NO: 13:
GlySerProGlyProProGlyProProGlyProProGlyProProGly

ProProGlyProProGlyProProGlyProProGlyProProGlyPro

ProGlyProSerSerGlyGly (note: Pro = Proline or Hydroxyproline)

SEQ ID NO: 14:
GGCAGCCCTGGGCCACCTGGTCCCCCAGGTCCTCCAGGACCCCCAGGGCC

CCCAGGCCCCCCCGGGCCGCCTGGACCCCCAGGGCCACCAGGCCCCCCAG

GCCCTTCCTCTGGCGGA

The cDNA of erb_scFv was cloned in-frame to the above C-terminal collagen scaffold sequence by overlapping PCR and the PCR product flanking with AscI and AgeI sites was cloned into the expression vector pSecTag2/Hygro (Invitrogen) to make the expression construct of erb_scFv-$GPP_{10}$ (SEQ ID NO: 20).

Next, Col-erb_scFv was made. The collagen scaffold region of Col-erb_scFv contains a peptide sequence of TCPPCPRSIP $(GPP)_{10}$ GICDPSLC SEQ ID NO: 32), which includes a collagen-like domain $(GPP)_{10}$ (SEQ ID NO: 20) flanking with two disulfide knots, TCPPCPRSIP (SEQ ID NO: 24) and GICDPSLC (SEQ ID NO: 25). Shown below are the synthetic collagen scaffold-containing polypeptide and cDNA sequence (SEQ ID NOs: 15 and 16, respectively).

SEQ ID NO: 15:
ThrCysProProCysProArgSerIleProGlyProProGlyProPro

GlyProProGlyProProGlyProProGlyProProGlyProProGly

ProProGlyProProGlyProProGlyIleCysAspProSerLeuCys (note: Pro = Proline or Hydroxyproline)

SEQ ID NO: 16:
ACATGCCCACCGTGCCCAAGATCTATTCCTGGGCCACCTGGTCCCCCAG

GTCCTCCAGGACCCCCAGGGCCCCCAGGCCCCCCCGGGCCGCCTGGACC

CCCAGGGCCACCAGGCCCCCCAGGCATCTGCGACCCATCACTATGT

The cDNA of erb_scFv was cloned in-frame to the above N-terminal collagen scaffold sequence (SEQ ID NO: 16) by overlapping PCR and the PCR product flanking with BamHI and AgeI sites was cloned into the expression vector pSecTag2/Hygro (Invitrogen) to make the expression construct of Col-erb_scFv.

Next 763CSA2 was made. The coding region of 763CSA2 included an amino-terminal 763_scFv (anti-EGFR) and a C-terminal synthetic collagen scaffold gene coding for a peptide sequence of EPKSGDKTHTCPPCPRSIP$(GPP)_5$GKPGKP$(GPP)_6$GICDPSLC (SEQ ID NO: 17), which includes a mutant hinge region of human IgG (italics), a collagen-like domain (in boldface), and a disulfide knot (GICDPSLC (SEQ ID NO: 25)) of type XXI collagen. Shown below are the synthetic collagen scaffold-containing polypeptide and cDNA sequences (SEQ ID NOs: 17 and 18, respectively).

SEQ ID NO: 17:
GluProLysSerGlyAspLysThrHisThrCysProProCysProArg

SerIleProGlyProProGlyProProGlyProProGlyProProGly

-continued

```
ProProGlyLysProGlyLysProGlyProProGlyProProGlyPro

ProGlyProProGlyProProGlyProProGlyIleCysAspProSer

LeuCys

(note: Pro = Proline or Hydroxyproline)

SEQ ID NO: 18:
GAGCCCAAATCTGGTGACAAAACTCACACATGCCCACCGTGCCCAAGATC

TATTCCTGGGCCACCTGGTCCCCCAGGTCCTCCAGGACCCCCAGGGCCCC

CAGGTAAACCTGGAAAACCAGGGCCCCCAGGCCCCCCCGGGCCGCCTGGA

CCCCCAGGGCCACCAGGCCCCCCAGGCATCTGCGACCCATCACTATGT
```

This synthetic sequence (SEQ ID NO: 17) was prepared by overlapping PCR and the PCR product flanking with NotI and XhoI sites was cloned into the expression vector pSecTag2/Hygro (Invitrogen) at the same sites. The scFvs of 763 was then cloned in-frame to the above C-terminal collagen scaffold-containing construct at AscI and NotI sites to make the expression constructs of 763CSA2.

A bispecific CSA, 763CSAOKT3, was generated as follow. The scFv of OKT3 was cloned in-frame to the C-terminus of 763_scFv-Col at AgeI and BamHI sites to make the expression construct of 763CSAOKT3, where an anti-EGFR scFv of 763 is placed at the N-terminus, followed by a collagen scaffold polypeptide (SEQ ID NOs: 11) and a C-terminal anti-CD3 scFv of OKT3.

Another bifunctional binding partner, h4D5CSA-Luc, was constructed as follow. First, h4D5CSA was made by fusing an amino-terminal h4D5_scFv, derived from a humanized anti-HER2/neu IgG (Carter et al. (1992) *Proc Natl Acad Sci USA* 89, 4285-4289) to the C-terminal collagen scaffold-containing expression vector as mentioned in the section of construction of 763CSA2. Then, a *Gaussia* luciferase cDNA (U.S. Pat. No. 6,232,107) was in-frame fused to the C-terminus of h4D5_scFv-Col at AgeI and BamHI sites.

Each open reading frame of the various scFv, scFv-Fc, and CSA molecules contain sequences encoding an N-terminal leader sequence and a C-terminal myc epitope/polyhistidine tags for secretion, detecting, and purification purposes.

Summarized in Table below are various recombinant proteins/antibodies encoded by the above-described expression constructs:

TABLE 1

Overview of various antibody molecules used in this study

Figure 4:
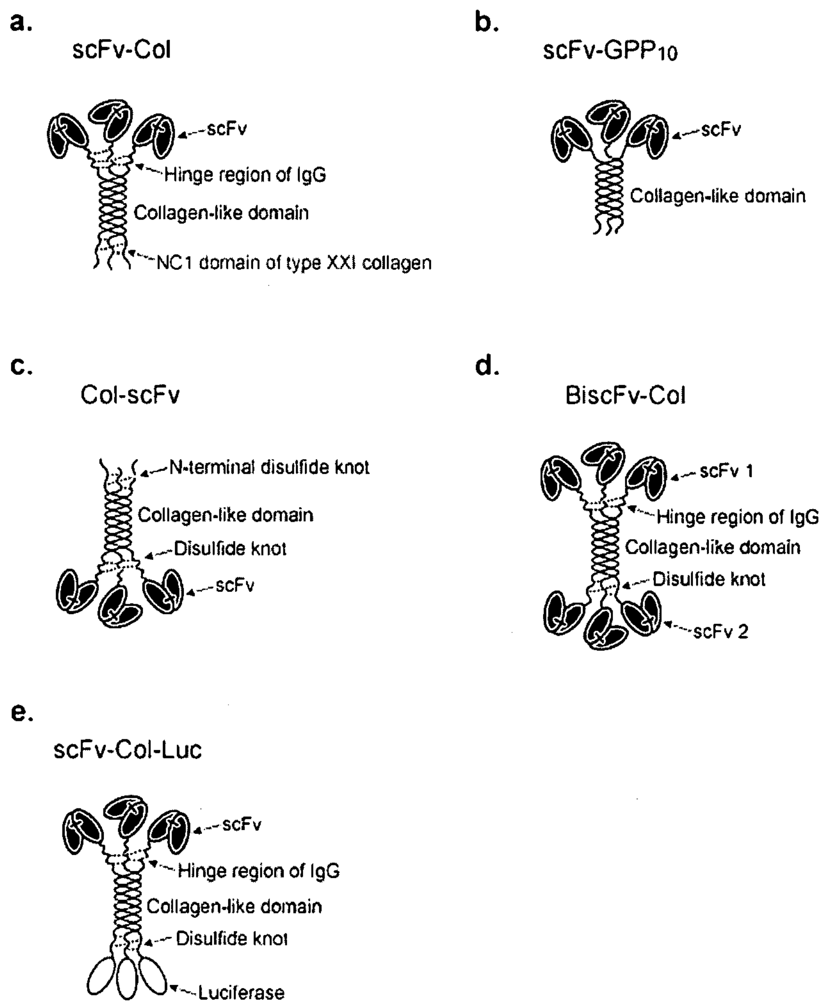
FIGS. 4A (a-e) and 4B (a-c) are schematic representations of different formats of antibodies: (A) trimeric collagen scaffold antibodies: scFv-Col (a), containing an amino-terminal scFv, a hinge region of human IgG, a collagen-like domain $(GPP)_{10}$ (SEQ ID NO: 20), and a carboxyl-terminal NCI domain of type XXI collagen; scFv-$GPP_{10}$ (b), containing an amino-terminal scFv and a collagen-like domain GSP$(GPP)_{10}$GPS (SEQ ID NO: 23); Col-scFv (c), containing an amino-terminal disulfide knot (TCPPCPRSIP (SEQ ID NO: 24)), a collagen-like domain $(GPP)_{10}$ (SEQ ID NO: 20), followed by a carboxyl-terminal disulfide knot (GICDPSLC (SEQ ID NO: 25)) derived from the NC1 domain of type XXI collagen and an scFv; BiscFv-Col (d), containing an amino-terminal scFv 1, a hinge region of human IgG, a collagen-like domain $(GPP)_{10}$ (SEQ ID NO: 20), followed by a carboxyl-terminal disulfide knot (GICDPSLC (SEQ ID NO: 25)) and an scFv 2; scFv-Col-Luc (e), containing an amino-terminal scFv, a hinge region of human IgG, a collagen-like domain $(GPP)_{10}$ (SEQ ID NO: 20), followed by a carboxyl-terminal disulfide knot (GICDPSLC (SEQ ID NO: 25)) and a luciferase; (B) from left to right: (a) immunoglobulin G (IgG), (b) chimeric (scFv-Fc), and (c) single-chain antibody (scFv, grey area). Dashed lines: interchain disulfide-bonds.
Figure 4:
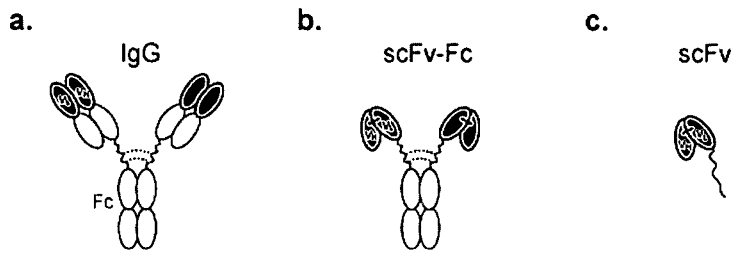

| Antibody | Target | Type | Structure |
|---|---|---|---|
| erb_scFv-Col | EGFR-ECD | CSA[1] | FIG. 4A, panel a |
| erb_scFv-$GPP_{10}$ | EGFR-ECD | CSA | FIG. 4A, panel b |
| Col-erb_scFv | EGFR-ECD | CSA | FIG. 4A, panel c |
| erb_scFv-Fc | EGFR-ECD | scFv-Fc | FIG. 4B, panel b |
| erb_scFv | EGFR-ECD | scFv | FIG. 4B, panel c |
| OKT3_scFv-Col | CD3 | CSA | FIG. 4A, panel a |
| OKT3 IgG | CD3 | IgG | FIG. 4B, panel a |
| 763_scFv-Col | EGFR | CSA | FIG. 4A, panel a |
| 763CSA2 | EGFR | CSA | FIG. 4A, panel a |
| 763CSAOKT3 | EGFR and CD3 | Bispecific CSA | FIG. 4A, panel d |
| h4D5CSA-Luc | HER2/neu | Bifunctional CSA | FIG. 4A, panel e |
| 357_scFv-Col | TNF-α | CSA | FIG. 4A, panel a |
| 357 IgG | TNF-α | IgG | FIG. 4B, panel a |

[1]Collagen scaffold antibody

Example 6

Expression of Recombinant Proteins

To generate the recombinant protein complexes/antibodies, the above-described scFv, scFv-Fc, and CSA constructs were transfected in mouse myeloma NS0 cells using Effectene (Qiagen) according to the manufacturer's instructions. After selection with Hygromycin (400 μg/ml) for 4 weeks, each stable clone was cultured in a shaker flask at an initial seeding density of $5\times10^5$ cells/ml in a chemically-defined medium HyQCDM4NS0 (Hyclone) containing 2% of fetal bovine serum. The culture was maintained at 150 rpm for five days at 37° C. Sodium ascorbate (80 μg/ml) was added to the culture media daily for those cells carrying expression constructs encoding proteins containing the above-mentioned antibody domains and the collagen scaffold domain, i.e., collagen scaffold antibodies (CSA).

Example 7

Purification of Recombinant Proteins

To purify CSA proteins listed on Table 1, around 2 L each of the filtered culture media were applied to a T-gel column (1.5×8 cm, Pierce) equilibrated with 50 mM Tris-HCl buffer containing 0.5 M of KCl, pH 8.0 at a flow rate of 60 ml/hour. After washing with the same buffer, the recombinant protein or protein complexes were eluted with 50 mM of sodium acetate buffer, pH4.0. Their UV absorbance was monitored at 280 nm and the peak fraction was applied onto a $ZnSO_4$—charged chelating Sepharose High Trap column (1-ml in bed volume, GE Healthcare) equilibrated with 50 mM Tris-HCl buffer containing 0.5 M NaCl, pH 8.0 at a flow rate of 60 ml/hour. The column was first washed with 20 mM of imidazole and then the bound protein or protein complexes were eluted with 0.25 M of imidazole in the same buffer. The final preparation was dialyzed against 50 mM of Hepes buffer, pH 7.0. Then, SDS-PAGE was carried out using either a 10% NuPAGE bis-Tris polyacrylamide gel with MOPS or a 7% SDS/Tris-acetate polyacrylamide gel with sodium acetate as running buffer (Invitrogen). Proteins were then stained with Coomassie brilliant blue R-250. Densities of protein bands were quantified by densitometry using ChemiImager 5500 (Alpha Inn8).

Trimerization Studies

To examine the triple helical nature, purified erb_scFv-Col (1 mg/ml) was incubated at 37° C. in the absence or presence of 10 mM DTT for 1 h. An aliquot from the DTT treated sample was further reacted with 50 mM N-ethylmaleimide (NEM) for 30 minutes at an ambient temperature to permanently block free sulfhydryls and reformation of trimers. An equal amount of protein from each sample was electrophoresed on a 7% SDS/Tris-acetate polyacrylamide gel with sodium acetate as the running buffer. The gel was stained with Coomassie blue. It was found that the purified CSAs were homotrimers or interchain disulfide-bonded hexamer, which can be dissociated into two trimers under mild reducing conditions.

Thermal stability of the trimeric structure of erb_scFv-Col was examined. Purified erb_scFv-Col in 50 mM Tris-HCl (pH 8.0), containing 2 M urea was treated in the absence or presence of 10 mM tris(2-carboxyethyl)phosphine (TCEP) at an ambient temperature. The reduced samples were then alkylated with 50 mM of NEM at an ambient temperature. Each sample with an equal amount of protein was heated for 10 minutes at 35, 45, 55, 65, 75, and 85° C. before mixing the SDS-loading buffer. The samples were electrophoresed on a 10% SDS/Bis-Tris polyacrylamide gel with the MOPS buffer under non-reducing conditions. The gel was stained with Coomassie blue. The result indicated that erb_scFv-Col trimer exhibited high thermal stability. Indeed, after treated at and 65° C. for 10 minutes, more than 50% of the trimers remained. It was also found that the trimeric structure of the collagen-like domain of erb_scFv-Col was prolyl hydroxylated.

Figure 5:
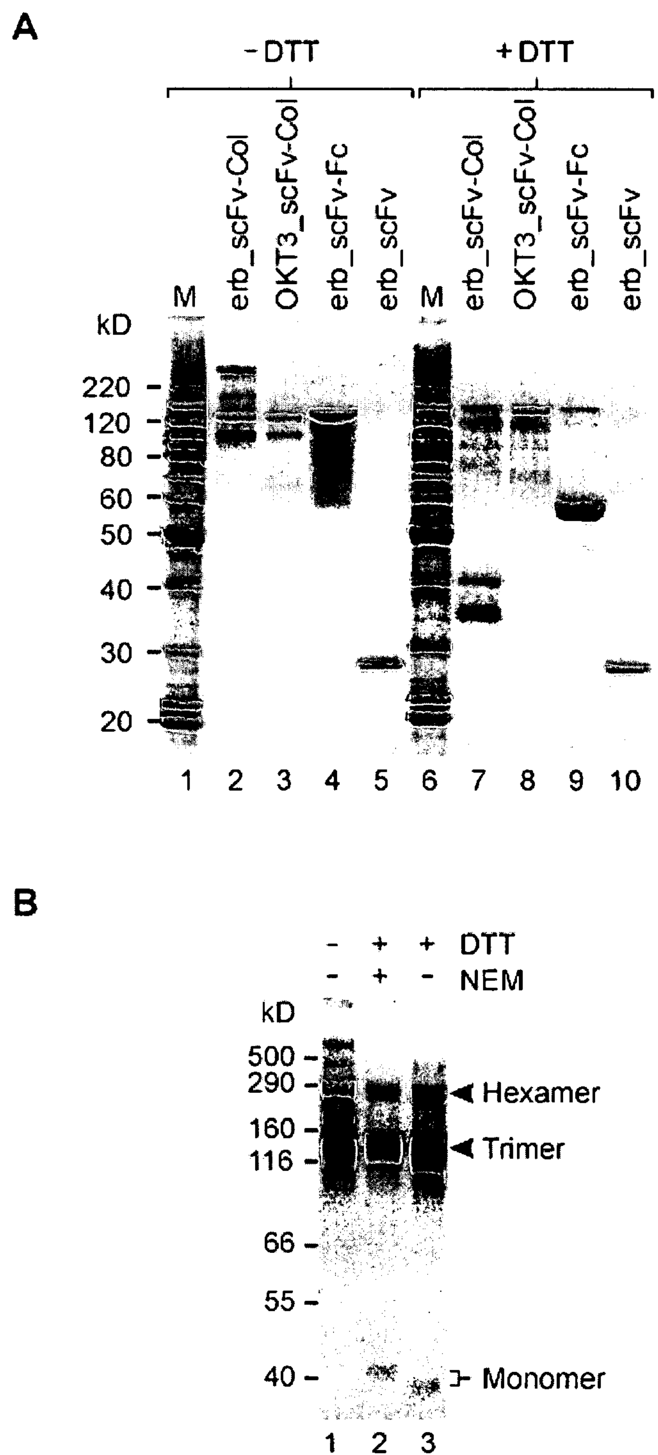
FIGS. 5 A-B depict purification and structural characterization of the various antibody molecules in mammalian cells. (A) The indicated antibodies were stably expressed in mammalian cells and purified from culture media by column chromatographies. The samples were electrophoresed on a 10% SDS/Bis-Tris polyacrylamide gel with MOPS buffer under non-reducing conditions (lanes 1 to 5) and reducing conditions, where sample was treated with 50 mM of DTT for 10 min at 70° C. (lanes 6 to 10). (B) An erb_scFv-Col hexamer is formed by the interchain disulfide-bonding of two trimeric molecules. Purified erb_scFv-Col (1 mg/ml) was incubated at 37° C. in the absence (lane 1) or presence (lanes 3) of 10 mM DTT for 1 h. An aliquot from the DTT-treated sample was further reacted with 50 mM N-ethyl-maleimide (NEM) for 30 min. at ambient temperature (lane 2). All samples with equal amounts of protein were electrophoresed on a 7% SDS/Tris-acetate polyacrylamide gel with sodium acetate as a running buffer. The gel was stained with Coomassie blue. "M" indicates molecular mass standards.

The primary structure of erb_scFv-Col or OKT3_scFv-Col comprises a human or mouse single-chain Fv targeting domain, a human $IgG_1$ hinge region, a $(Gly-Pro-Pro)_{10}$ (SEQ ID NO: 20) collagen-like peptide, and the NC1 domain of type XXI collagen. Recombinant antibodies of erb_scFv-Col, OKT3_scFv-Col, erb_scFv-Fc and erb_scFv were expressed as soluble secretory proteins in mouse myeloma NS0 cells and were purified individually from culture media by column chromatography as previously described. FIG. 5A depicts the SDS-PAGE analysis of these purified antibodies. Under non-reducing conditions, two major bands were resolved in erb_scFv-Col (lane 2), while only a single major band was observed in OKT3_scFv-Col (lane 3). The lower band of both erb_scFv-Col and OKT3_scFv-Col migrated to a position of 125 kD, corresponding closely to the calculated molecular mass of the trimeric form of both scFv-Col monomers (41 kD). The upper band shown in erb_scFv-Col (lane 2) appears to be an interchain disulfide-bonded dimer of trimers.

This finding was confirmed by incubating the sample under mild reducing conditions as shown in FIG. 5B: the interchain disulfide-bonded hexamer (250 kD) of erb_scFv-Col was dissociated into two trimers (125 kD). In FIG. 5A, samples were treated under reducing conditions with 50 mM of DTT for 10 min at 70° C., and the interchain disulfide-bonded hexamer of erb_scFv-Col was completely reduced to the trimeric form, while only some of the erb_scFv-Col trimer was further dissociated into monomer (lane 7). Interestingly, the trimeric conformation of OKT3_scFv-Col was resistant to dissociation into a monomeric form under these reducing conditions (lane 8). The bivalent counterpart of erb antibody, erb_scFv-Fc migrated as a dimmer under non-reducing conditions with an apparent molecular mass of 125 kD (lane 4), revealing an almost monomeric form with an apparent molecular mass of 57 kD after the interchain disulfide bonds were reduced (lane 9).

Figure 6:
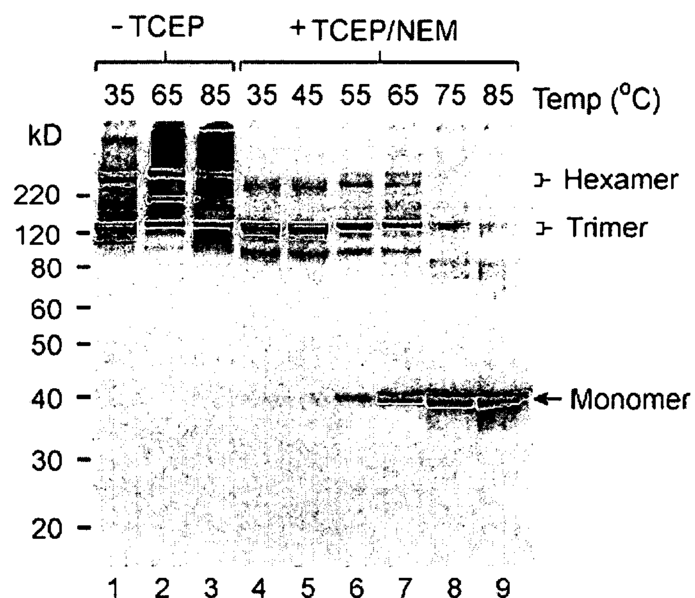
FIGS. 6 A-B depict the thermal stability of trimeric structure of erb_scFv-Col. (A) Purified erb_scFv-Col in 50 mM Tris-HCl (pH 8.0), containing 2 M urea, was treated in the absence (lanes 1 to 3) or presence (lanes 4 to 9) of 10 mM TCEP at ambient temperature. The reduced samples were alkylated with 50 mM NEM at ambient temperature. All samples, which had an equal amount of protein, were heated for 10 min at the indicated temperatures and then SDS-loading buffer was added immediately. The samples were electrophoresed on a 10% SDS/Bis-Tris polyacrylamide gel with MOPS buffer under non-reducing conditions. The gel was stained with Coomassie blue. (B) Quantitation of the reduced/alkylated erb_scFv-Col trimer levels at different incubation temperatures in (a) (from lanes 4 to 9). Densities of protein bands were quantified using a densitometer. The total amounts of trimer and monomer at each temperature point were normalized to 100.
Figure 6:
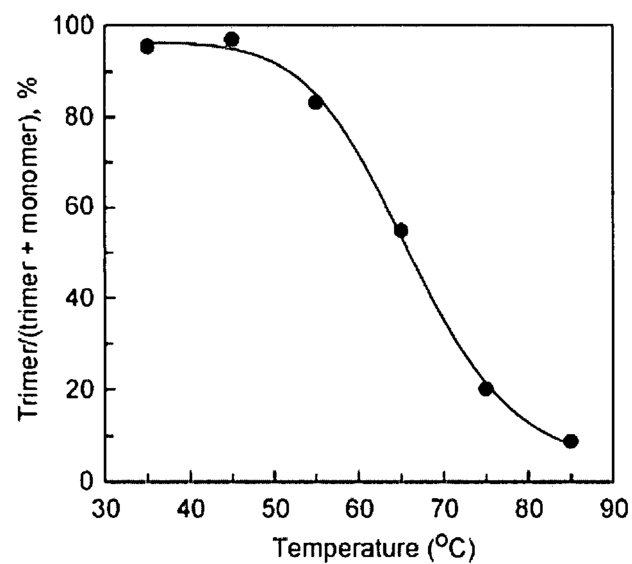

These results imply that the short collagen-like peptide $(Gly-Pro-Pro)_{10}$ (SEQ ID NO: 20) within the CSA molecules of erb_scFv-Col and OKT3_scFv-Col can be responsible for assembling into a thermally stable trimeric conformation (see below). The monovalent counterpart of the erb antibody, erb_scFv, migrated as a single band with an apparent molecular mass of 28 kD under either non-reducing or reducing conditions. The hexa- and trimeric structures of the interchain disulfide-bonded species of erb_scFv-Col shown in FIG. 5 were further characterized to determine its triple-helical thermal stability. To exclude the contribution of interchain disulfide-bridges to the trimeric assembly of the CSA molecules, the cysteine residues in erb_scFv-Col were first completely reduced using a strong reducing agent TCEP at room temperature, and then alkylated with NEM to prevent the reformation of the disulfides bonds. Equal amounts of non-reduced or reduced/alkylated samples were incubated in Tris-HCl (50 mM, pH 8) that contained 2M urea at the indicated temperatures and the dissociation of the triplex was assayed by SDS-PAGE under non-reducing conditions to estimate the thermal stability of the collagen triple helix. As expected, the interchain disulfide-bonded hexamer specie was readily dissociated into trimers at 35° C. (FIG. 6A, compare lanes 1 and 4). The timers dissociated into monomers significantly as the incubation temperature was increased (FIG. 6A, lanes 4-9). The midpoint transition temperature (Tm) of erb_scFv-Col under 2 M urea after reduction/alkylation was determined to be 66° C., at which half of the trimer was unfolded into monomers (FIG. 6A). The same experiment under non-reducing conditions (FIG. 6A, lanes 1-3) did not show any alteration of the hexameric or trimeric structure, although erb_scFv-Col was partially degraded at high incubation temperatures.

This phenomenon is consistent with other work that demonstrated that GPP-containing peptides were sensitive to heating at 90° C., and partially degraded, and that introducing 2.5 M of guanidium HCl into the collagen-like sample reduced Tm by 27° C.

Figure 7:
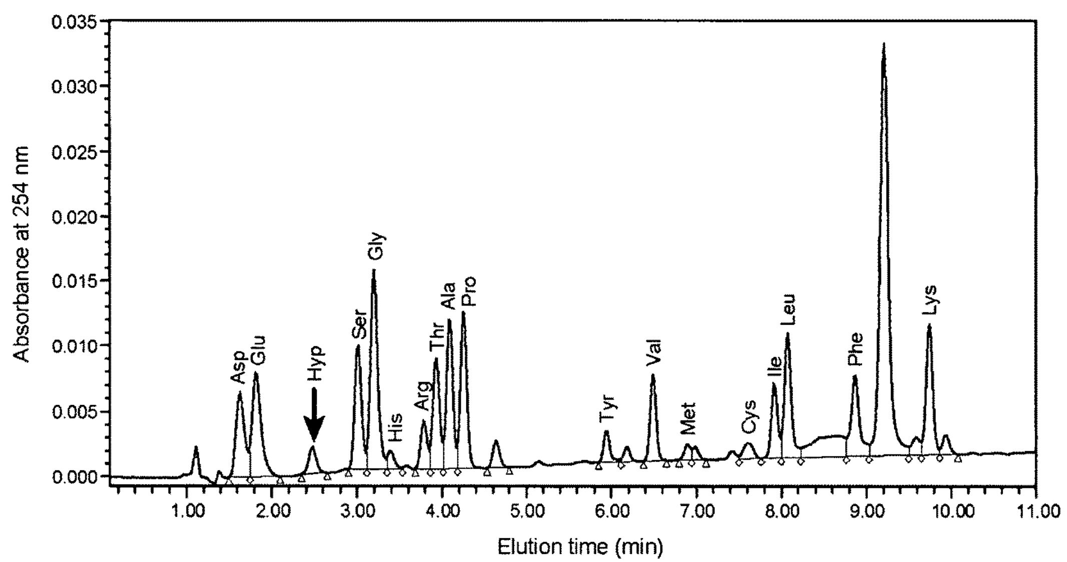
FIG. 7 depicts an HPLC elution profile of phenylthiocarbamyl (PTC) amino acid derivatives of erb_scFv-Col following acid hydrolysis. The phenylisothiocyanate (PITC)-derivatized amino acids of erb_scFv-Col after acid hydrolysis were separated on a reverse phase C18 silica column and the PTC chromophores were detected at 254 nm. The peak position of hydroxyproline (Hyp) derivative is indicated by an arrow.

Hydroxyproline is important to the thermal stability of a collagen triplex structure. Amino acid composition analyses were conducted on a purified sample to investigate the presence of hydroxyproline in erb_scFv-Col. Purified erb_scFv-Col was dialyzed against 50 mM acetic acid, hydrolyzed in 6 N of HCl at 110° C. for 24 h and subjected to amino acid analysis in a Waters PicoTag® system. A close match was observed between the determined amino acid composition and the predicted data based on the deduced cDNA sequence of erb_scFv-Col (Table 2). Additionally, the peak position of the hydroxyproline derivative was detected on the HPLC elution profile, suggesting that the Pro residues in the Y position of the collagenous Gly-X-Y triplet in $(Gly-Pro-Pro)_{10}$ (SEQ ID NO: 20) were subject to hydroxylation (FIG. 7).

The extent of prolyl hydroxylation in erb_scFv-Col is 61%, as determined from the theoretical value of ten fully hydroxylated proline residues in its $(Gly-Pro-Pro)_{10}$ (SEQ ID NO: 20) motif (see Hyp residues in Table 2). The results indicate that the $(Gly-Pro-Pro)_{10}$ (SEQ ID NO: 20) motif in CSA molecules is a good substrate for prolyl 4-hydroxylase and the mouse myeloma NS0 cells exhibit sufficient prolyl hydroxylase activity for the biosynthesis of collagen molecules.

TABLE 2

Amino acid analysis of the purified erb_scFv-Col expressed in NS0 cells

| Amino acid | erb_scFv-Col | Calculated[a] |
|---|---|---|
| | Residues | |
| Asx | 22.2 ± 0.4[b] | 22 |
| Glx | 25.5 ± 0.3 | 26 |
| Hyp | 6.1 ± 0.4 | 10[c] |
| Ser | 36.0 ± 1.2 | 44 |
| Gly | 46.9 ± 0.5 | 47 |
| His | 7.8 ± 0.3 | 7 |
| Arg | 15.0 ± 0.4 | 15 |
| Thr | 22.9 ± 0.6 | 24 |
| Ala | 27.6 ± 0.3 | 26 |

TABLE 2-continued

Amino acid analysis of the purified erb_scFv-Col expressed in NS0 cells

| Amino acid | erb_scFv-Col Residues | Calculated[a] |
|---|---|---|
| Pro | 32.4 ± 1.3 | 28 |
| Tyr | 12.8 ± 0.5 | 14 |
| Val | 16.1 ± 1.0 | 14 |
| Met | 4.6 ± 0.7 | 3 |
| Cys | 5.8 ± 1.8 | 9 |
| Ile | 13.2 ± 0.6 | 12 |
| Leu | 22.5 ± 1.1 | 20 |
| Phe | 11.2 ± 0.4 | 10 |
| Lys | 14.6 ± 0.9 | 12 |

[a]The calculated amino acid residues are based on the deduced amino acid sequence of erb_scFv-Col after removal of the signal sequence.
[b]The values are given as mean ± S.D., n = 3.
[c]The value is predicted as the proline residues in the Y position of a collagenous GXY triplet sequence (Kivirikko et al., (1992) In Post-Translational Modifications of Proteins (Harding, J. J., and Crabbe, M. J. C., Eds.). CRC Press, Boca Raton, FL.: 1-51).

The presence of high levels of trimeric soluble antibodies in the culture supernatants indicated that the monomeric subunits containing an antibody domain and a scaffold domain could be trimerized and secreted. The presence of the antibody domain within the same polypeptide as the scaffold domain did not prevent trimerization, did not prevent the formation of a soluble antibody, and did not prevent secretion of the antibody into the culture medium. Thus, the invention allows the trimerization of antibodies, the formation of a soluble antibody, and the secretion of soluble trimeric antibodies.

Example 9

Binding Studies

The binding kinetics of erb antibody variants to the EGFR-ECD were measured using a BIAcore X biosensor (BIACORE, Inc., Uppsala, Sweden) in the running buffer HBS-EP (10 mM HEPES, pH 7.4, 150 mM NaCl, 3 mM EDTA, 0.005% surfactant P20). Briefly, EGFR-ECD was immobilized onto a C1 sensor chip via amine coupling to a level of 1700 response units (RU) and purified antibodies with different concentrations were injected at a flow rate of 10 μl/min. The surface was regenerated by injection of 5 μl of 10 mM glycine-HCl, pH 3.5. Sensorgrams were obtained at each concentration and were evaluated using the program, BIA Evaluation 3.2. Binding data were titled with a 1:1 Langmuir binding model to calculate the equilibrium dissociation constant, $K_D$, which was defined as the ratio of dissociation rate ($k_{off}$)/association rate ($k_{on}$). The results were shown in Table 3 below.

TABLE 3

Binding kinetics of various form of erb antibody to immobilized EGFR-ECD

| Antibody | $k_{on}/10^5$ $M^{-1}s^{-1}$ | $k_{off}/10^{-4}$ $s^{-1}$ | $K_D$ nM |
|---|---|---|---|
| erb_scFv-Col | 1.72 | 8.22 | 4.78 |
| erb_scFv-Fc | 0.909 | 94.4 | 104 |
| erb_scFv | 0.15 | 741 | 4960 |

As shown in Table 3, the binding avidity of erb_scFv-Col for EGFR-ECD is approximately 20- and 1000-fold stronger than the bivalent (erb_scFv-Fc) and monovalent (erb_scFv) mAb counterparts, respectively.

Figure 8:
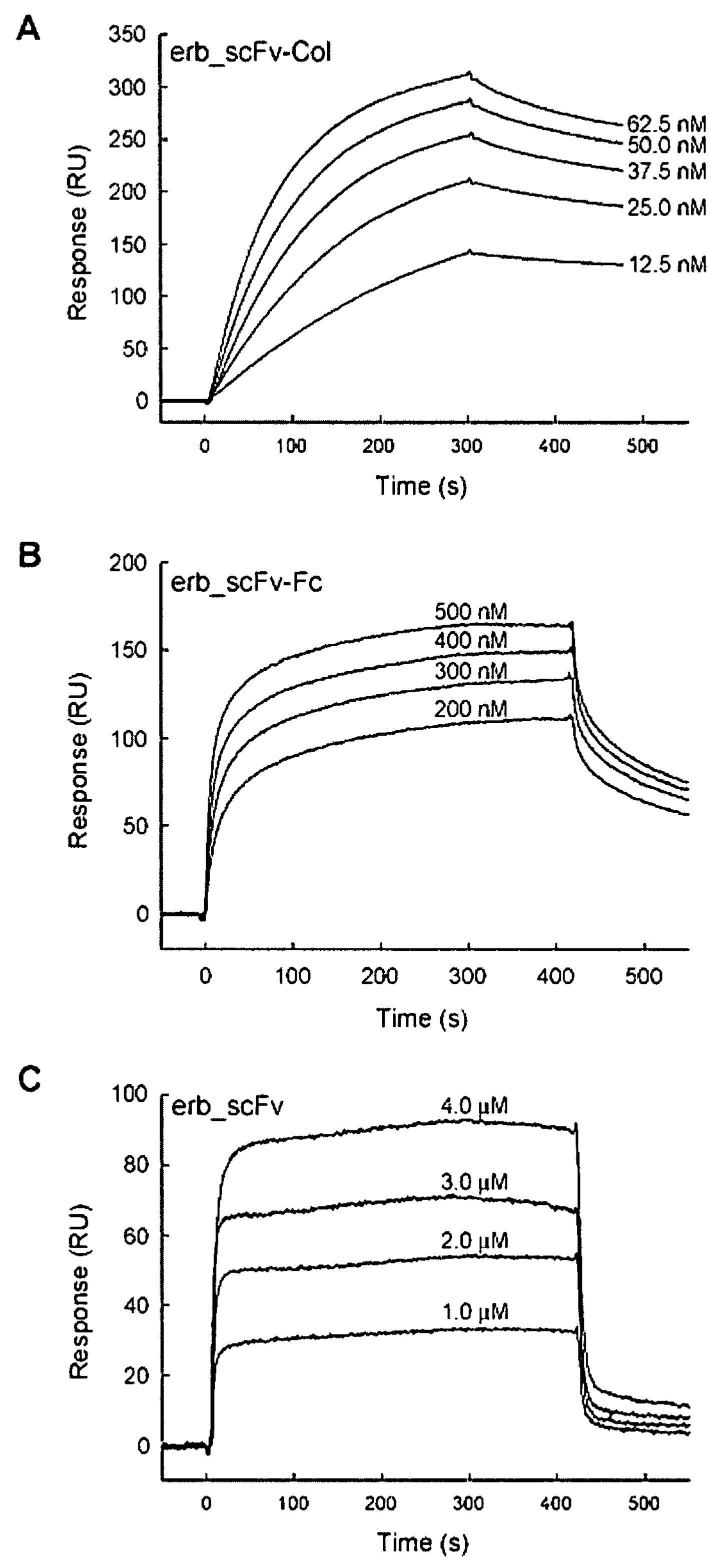
FIGS. 8 A-C depict surface plasmon resonance analysis of interaction between extracellular domain of EGFR and erb_scFv-Col (A); erb_scFv-Fc (B) or erb_scFv (C). Each antibody was injected at indicated concentrations and flowed over a surface chip with immobilized EGFR extracellular domain at a flow rate of 10 μl/min.

Antibody binding analysis demonstrates that the structure design of CSA molecules does not alter the binding activity of the scFv domains. Surface plasmon resonance and cell flow cytometry were used to examine whether scFv binding activity is retained in erb_scFv-Col and OKT3_scFv-Col, respectively. Additionally, the increase in antigen-binding avidity by trivalent scFv in CSA molecules was compared with that by their bivalent and/or monovalent counterparts. The interaction of the three erb antibody variants, erb_scFv-Col, erb_scFv-Fc and erb_scFv, with EGFR-ECD was studied using a surface plasmon resonance assay and the equilibrium dissociation constant $K_D$ was determined as the ratio between the dissociation and association rate constants ($k_{off}/k_{on}$) The $K_D$ of the binding of monovalent erb_scFv with EGFR-ECD ligands is of the order of $10^{-6}$ M, whereas the $K_D$ of the binding of bivalent erb_scFv-Fc and trivalent erb_scFv-Col to EGFR is of the order of $10^{-7}$ and $10^{-9}$ M, respectively (FIG. 8 and Table 3). The increase in the apparent avidity of the trivalent erb CSA over that of the bivalent and monovalent counterparts is approximately 20- and 1000-fold, respectively. Notably, the dissociation rate constant ($k_{off}$) of erb_scFv-Col is $8.22\times10^{-4}$ $s^{-1}$, and for erb_scFv-Fc is $94.4\times10^{-4}$ $s^{-1}$, representing an 11-fold improvement in the off-rate for the trivalent species.

The functional affinities of OKT3_scFv-Col and OKT3 IgG for binding to CD3 molecules on the cell surface of human CD3(+) T-cells were determined by flow cytometry analysis using antibody displacement assay with a saturated concentration (0.25 μg/ml) of OKT3-FITC as a competitor. All of the following procedures were conducted at 4° C. Human T cells were suspended in an FCM buffer (phosphate-buffered saline with 2% FBS and 0.1% sodium azide) at a density of $1\times10^6$ cells/ml. The cells were treated with mouse total IgGs (2 μg/ml, Jackson ImmunoResearch Laboratories) for 30 minutes and were then incubated with a serial dilution of OKT3_scFv-Col or OKT3 antibody for 1 hour. A fixed, saturating amount (determined by flow cytometry) of FITC-conjugated OKT3 (0.25 μg/ml, purchased from eBioscience, Inc.) was added directly. After incubation for 1 hour, the cells were washed with the FCM buffer and analyzed for immunofluorescence by flow cytometry on a FACScan (Becton Dickinson, San Jose, Calif.). The data were presented as percent inhibition of maximal fluorescence intensity, which is defined as the mean fluorescence intensity obtained by staining T cells with OKT3-FITC in the absence of blocking antibodies. The concentration of each mAb required to inhibit half the maximal fluorescence intensity ($IC_{50}$) was calculated.

Figure 9:
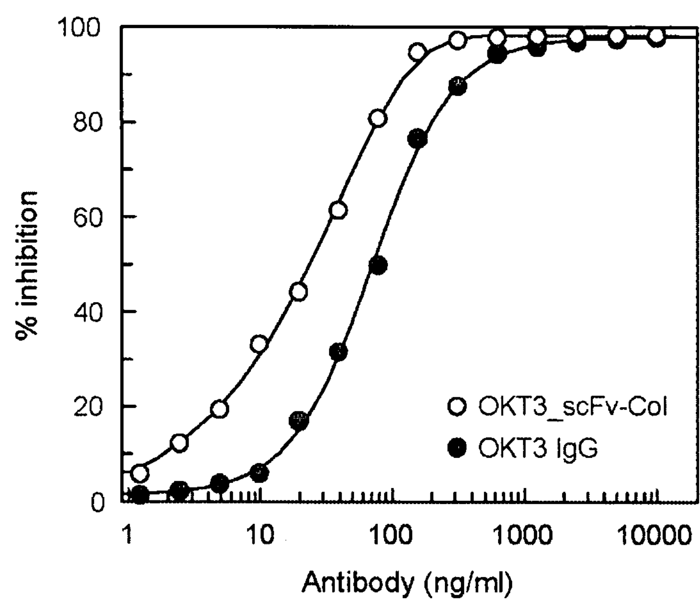
FIG. 9 depicts an OKT3 displacement assay. Human CD3(+) T-cells were incubated with serial dilutions of either OKT3_scFv-Col or OKT3 IgG for 1 h. A saturating amount of OKT3-FITC was added and incubated for additional hour. Cells were washed and bound; OKT3-FITC was quantified by flow cytometry. Values are expressed as percent inhibition of maximal fluorescence, as determined by adding OKT3-FITC without prior blocking antibodies.

It was estimated that the binding avidity of OKT3 IgG and OKT3_scFv-Col to human CD3(+) T-cells were 1.33 nM for OKT3 IgG and 0.45 nM for OKT3_scFv-Col. Thus, the $IC_{50}$ values indicated that the avidity of the trivalent OKT3_scFv-Col for CD3(+) T-cells is about three times greater than that of the bivalent OKT3 IgG (FIG. 9). The results indicated that OKT3_scFv-Col binds to human CD3+ T cells more strongly than the native murine OKT3 mAb.

Thus, binding analysis results obtained using surface plasmon resonance and cell-binding assays reveal that both the trivalent erb and OKT3 CSAs significantly improve the binding avidity compared to their bivalent counterparts. The binding analyses also show that trimeric soluble antibodies of the invention can show a binding affinity in the nanomolar range. Consequently, soluble trimeric antibodies with high affinities for their ligands can be achieved with the invention.

Example 10

Stability and Pharmacokinetic Assays

For serum stability assay, the stability of various forms of erb_scFv-Col, erb_scFv-Fc, or erb_scFv antibody was determined by incubating with human serum at 37° C. The amount of active anti-EGFR remaining after different periods of incubation times was measured by quantitative ELISA. The ELISA was conducted by employing the recombinant EGFR-ECD (as capture reagent) and anti-c-myc mAb (9E10, Sigma Chemical Co.), followed by an HRP-conjugated affinity-purified polyclonal goat anti-mouse IgG and chemiluminescent substrates (Pierce Biotechnology, Inc.). For pharmacokinetic assay, three BALB/c nude mice were used to analyze erb_scFv-Col clearance. Briefly, following a pre-bleed, each mouse was injected subcutaneously (s.c.) with 25 μg (2 mg/kilogram of body weight) of erb_scFv-Col. During the next 70 h, periodic blood samples were collected and evaluated for their content of erb_scFv-Col by ELISA.

Figure 10:
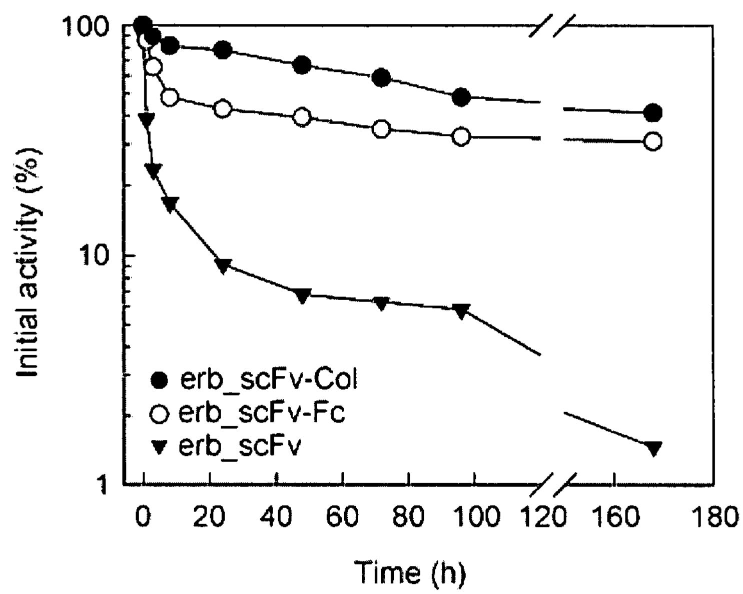
FIGS. 10 A-B depict the stability of CSA molecule. (A) Stability of the various forms of erb antibody in human serum. The stability of erb_scFv-Col, erb_scFv-Fc or erb_scFv was determined by incubating at 37° C. in human serum. The amount of active anti-EGFR that remained after various periods of incubation was determined by ELISA using anti-c-myc mAb. (B) Pharmacokinetics of erb_scFv-Col in mice. Male C57BL/6 mice were injected intravenously with 2 mg/Kg of erb_scFv-Col. Blood samples were drawn at different times. The erb_scFv-Col levels in plasma were determined by ELISA using rabbit anti-c-myc antibodies conjugated with HRP. Results were averaged from 3 animals for each time point and error bars represent the standard deviation.
Figure 10:
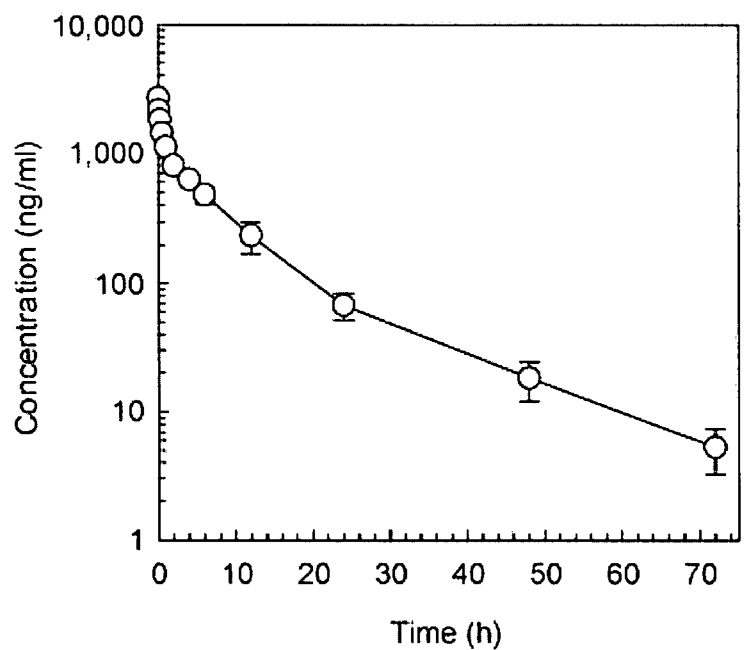

The triple-helical structure of the collagenous domain normally makes collagens resistant to non-specific proteolytic enzymes. The serum stability of erb_scFv-Col was studied and compared with those of erb_scFv-Fc and erb_scFv by incubating each of the purified antibody variants in human serum at 37° C. for various periods. The immunoreactivity of the various erb antibodies was determined by ELISA. As shown in FIG. 10A, erb_scFv-Col was more stable than erb_svFv-Fc in human serum at physiological temperature, retaining 60% of its initial binding activity within 72 h of incubation. The erb_scFv degraded rapidly in human serum, retaining less than 40% of its initial binding activity within 1 h of incubation. The results indicated that the triple-helical collagen-like peptide of erb_scFv-Col and the Fc region of erb_scFv-Fc are more resistant than erb_scFv to serum protease digestion. Thus, the soluble trimeric antibodies of the invention can have higher serum stability than monomeric or dimeric antibodies.

FIG. 10B presents the pharmacokinetic profile of erb_scFv-Col in mice. Kinetics of the two-compartment model was determined after a single intravenous administration of erb_scFv-Col at 2 mg/kg. The plasma level of immunoreactivity decreased biphasically with a distribution phase half-life ($t^{1/2}\alpha$) of 0.21 h and a terminal elimination phase half-life ($t^{1/2}\beta$) of 4.78 h.

T Cell Proliferation Assay and Mixed Lymphocyte Reaction (MLR)

5-bromo-2'-deoxyuridine (BrdU) cell proliferation assay was performed. Briefly, human peripheral blood mononuclear cells (PBMCs) were plated in a black 96-well flat bottom tissue culture plate at $2\times10^5$ cells/well in 100 μl RPMI-1640 medium with 10% FBS at 37° C. in the presence of 10-fold serial dilution of OKT3 (eBioscience, Inc.) or OKT3_scFv-Col for 66 h. The cells were then pulsed with 10 μM of BrdU for 6 h. After removing the culture medium, the cells were fixed and DNA was denatured in one step with FixDenat. Afterward, the cells were incubated with a peroxidase labeled anti-BrdU antibody (anti-BrdU POD, Fab fragments) for 1.5 h at room temperature. Chemiluminescence detection and quantification was performed using a microplate-luminometer (Hidex, CHAMELEON detection platform, Finland).

T cell proliferation and immunosuppression in the one-way mixed lymphocyte reaction was assessed as follows. Human PBMCs were obtained from two healthy donors (stimulator and responder). Stimulator or responder cells were treated with 25 μg/ml of mitomycin C (Sigma-Aldrich) in a complete medium (RPMI 1640 supplemented with 10% human AB serum, 2 mM glutamine, 50 nM 2-mercaptoethanol, and 100 units/ml each of penicillin and streptomycin) for 30 minutes in humidified air containing 5% $CO_2$ at 37° C., followed by three washes in RPMI 1640 medium. Responder cells were cultured alone or mixed with mitomycin C treated stimulator or mitomycin C responder cells at 1:1 ratio at $2\times10^5$ cells/well in 200 μl of complete medium. Purified OKT3_scFv-Col or OKT3 was added at different concentrations to cultures immediately after responder cell plating. After 5 days, cultured cells were pulsed with 10 μM of BrdU and harvested 24 h later. Cell proliferation assay was then performed in the manner described above.

Figure 11:
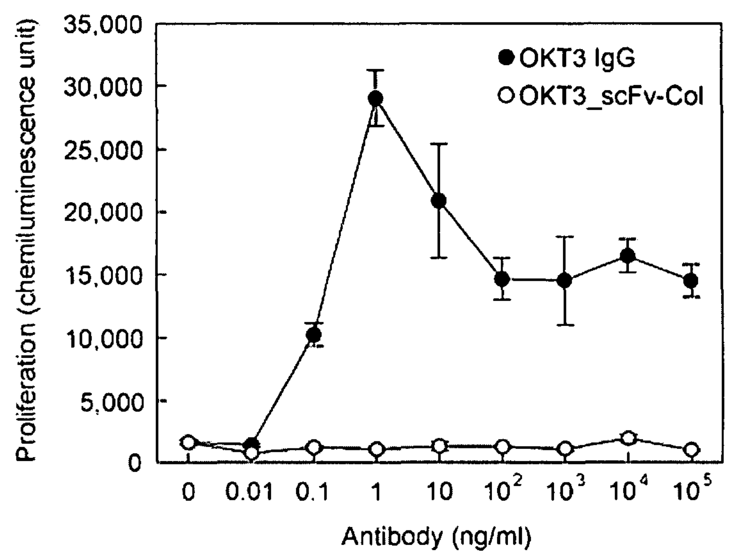
FIGS. 11 A-B depict that the OKT3-derived CSA is non-mitogenic with effective immunosuppressive activity. (A) T cell proliferation in response to OKT3 IgG and OKT3_scFv-Col. Human PBMCs were collected from three healthy normal donors and incubated individually with serial log dilutions of OKT3 IgG or OKT3_scFv-Col for 72 h, pulsed with 10 μM BrdU for an additional 8 h. The cell proliferation was measured by BrdU-ELISA using chemiluminescent immunoassay to quantify the incorporation of BrdU during DNA synthesis. Each point represents mean±S.D. of three donors. (B) Inhibition of mixed lymphocyte reaction by OKT3 IgG and OKT3_scFv-Col. Responder PBMCs mixed with mitomycin C-treated stimulator PBMCs were cocultured for five days in the presence of different concentrations of OKT3 IgG (filled circles) or OKT3_scFv-Col (open circles), pulsed with BrdU for an additional 16 h. The cell proliferation was measured by BrdU-ELISA. The responder PBMCs mixed with mitomycin C-treated stimulator PBMCs and responder PBMCs in the absence of antibody were shown in a filled square and a filled triangle, respectively. The cell proliferation of the untreated stimulator PBMCs in the absence of antibody is shown in an open square.
Figure 11:
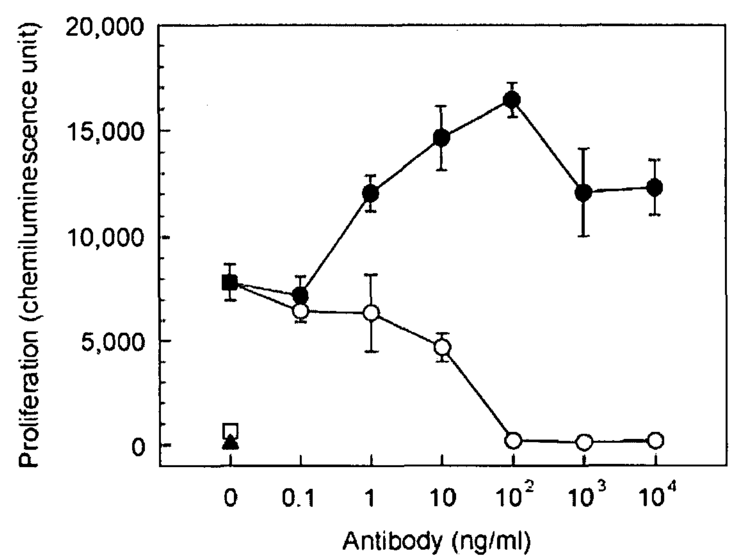

To determine whether OKT3_scFv-Col, upon increasing the binding avidity to CD3(+) T-cells, can exhibit immunosuppressive activity that is superior to that of the parental OKT3 IgG, both were tested for T-cell mitogenic activation in a one-way mixed lymphocyte reaction (MLR). In mixed PBMC cultures (mitomycin C treated stimulator+responder) incubated for 5 days without antibody treatment, a mixed lymphocyte reaction (MLR) developed as a result of allogeneic stimulation of T cell activation (FIG. 11B, filled square). Treating mixed PBMC cultures with OKT3 IgG further stimulates the proliferation of T cells (FIG. 11B, filled circles). In contrast, OKT3_scFv-Col suppressed MLR in a dose-dependent manner, reaching the background level at a concentration of 100 ng/ml (FIG. 11B, open circles). These results indicate that OKT3_scFv-Col is a potent immunosuppressant of T cell proliferation while exhibiting reduced mitogenicity in vitro.

Cytokine Measurement

The mitogenic activity of murine OKT3 is caused by extensive T cell receptor (TCR)—CD3 crosslinking via binding to FcR-positive cells. Therefore, efforts have recently been made to develop non-mitogenic forms of anti-CD3 by altering the binding to the Fc receptor. As a model of the CSA molecule, OKT3_scFv-Col was generated to test whether it is nonmitogenic by replacing the Fc region of OKT3 IgG with a collagen-like peptide. Human PBMCs were plated at $2\times10^5$ cells/well in 0.1 ml RPMI-1640 medium with 10% FBS at 37° C. in the presence of 10-fold serial dilution of OKT3 or OKT3_scFvCol. The supernatants were harvested at different time points and multiple cytokines were measured using a human cytokine immunoassay kit (eBioscience, Inc.).

Figure 12:
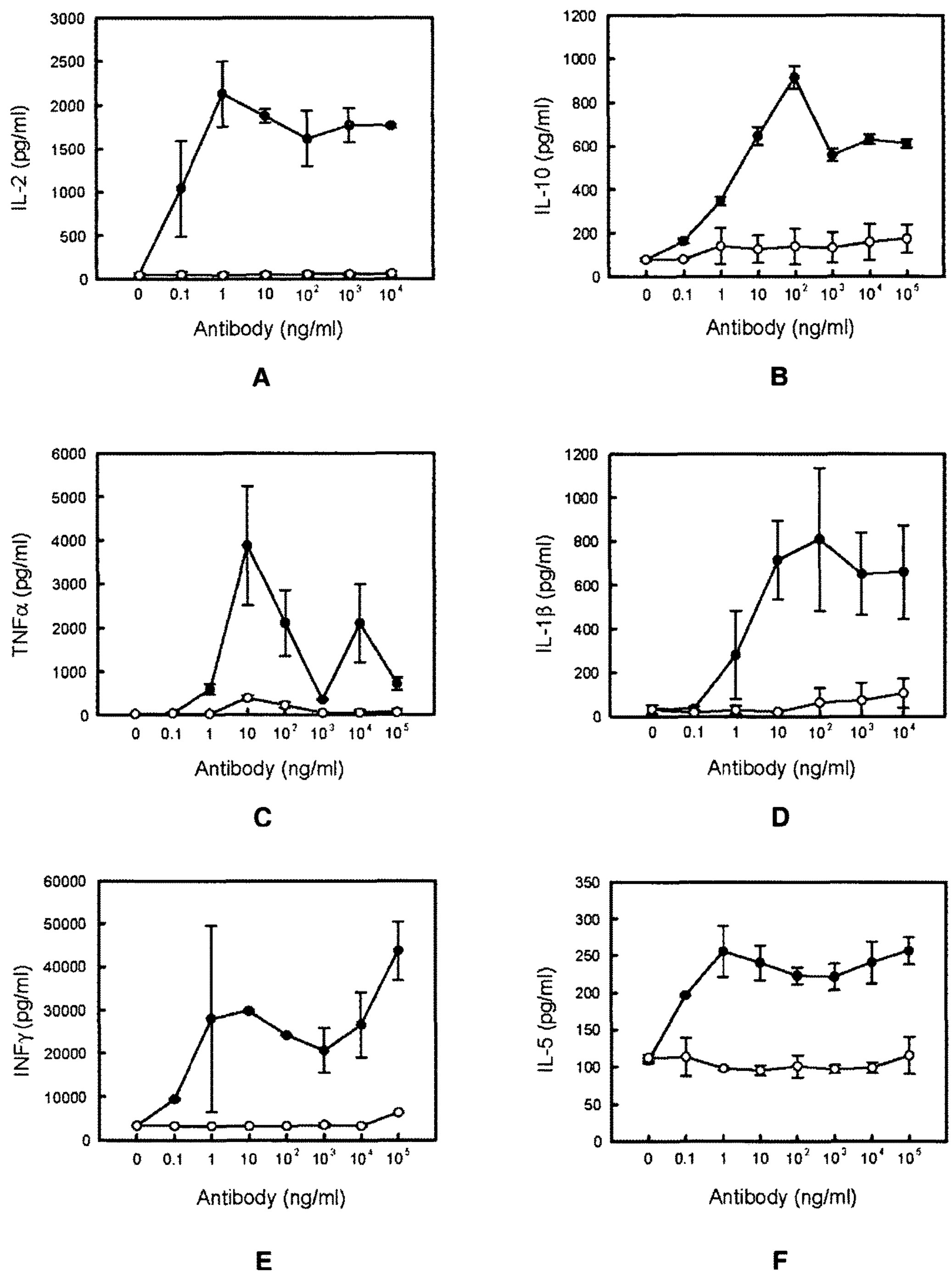
FIGS. 12 A-F depict release of cytokines induced by OKT3 IgG and OKT3_scFv-Col. Human PBMCs were collected from three healthy normal donors and incubated individually with serial log dilutions of OKT3 IgG (filled circles) or OKT3_scFv-Col (open circles). The levels of IL-2 and the rest of the indicated cytokines in the culture supernatants were determined by ELISA at 24- and 72-h time points, respectively. Each point represents the mean±S.D. of three donors.

The capacities of OKT3 IgG and OKT3_scFv-Col to induce T cell proliferation and release inflammatory and other cytokines (IL-2, IFN-γ and TNF-α) were measured. As expected, OKT3 IgG induced T cell proliferation and cytokine production at a very low dose, while no detectable T cell proliferation or cytokine production was induced by OKT3_scFv-Col, even at high concentrations (FIG. 11A and FIG. 12). Therefore, these results demonstrate that, unlike OKT3 IgG, OKT3_scFv-Col does not exhibit T-cell activating properties. The results indicated that administration of OKT3_scFv-Col causes negligible cytokine release as compared with murine OKT3 IgG.

These results demonstrate that OKT3_scFv-Col is more effective at immunosuppressing T cell proliferation while exhibiting negligible mitogenic activity in stimulating T cell proliferation. Thus, the soluble trimeric antibodies of the invention can have reduced mitogenicity. As a result, collagen scaffold antibody can be an ideal structure for therapeutic antibody design both in antitumor and immunomodulatory applications.

Example 11

Attachment of a Heterologous Domain to the C-Terminal Scaffold Domain

Figure 13:
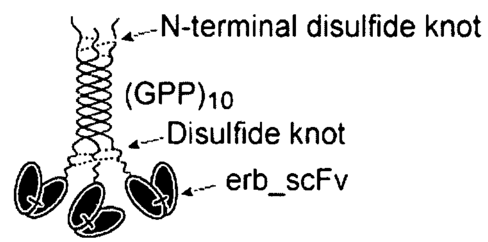
FIGS. 13 A-B depict purification of Col-erb_scFv. (A) Schematic representation of the collagen scaffold antibody, Col-erb_scFv, containing an amino-terminal disulfide knot (TCPPCPRSIP (SEQ ID NO: 24)), a collagen-like domain $(GPP)_{10}$ (SEQ ID NO: 20), followed by a carboxyl-terminal disulfide knot (GICDPSLC (SEQ ID NO: 25)) derived from the NC1 domain of type XXI collagen and an erb_scFv (anti-EGFR). (B) Purification of Col-erb_scFv. Recombinant Col-erb_scFv stably expressed in mouse myeloma NS0 cells was purified from culture media by column chromatographies. The samples were electrophoresed on a 10% SDS/Bis-Tris polyacrylamide gel with MOPS buffer under non-reducing conditions (lane 1) and reducing conditions, where sample was treated with 50 mM of DTT for 10 min at 70° C. (lane 2). The gel was stained with Imperial™ Protein Stain solution (Pierce Biotechnology, Inc.).
Figure 13:
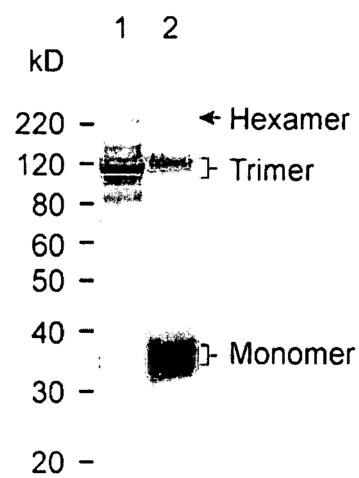

Earlier work reported that a interchain disulfide-bonded $(\text{Gly-Pro-Pro})_{10}$ (SEQ ID NO: 20) triplex can be obtained in vitro by a redox-shuffling process of a disulfide knot of type III collagen either C- or N-terminal adjacent to the collagen-like peptide at 20° C. (Frank et al., (2003) *J Biol Chem* 278: 7747-7750). To investigate whether the $(\text{Gly-Pro-Pro})_{10}$ (SEQ ID NO: 20) can drive the trimerization of a C-terminal fusion partner in vivo, a CSA molecule, Col-erb_scFv, composed of a N-terminal synthetic collagen scaffold gene coding for a peptide sequence of TCPPCPRSIP $(\text{GPP})_{10}$ GICDPSLC (SEQ ID NO: 32), and an C-terminal erb_scFv was generated (FIG. 13A). The results showed that the purified Col-erb_scFv exhibits a structure feature similar to that observed in erb_scFv-Col, except that the amount of hexamer in Col-erb_scFv is less than that of erb_scFv-Col (FIG. 13B). Therefore, the $(\text{Gly-Pro-Pro})_{10}$ (SEQ ID NO: 20) peptide scaffold by itself can drive the trimerization of a N- or C-terminal fusion partner of scFv.

Example 12

Requirements for Driving CSA Trimerization

Figure 14:
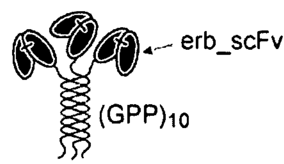
FIGS. 14 A-C depict the collagen-scaffold peptide of the CSA, comprising $(GPP)_{10}$ (SEQ ID NO: 20), by itself can drive the formation of a thermal-stable non-covalently bound trimeric fusion protein. (A) Schematic representation of the CSA, erb_scFv-$GPP_{10}$, containing an amino-terminal erb_scFv (anti-EGFR) and a collagen-like domain GSP $(GPP)_{10}$GPS (SEQ ID NO: 23). (B) Thermal stability of trimeric structure of erb_scFv-$GPP_{10}$. Purified erb_scFv-$GPP_{10}$ in 50 mM Tris-HCl (pH 8.0), containing 2 M urea, was treated in the absence (lanes 1 to 3) or presence (lanes 4 to 9) of 10 mM TCEP at ambient temperature. All samples, which had an equal amount of protein, were heated for 10 min at the indicated temperatures and then SDS-loading buffer was added immediately. The samples were electrophoresed on a 10% SDS/Bis-Tris polyacrylamide gel with MOPS buffer under non-reducing conditions. The gel was stained with Imperial™ Protein Stain solution (Pierce Biotechnology, Inc.). (C) Binding of erb_scFv-$GPP_{10}$ to EGFR-ECD by ELISA. A 96-well microtiter plate was coated with 1 μg/ml of EGFR-ECD and subsequently incubated with various concentrations of purified erb_scFv-$GPP_{10}$ and HRP conjugated anti-c-myc antibodies. Absorbance at 450 nm was measured.
Figure 14:
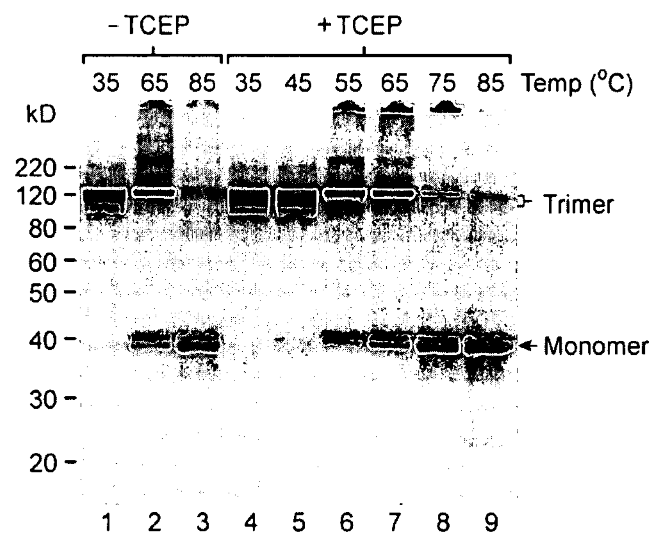
Figure 14:
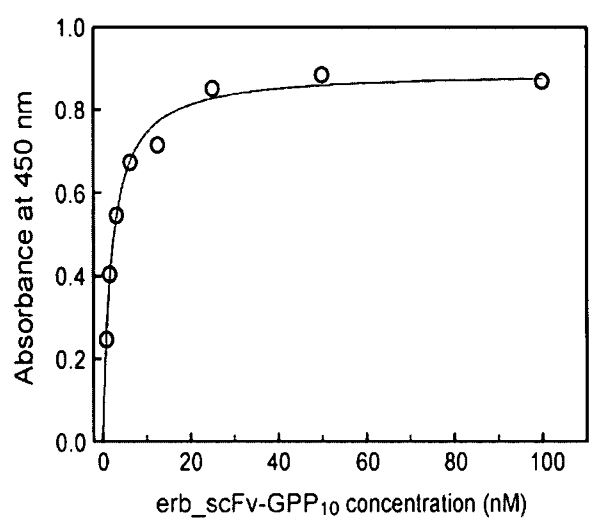

A CSA molecule, erb_scFv-$\text{GPP}_{10}$, was generated to demonstrate that the collagen-like peptide, comprising $(\text{GPP})_{10}$ (SEQ ID NO: 20), by itself can drive the formation of a non-covalently bound trimeric fusion protein, without the aid of any other trimerization domains or interchain crosslinking amino acid residues (such as Cys and Lys) present within or flanking the collagen-like domain. The coding region of erb_scFv-$\text{GPP}_{10}$ included an N-terminal nucleotide sequence of erb_scFv and a C-terminal synthetic collagen scaffold gene coding for a peptide sequence of $\text{GSP(GPP)}_{10}\text{GPSSGG}$ (SEQ ID NO: 31) (FIG. 14A). As shown in FIG. 14B, erb_scFv-$\text{GPP}_{10}$ forms a thermally stable trimer only, with a melting temperature similar to that of the reduced/alkylated interchain disulfide-bonded structure of erb_scFv-Col (FIG. 6A). Meanwhile, erb_scFv-$\text{GPP}_{10}$ retains a strong binding avidity toward EGFR-ECD, indicating that the erb_scFv is folded correctly (FIG. 14C).

Example 13

Figure 15:
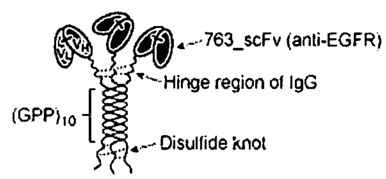
FIGS. 15 A-C depict the purification and characterization of 763_scFv-Col. (A) Schematic representation of 763_scFv-Col, containing an amino-terminal 763_scFv (anti-EGFR), a mutant hinge region of human IgG, a collagen-like domain $(GPP)_{10}$ (SEQ ID NO: 20), followed by a disulfide knot (GICDPSLC (SEQ ID NO: 25)) of type XXI collagen. (B) The antibody was stably expressed in mouse myeloma NS0 cells and purified from culture media by column chromatographies. The sample was electrophoresed on a 10% SDS/Bis-Tris polyacrylamide gel with MOPS buffer under non-reducing conditions (lane 1) and reducing conditions (lane 2). (C) The inhibition of EGF-induced tyrosine phosphorylation of EGFR by 763_scFv-Col. A431 cells were incubated with or without 16 nM EGF, in the absence or presence 763_scFv-Col (0.2-150 nM) for 30 min. Cell lysates were separated on a 10% SDS/Bis-Tris polyacrylamide gel with MOPS buffer under reducing conditions. Equal amounts of total protein from the different cell lysates were loaded in each lane. EGFR phosphorylation in cell lysates was detected by Western blotting using anti-phosphotyrosine mAb. Anti-β-actin was used as loading control. EGF-induced EGFR tyrosine phosphorylation in the absence of antibodies was designated as 100%.
Figure 15:
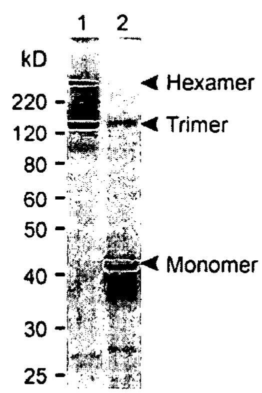
Figure 15:
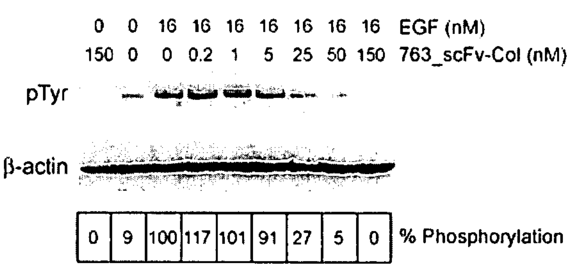
Figure 16:
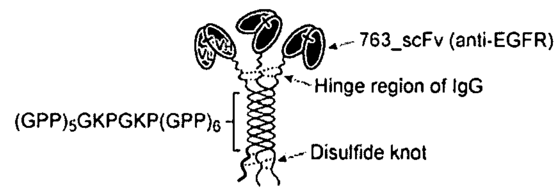
FIGS. 16 A-C depict the purification and characterization of 763_CSA2. (A) Schematic representation of 763CSA2, containing an amino-terminal 763_scFv (anti-EGFR), a mutant hinge region of human IgG, a collagen-like domain $(GPP)_5GKPGKP(GPP)_6$ (SEQ ID NO: 26), followed by a disulfide knot (GICDPSLC (SEQ ID NO: 25)) of type XXI collagen. (B) Identification of trimers. The sample was electrophoresed on a 10% SDS/Bis-Tris polyacrylamide gel with MOPS buffer under non-reducing conditions (lane 2). Lane 1, molecular weight marker. (C) Binding of 763CSA2 to EGFR by ELISA. A 96-well microtiter plate was coated with 1 μg/ml of EGFR and subsequently incubated with various concentrations of purified 763CSA2 and HRP conjugated anti-c-myc antibodies. Absorbance at 450 nm was measured.
Figure 16:
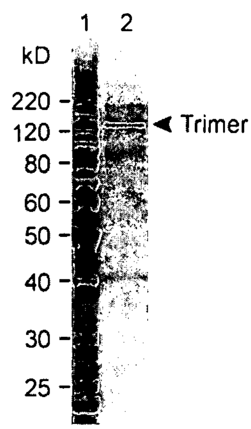
Figure 16:
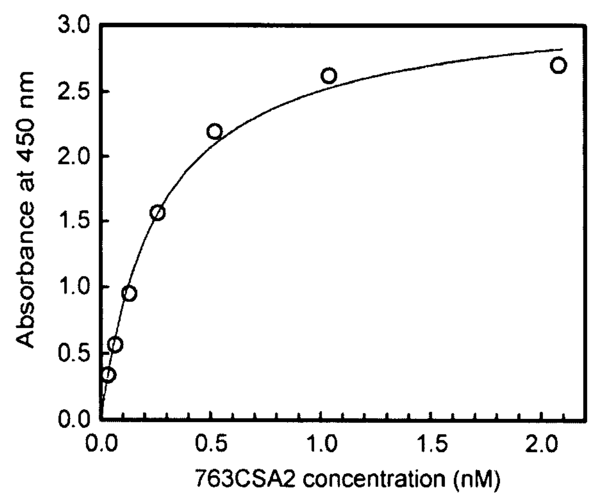

Production of CSA Molecules with Different Collagen-Like Peptides as Scaffold Domains The scFv derived from Vectibix (panitumumab; Amgen, Thousand Oaks, Calif., USA), a therapeutic fully-human anti-EGFR mAb was used to construct two different types of CSA: 763_scFv-Col and 763CSA2 with different collagen-like peptides, $(\text{GPP})_{10}$ (SEQ ID NO: 20) (FIG. 15A) and $(\text{GPP})_5\text{GKPGKP(GPP)}_6$ SEQ ID NO: 26) (FIG. 16A)), respectively as scaffold domains. Both CSAs assembled into trimers as analyzed by SDS-PAGE (FIGS. 15B and 16B). The 763_scFv-Col effectively blocked EGFR signaling at a concentration equivalent to the parental panitumumab (FIG. 15C). Meanwhile, 763CSA2 retains a strong binding avidity toward EGFR (purified from human epithelial carcinoma A431 cell line), indicating that the erb_scFv is folded correctly (FIG. 16C).

Example 14

Production of a Bispecific CSA Molecule

Figure 17:
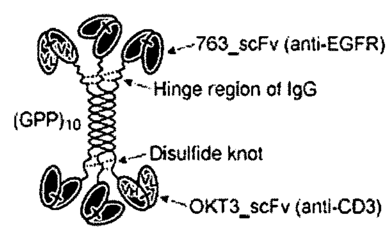
FIGS. 17 A-C depict the purification and characterization of the bispecific CSA, 763CSAOKT3. (A) Schematic representation of 763CSAOKT3, containing an amino-terminal 763_scFv (anti-EGFR), a mutant hinge region of human IgG, a collagen-like domain $(GPP)_{10}$ (SEQ ID NO: 20), followed by a disulfide knot (GICDPSLC (SEQ ID NO: 25)) of type XXI collagen and a carboxyl-terminal OKT3_scFv (anti-CD3). (B) Western blot analysis of the culture media containing recombinant bispecific 763CSAOKT3 antibody. Aliquots of 20 μl of culture media derived from four different stable clones (numbered from 1 to 4) were separated on a 10% SDS/Bis-Tris polyacrylamide gel with MOPS buffer under non-reducing and reducing conditions, and then immunoblotted with anti-c-myc mAb. The bound antibodies were detected with peroxidase-conjugated anti-mouse secondary antibodies. (C) Purification of 763CSA-OKT3. Recombinant 763CSAOKT3 stably expressed in mouse myeloma NS0 cells was purified from culture media by column chromatographies. The sample was electrophoresed on a 10% SDS/Bis-Tris polyacrylamide gel with MOPS buffer under non-reducing conditions (lane 1) and reducing conditions, where sample was treated with 50 mM of DTT for 10 min at 70° C. (lane 2). The gel was stained with Imperial™ Protein Stain solution (Pierce Biotechnology, Inc.).
Figure 17:
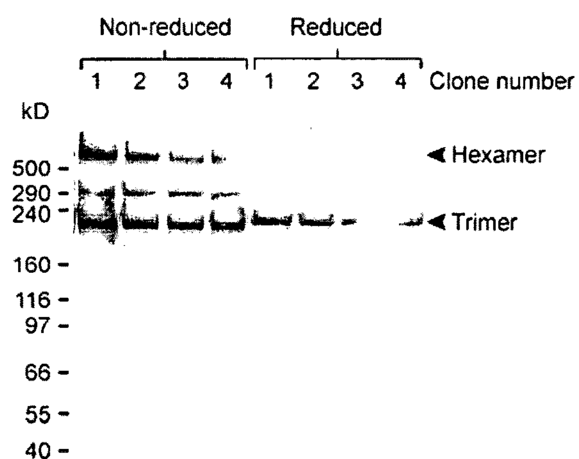
Figure 17:
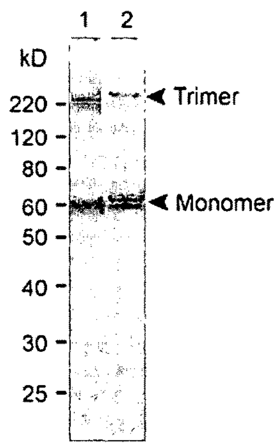

A bispecific CSA molecule, 763CSAOKT3, was generated to demonstrate that the self-trimerization collagen scaffold is more versatile in that it allows attachment of fusion partners to both termini simultaneously (FIG. 17A). The culture media containing secretory 763CSAOKT3 from four different stable clones were examined by Western blot analysis. The 763CSAOKT3 molecules were assembled into a trimeric structure and they can be further oligomerized into a hexamer, presumably through the interchain disulfide crosslinking between the two C-terminal cysteine residues within the two trimers (FIG. 17B). After purification, the major form of 763CSAOKT3 is present as a trimer under non-reducing conditions (FIG. 17C, lane 1).

Figure 18:
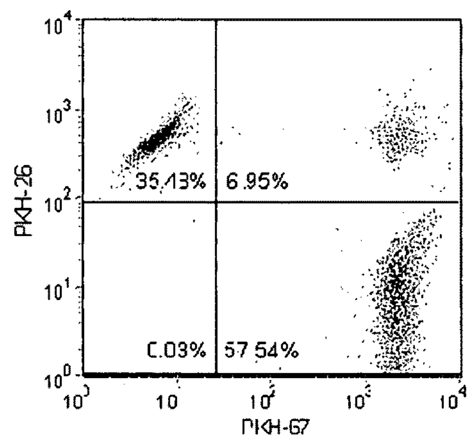
FIGS. 18 A-C depict flow cytometry analysis of the bispecific CSA, 763CSAOKT3, crosslinking A431 (EGFR-positive) and human CD3(+) T cells. Equal amounts ($1\times10^6$ cells) of PKH-67 labeled A431 cells and PKH-26 labeled CD3(+) T cells were mixed in the absence (A) or presence of 1:4 (B); 1:2 dilution (C) of culture media containing recombinant bispecific 763CSAOKT3 antibody.
Figure 18:
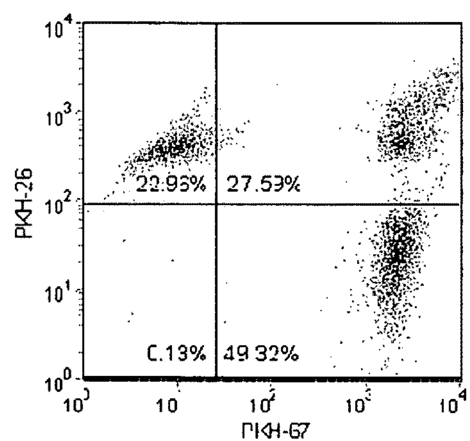
Figure 18:
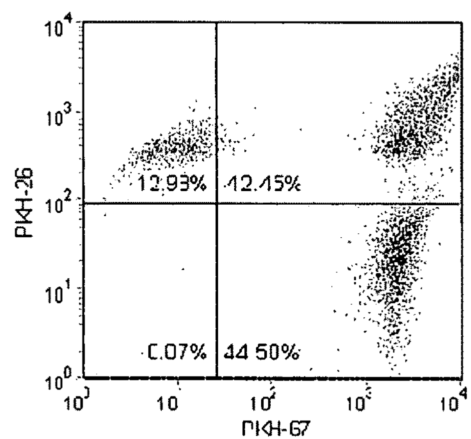

The above result has important consequences as the self-trimerization collagen scaffold may be deployed to construct molecules that are able to interact (each end with a binding valency up to 3 or 6) simultaneously with two bulky binding partners. As shown in FIG. 18, the bispecific 763CSAOKT3 can crosslink A431 (EGFR-positive) and human CD3(+) T cells. Consequently, 763CSAOKT3 can serve as a T-cell engager capable of redirecting T-cell cytotoxicity against various EGFR-expressing cancer cells.

Example 15

Production of a Bifunctional CSA Molecule

Figure 19:
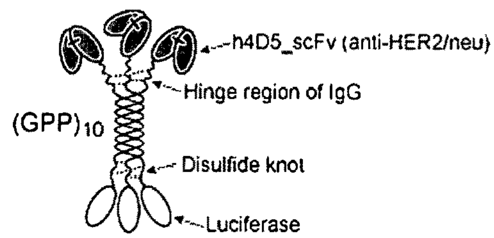
FIGS. 19 A-B depict the purification and characterization of the bifunctional CSA, h4D5CSA-Luc. (A) Schematic representation of h4D5CSA-Luc, containing an amino-terminal h4D5_scFv (anti-HER2/neu), a mutant hinge region of human IgG, a collagen-like domain $(GPP)_{10}$ (SEQ ID NO: 20), followed by a disulfide knot (GICDPSLC (SEQ ID NO: 25)) of type XXI collagen and a carboxyl-terminal *Gaussia* luciferase. (B) Purification of h4D5CSA-Luc. Recombinant h4D5CSA-Luc stably expressed in mouse myeloma NS0 cells was purified from culture media by column chromatographies. The sample was electrophoresed on a 10% SDS/Bis-Tris polyacrylamide gel with MOPS buffer under non-reducing conditions (lane 2) and reducing conditions, where sample was treated with 50 mM of DTT for 10 min at 70° C. (lane 3). The gel was stained with Imperial™ Protein Stain solution (Pierce Biotechnology, Inc.). Lane 1, molecular weight marker. (C) Binding of h4D5CSA-Luc to HER2/neu overexpressed SKOV-3 cells by ELISA. A 96-well microplate was coated with $5\times10^4$ cells/well and was incubated with two-fold serial dilution of purified h4D5CSA-Luc. After washing plate with PBS/1% BSA, the bound antibodies were detected by addition of coelenterazine and the bioluminescence values were acquired using a microplate-luminometer. Samples were assayed in triplicate.
Figure 19:
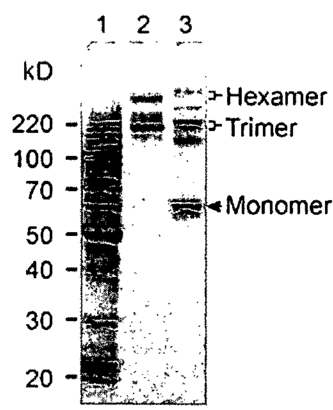
Figure 19:
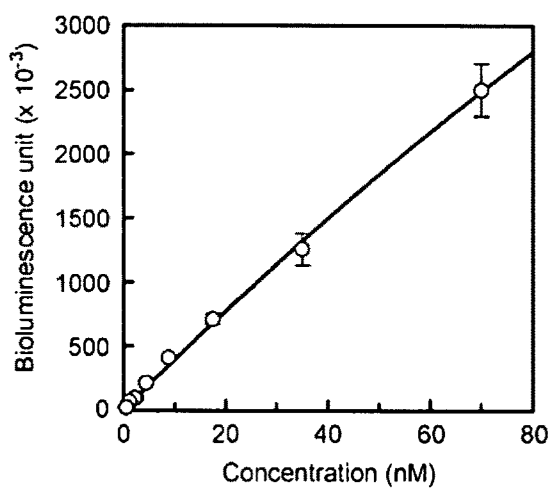

A bifunction CSA molecule, h4D5CSA-Luc, was generated as depicted in FIG. 19A. The culture media containing secretory h4D5CSA-Luc was purified by chromatographies. The h4D5CSA-Luc molecules were assembled into a trimeric structure and they can be further oligomerized into a hexamer, presumably through the interchain disulfide crosslinking between the two C-terminal cysteine residues within the two trimers (FIG. 19B). A bioluminescence ELISA was performed to demonstrate that the h4D5CSA-Luc retained both HER2/neu binding and bioluminescence activities. As shown in FIG. 19C, purified h4D5CSA-Luc captured in wells coated with HER2/neu overexpressing human ovarian SKOV-3 carcinoma cells retained the ability to catalyze coelenterazine and emit light in a concentration dependent manner.

The above result has important consequences as the self-trimerization collagen scaffold may be deployed to construct molecules that are able to interact (each end with a binding valency up to 3 or 6) with a binding partner and the interaction can be detected directly by incubating the C-terminal luciferase domain of the bifunctional CSA molecule with bioluminescent substrate. Presumably, h4D5CSA-Luc can serve as a reagent for molecular diagnostics or optical imaging.

Example 16

Production of an Anti-TNF-α CSA

Figure 20:
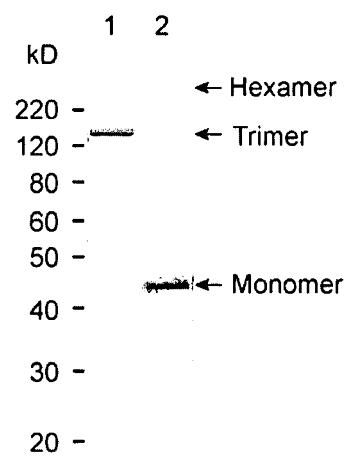
FIGS. 20 A-B depict the purification and characterization of 357_scFv-Col. (A) The antibody was stably expressed in mouse myeloma NS0 cells and purified from culture media by column chromatographies. The sample was electrophoresed on a 10% SDS/Bis-Tris polyacrylamide gel with MOPS buffer under non-reducing conditions (lane 1) and reducing conditions (lane 2). (B) Neutralization of TNF-α-induced apoptosis of L929 cells by 357_scFv-Col and 357 IgG. L929 mouse fibroblast cells ($5\times10^3$ cells) were incubated with different concentration of either 357_scFv-Col or 357 IgG, containing 2 μg/ml of actinomycin D and 10 ng/ml of human recombinant TNF-α for 24 h. TNF-α induced cell cytotoxicity was determined by MTT assay. The number of viable cells was determined by measuring the optical densities at 460 nm. The neutralization of TNF-α by antibody was calculated using the formula % Neutralization=100× ($Cytotoxicity_{ctrl}$−$Cytotoxicity_{Ab}$)/$Cytotoxicity_{ctrl}$; % Cytotoxicity=100×($A_{ctrl}$−$A_{test}$)/$A_{ctrl}$, where $A_{ctrl}$ was the absorbance in control wells (without TNF-α) and $A_{test}$ was the absorbance in wells with TNF-α ($Cytotoxicity_{ctrl}$) or TNF-α plus antibody ($Cytotoxicity_{Ab}$).
Figure 20:
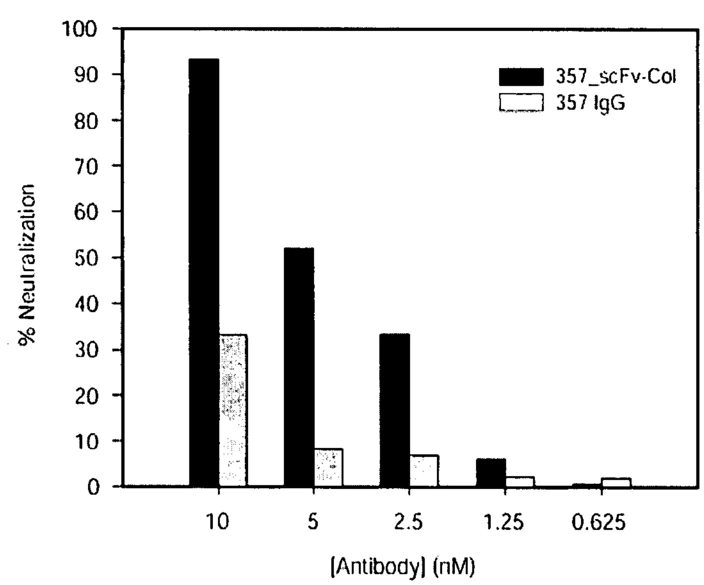

The scFv derived from the hybridoma 357-101-4 cell line (ECACC No. 92030603), a mouse anti-human TNF-α mAb with strong neutralizing activities was used to construct a CSA molecule, 357scFv-Col. The purified 357_scFv-Col exhibits a structure feature similar to that observed in the format of scFv-Col (FIG. 20A). The degree of neutralization of TNF-α-induced apoptosis of L929 cells by 357_scFv-Col and 357 IgG was compared. As shown in FIG. 20B, the 357_scFv-Col exhibits a neutralizing activity about 4-fold stronger than the bivalent 357 IgG.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

REFERENCES

Bachinger, H. P., Bruckner, P., Timpl, R., Prockop, D. J., and Engel, J. (1980). Folding mechanism of the triple helix in type-III collagen and type-III pN-collagen. Role of disulfide bridges and peptide bond isomerization. Eur J Biochem 106, 619-632.

Berg, R. A., and Prockop, D. J. (1973). The thermal transition of a non-hydroxylated form of collagen. Evidence for a role for hydroxyproline in stabilizing the triple-helix of collagen. Biochem Biophys Res Commun 52, 115-120.

Binz, H. K., Amstutz, P., Kohl, A., Stumpp, M. T., Briand, C., Forrer, P., Grutter, M. G., and Pluckthun, A. (2004). High-affinity binders selected from designed ankyrin repeat protein libraries. Nat Biotechnol 22, 575-582.

Binz, H. K., Amstutz, P., and Pluckthun, A. (2005). Engineering novel binding proteins from nonimmunoglobulin domains. Nat Biotechnol 23, 1257-1268.

Boudko, S., Frank, S., Kammerer, R. A., Stetefeld, J., Schulthess, T., Landwehr, R., Lustig, A., Bachinger, H. P., and Engel, J. (2002). Nucleation and propagation of the collagen triple helix in single-chain and trimerized peptides: transition from third to first order kinetics. J Mol Biol 317, 459-470.

Carter, P., Presta, L., Gorman, C. M., Ridgway, J. B., Henner, D., Wong, W. L., Rowland, A. M., Kotts, C., Carver, M. E., and Shepard, H. M. (1992). Humanization of an anti-p185HER2 antibody for human cancer therapy. Proc Natl Acad Sci USA 89, 4285-4289.

Chopra, R. K., and Ananthanarayanan, V. S. (1982). Conformational implications of enzymatic proline hydroxylation in collagen. Proc Natl Acad Sci USA 79, 7180-7184.

Chou, M. Y, and Li, H. C. (2002). Genomic organization and characterization of the human type XXI collagen (COL21A1) gene. Genomics 79, 395-401.

Dubel, S., Breitling, F., Kontermann, R., Schmidt, T., Skerra, A., and Little, M. (1995). Bifunctional and multimeric complexes of streptavidin fused to single-chain antibodies (scFv). J Immunol Methods 178, 201-209.

Engel, J., Chen, H. T., Prockop, D. J., and Klump, H. (1977). The triple helix in equilibrium with coil conversion of collagen-like polytripeptides in aqueous and nonaqueous solvents. Comparison of the thermodynamic parameters and the binding of water to (L-Pro-L-Pro-Gly)n and (L-Pro-L-Hyp-Gly)n. Biopolymers 16, 601-622.

Fietzek, P. P., and Kuhn, K. (1976). The primary structure of collagen. Int Rev Connect Tissue Res 7, 1-60.

Frank, S., Boudko, S., Mizuno, K., Schulthess, T., Engel, J., and Bachinger, H. P. (2003). Collagen triple helix formation can be nucleated at either end. J Biol Chem 278, 7747-7750.

Frank, S., Kammerer, R. A., Mechling, D., Schulthess, T., Landwehr, R., Bann, J., Guo, Y, Lustig, A., Bachinger, H. P., and Engel, J. (2001). Stabilization of short collagen-like triple helices by protein engineering. J Mol Biol 308, 1081-1089.

Graversen, J. H., Jacobsen, C., Sigurskjold, B. W., Lorentsen, R. H., Moestrup, S. K., Thogersen, H. C., and Etzerodt, M. (2000). Mutational analysis of affinity and selectivity of kringle-tetranectin interaction. Grafting novel kringle affinity ontp the tetranectin lectin scaffold. J Biol Chem 275, 37390-37396.

Hakansson, K., Lim, N. K., Hoppe, H. J., and Reid, K. B. (1999). Crystal structure of the trimeric alpha-helical coiled-coil and the three lectin domains of human lung surfactant protein D. Structure 7, 255-264.

Hakansson, K., and Reid, K. B. (2000). Collectin structure: a review. Protein Sci 9, 1607-1617.

Harbury, P. B., Zhang, T., Kim, P. S., and Alber, T. (1993). A switch between two-, three-, and four-stranded coiled coils in GCN4 leucine zipper mutants. Science 262, 1401-1407.

Holler, N., Tardivel, A., Kovacsovics-Bankowski, M., Hertig, S., Gaide, O., Martinon, F., Tinel, A., Deperthes, D., Calderara, S., Schulthess, T., et al. (2003). Two adjacent trimeric Fas ligands are required for Fas signaling and formation of a death-inducing signaling complex. Mol Cell Biol 23, 1428-1440.

Holliger, P., and Hudson, P. J. (2005). Engineered antibody fragments and the rise of single domains. Nat Biotechnol 23, 1126-1136.

Hoppe, H. J., Barlow, P. N., and Reid, K. B. (1994). A parallel three stranded alpha-helical bundle at the nucleation site of collagen triple-helix formation. FEBS Lett 344, 191-195.

Ito, W., and Kurosawa, Y. (1993). Development of an artificial antibody system with multiple valency using an Fv fragment fused to a fragment of protein A. J Biol Chem 268, 20668-20675.

Kivirikko, K. I., Myllyla, R., and Pihlajaniemi, T. (1992). Hydroxylation of proline and lysine residues in collagens and other animal and plant proteins. In Post-Translational Modifications of Proteins (Harding, J. J., and Crabbe, M. J. C., Eds.). CRC Press, Boca Raton, Fla., 1-51.

Li, H. C., Huang, C. C., Chen, S. F., and Chou, M. Y (2005). Assembly of homotrimeric type XXI minicollagen by coexpression of prolyl 4-hydroxylase in stably transfected *Drosophila melanogaster* S2 cells. Biochem Biophys Res Commun 336, 375-385.

Lynn, A. K., Yannas, I. V., and Bonfield, W. (2004). Antigenicity and immunogenicity of collagen. J Biomed Mater Res B Appl Biomater 71, 343-354.

Mazzorana, M., Cogne, S., Goldschmidt, D., and Aubert-Foucher, E. (2001). Collagenous sequence governs the trimeric assembly of collagen XII. J Biol Chem 276, 27989-27998.

Mohs, A., Silva, T., Yoshida, T., Amin, R., Lukomski, S., Inouye, M., and Brodsky, B. (2007). Mechanism of stabilization of a bacterial collagen triple helix in the absence of hydroxyproline. J. Biol. Chem. 282, 29757-29765.

Nord, K., Gunneriusson, E., Ringdahl, J., Stahl, S., Uhlen, M., and Nygren, P. A. (1997). Binding proteins selected from combinatorial libraries of an alpha-helical bacterial receptor domain. Nat Biotechnol 15, 772-777.

Persikov, A. V., Xu, Y., and Brodsky, B. (2004). Equilibrium thermal transitions of collagen model peptides. Protein Sci. 13:893-902.

Persikov, A. V., Ramshaw, J. A. M., Kirkpatrick, A., and Brodsky, B. (2000). Amino acid propensities for the collagen triple-helix. Biochemistry 39, 14960-14967.

Prockop, D. J., and Kivirikko, K. I. (1995). Collagens: molecular biology, diseases, and potentials for therapy. Annu Rev Biochem 64, 403-434.

Queen, C., Schneider, W. P., Selick, H. E., Payne, P. W., Landolfi, N. F., Duncan, J. F., Avdalovic, N. M., Levitt, M., Junghans, R. P., and Waldmann, T. A. (1989). A humanized antibody that binds to the interleukin 2 receptor. Proc Natl Acad Sci USA 86, 10029-10033.

Rheinnecker, M., Hardt, C., Ilag, L. L., Kufer, P., Gruber, R., Hoess, A., Lupas, A., Rottenberger, C., Pluckthun, A., and Pack, P. (1996). Multivalent antibody fragments with high functional affinity for a tumor-associated carbohydrate antigen. J Immunol 157, 2989-2997.

Riechmann, L., Clark, M., Waldmann, H., and Winter, G. (1988). Reshaping human antibodies for therapy. Nature 332, 323-327.

Rosenbloom, J., Harsch, M., and Jimenez, S. (1973). Hydroxyproline content determines the denaturation temperature of chick tendon collagen. Arch Biochem Biophys 158, 478-484.

Sakakibara, S., Inouye, K., Shudo, K., Kishida, Y., Kobayashi, Y., and Prockop, D. J. (1973). Synthesis of (Pro-Hyp-Gly)n of defined molecular weights. Evidence for the stabilization of collagen triple helix by hydroxypyrroline. Biochim Biophys Acta 303, 198-202.

Shaw, L. M., and Olsen, B. R. (1991). FACIT collagens: diverse molecular bridges in extracellular matrices. Trends Biochem Sci 16, 191-194.

Sheriff, S., Chang, C. Y., and Ezekowitz, R. A. (1994). Human mannose-binding protein carbohydrate recognition domain trimerizes through a triple alpha-helical coiled-coil. Nat Struct Biol 1, 789-794.

Skerra, A. (2000). Lipocalins as a scaffold. Biochim Biophys Acta 1482, 337-350.

Weis, W. I., and Drickamer, K. (1994). Trimeric structure of a C-type mannose-binding protein. Structure 2, 1227-1240.

Yang, W., Chan, V. C., Kirkpatrick, A., Ramshaw, J. A., and Brodsky, B. (1997). Gly-Pro-Arg confers stability similar to Gly-Pro-Hyp in the collagen triple-helix of host-guest peptides. J Biol Chem 272, 28837-28840.

We claim:

1. A trimeric soluble antibody comprising three polypeptides, wherein each polypeptide comprises:

(a) a collagen scaffold domain comprising $(G\text{-}P\text{-}P)_{10}$ (SEQ ID NO: 20), wherein G is glycine, P is proline, and at least 6 of the G-P-P repeats are hydroxyprolinated at the second proline; and (b) an antibody domain that binds to a ligand;

wherein the polypeptide does not comprise a separate trimerization domain.

2. The trimeric soluble antibody of claim 1, wherein the ligand for the trimeric soluble antibody is human epidermal growth factor receptor.

3. The trimeric soluble antibody of claim 1, wherein the ligand for the trimeric soluble antibody is human CD3.

4. The trimeric soluble antibody of claim 1, wherein the ligand for the trimeric soluble antibody is human TNF-α.

5. The trimeric soluble antibody of claim 2, wherein the antibody is a bispecific antibody.

6. The trimeric soluble antibody of claim 1, wherein the polypeptide further comprises a coding sequence for a marker polypeptide.

7. The trimeric soluble antibody of claim 6, wherein the marker polypeptide is a luciferase polypeptide or a green fluorescent polypeptide.

8. The trimeric soluble antibody of claim 1, wherein each polypeptide comprises two antibody domains.

9. The trimeric soluble antibody of claim 1, wherein each polypeptide further comprises an affinity tag.

10. The trimeric soluble antibody of claim 1, wherein the antibody domain comprises the sequence of a single chain antibody.

11. The trimeric soluble antibody of claim 1, wherein the first, second, and third polypeptides are substantially identical.

12. The trimeric soluble antibody of claim 1, wherein the antibody domain is obtained by phage display screening.

13. The trimeric soluble antibody of claim 1, wherein the antibody domain comprises the sequence of a single chain antibody and further comprises a hinge region and a coding sequence for luciferase.

14. The trimeric soluble antibody of claim 1, wherein the antibody domain comprises the sequence of an immunoglobulin.

15. The trimeric soluble antibody of claim 1, wherein the antibody domain comprises a chimeric scFv-Fc antibody which comprises the sequence of a single chain antibody and a constant region (Fc).

16. The trimeric soluble antibody of claim 1, wherein the antibody domain comprises the sequence of an Fab domain and further comprises a hinge region.

17. The trimeric soluble antibody of claim 16, wherein the ligand for the trimeric soluble antibody is human CD3.

18. The trimeric soluble antibody of claim 1, wherein the antibody domain comprises the sequence of an Fab domain and further comprises a hinge region and a coding sequence for luciferase.

19. A trimeric protein complex comprising three polypeptides, wherein each polypeptide comprises:

(a) a self-trimerizing triple helix coil scaffold domain comprising (G-P-P) (SEQ ID NO: 20), wherein G is glycine, P is proline, and at least 6 of the G-P-P repeats are hydroxyprolinated at the second proline, and wherein the self-trimerizing scaffold domain does not comprise a separate trimerization domain; and (b) a first heterologous domain in-frame fused to one end of the scaffold domain, wherein the first heterologous domain is a binding domain selected from the group consisting of an antibody domain, a ligand binding domain, a ligand, a receptor, and a proteoglycan, or which is a fluorescent protein or an enzymatic domain.

20. The protein complex of claim 19, wherein each polypeptide further comprises a second heterologous domain in-frame fused to the other end of the scaffold domain, wherein the second heterologous domain is a binding domain selected from the group consisting of an antibody domain, a ligand binding domain, a ligand, a receptor, and a proteoglycan, or which is a fluorescent protein or an enzymatic domain; wherein the triple helix coil scaffold domains of the three polypeptides interact with each other to form a trimeric protein complex.

21. The protein complex of claim 19, wherein the heterologous domain is an antibody domain.

22. The protein complex of claim 21, wherein the scaffold domain is in-frame fused to the amino terminus of the antibody domain.

23. The protein complex of claim 21, wherein the scaffold domain is in-frame fused to the carboxy terminus of the antibody domain.

24. The protein complex of claim 21, wherein the antibody domain comprises one or more complementarity-determining regions of an immunoglobulin.

25. The protein complex of claim 24, wherein the antibody domain comprises the sequence of an antigen-binding fragment.

26. The protein complex of claim 25, wherein the antigen-binding fragment specifically binds to CD3.

27. The protein complex of claim 25, wherein the antigen-binding fragment specifically binds to epidermal growth factor receptor (EGFR).

28. The protein complex of claim 26, wherein the antigen-binding fragment comprises a single chain antibody.

29. The protein complex of claim 21, wherein each polypeptide further comprises a second heterologous domain comprising a second antibody domain.

30. The protein complex of claim 29, wherein the first antibody domain comprises a first single chain antibody that specifically binds to CD3.

31. The protein complex of claim 29, wherein the second antibody domain comprises a second single chain antibody that specifically binds EGFR.

32. The protein complex of claim 30, wherein the second antibody domain comprises a second single chain antibody that specifically binds EGFR.

33. The protein complex of claim 20, wherein the second heterologous domain of at least one of the polypeptides further comprises an enzymatic domain or a fluorescent protein.

34. The protein complex of claim 20, wherein the three polypeptides are substantially identical.

35. A trimeric soluble antibody comprising three polypeptides, wherein each polypeptide comprises:

(a) a collagen scaffold domain comprising $GSP(GPP)_{10}GPSSGG$ (SEQ ID NO: 13); and (b) an antibody domain;

wherein the polypeptide does not comprise a separate trimerization domain.

* * * * *

SEQUENCE LISTING

```
<160> NUMBER OF SEQ ID NOS: 33

<210> SEQ ID NO 1
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Asp Ile Gly Ala Ser Gly Ser Ala Thr Ser Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Thr Thr Thr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Asp Ala Ser Ala Leu Gln Ser Gly Val
            180                 185                 190

Pro Ser Arg Phe Ser Gly Ser Gly Ser Gly Thr Asp Phe Thr Leu Thr
```

```
        195                 200                 205

Ile Ser Ser Leu Gln Pro Glu Asp Phe Ala Thr Tyr Tyr Cys Gln Gln
    210                 215                 220

Tyr Ala Asp Tyr Pro Thr Thr Phe Gly Gln Gly Thr Lys Val Glu Ile
225                 230                 235                 240

Lys Arg


<210> SEQ ID NO 2
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

atggccgagg tgcagctgtt ggagtctggg ggaggcttgg tacagcctgg ggggtccctg     60

agactctcct gtgcagcctc tggattcacc tttagcagct atgccatgag ctgggtccgc    120

caggctccag ggaaggggct ggagtgggtc tcagatattg gtgcttctgg ttctgctaca    180

tcttacgcag actccgtgaa gggccggttc accatctcca gagacaattc caagaacacg    240

ctgtatctgc aaatgaacag cctgagagcc gaggacacgg ccgtatatta ctgtgcgaaa    300

tctactacta cttttgacta ctggggccag ggaaccctgg tcaccgtctc gagcggtgga    360

ggcggttcag gcggaggtgg cagcggcggt ggcgggtcga cggacatcca gatgacccag    420

tctccatcct ccctgtctgc atctgtagga gacagagtca ccatcacttg ccgggcaagt    480

cagagcatta gcagctattt aaattggtat cagcagaaac cagggaaagc ccctaagctc    540

ctgatctatg atgcatccgc tttgcaaagt ggggtcccat caaggttcag tggcagtgga    600

tctgggacag atttcactct caccatcagc agtctgcaac ctgaagattt tgcaacttac    660

tactgtcaac agtatgctga ttatcctact acgttcggcc aagggaccaa ggtggaaatc    720

aaacgg                                                               726


<210> SEQ ID NO 3
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Gln Leu Gln Gln Ser Gly Ala Glu Leu Ala Arg Pro Gly Ala Ser
1               5                   10                  15

Val Lys Met Ser Cys Lys Ala Ser Gly Tyr Thr Phe Thr Arg Tyr Thr
            20                  25                  30

Met His Trp Val Lys Gln Arg Pro Gly Gln Gly Leu Glu Trp Ile Gly
        35                  40                  45

Tyr Ile Asn Pro Ser Arg Gly Tyr Thr Asn Tyr Asn Gln Lys Phe Lys
    50                  55                  60

Asp Lys Ala Thr Leu Thr Thr Asp Lys Ser Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Tyr Tyr Asp Asp His Tyr Cys Leu Asp Tyr Trp Gly Gln Gly Thr
            100                 105                 110
```

```
Thr Val Thr Val Ser Ser Gly Gly Gly Gly Ser Gly Gly Gly Gly Ser
        115                 120                 125

Gly Gly Gly Gly Ser Asp Ile Val Leu Thr Gln Ser Pro Ala Ile Met
    130                 135                 140

Ser Ala Ser Pro Gly Glu Lys Val Thr Met Thr Cys Ser Ala Ser Ser
145                 150                 155                 160

Ser Val Ser Tyr Met Asn Trp Tyr Gln Gln Lys Ser Gly Thr Ser Pro
                165                 170                 175

Lys Arg Trp Ile Tyr Asp Thr Ser Lys Leu Ala Ser Gly Val Pro Ala
            180                 185                 190

His Phe Arg Gly Ser Gly Ser Gly Thr Ser Tyr Ser Leu Thr Ile Ser
        195                 200                 205

Gly Met Glu Ala Glu Asp Ala Ala Thr Tyr Tyr Cys Gln Gln Trp Ser
    210                 215                 220

Ser Asn Pro Phe Thr Phe Gly Ser Gly Thr Lys Leu Glu Leu Lys Arg
225                 230                 235                 240


<210> SEQ ID NO 4
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

gtccagctgc agcagtcagg ggctgaactg gcaagacctg gggcctcagt gaagatgtcc     60

tgcaaggctt ctggctacac ctttactagg tacacgatgc actgggtaaa acagaggcct    120

ggacagggtc tggaatggat tggatacatt aatcctagcc gtggttatac taattacaat    180

cagaagttca aggacaaggc cacattgact acagacaaat cctccagcac agcctacatg    240

caactgagca gcctgacatc tgaggactct gcagtctatt actgtgcaag atattatgat    300

gatcattact gccttgacta ctggggccaa gggaccacgg tcaccgtctc ctcaggtgga    360

ggcggttcag gcggaggtgg ctctggcggt ggcggatcgg acattgtgct aacccagtct    420

ccagcaatca tgtctgcatc tccaggggag aaggtcacca tgacctgcag tgccagctca    480

agtgtaagtt acatgaactg gtaccagcag aagtcaggca cctcccccaa aagatggatt    540

tatgacacat ccaaactggc ttctggagtc cctgctcact tcaggggcag tgggtctggg    600

acctcttact ctctcacaat cagcggcatg gaggctgaag atgctgccac ttattactgc    660

cagcagtgga gtagtaaccc attcacgttc ggctcgggga ccaagctgga gctgaaacga    720


<210> SEQ ID NO 5
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Val Lys Leu Gln Glu Ser Gly Ser Glu Met Ala Arg Pro Gly Ala Ser
1               5                   10                  15

Val Lys Leu Pro Cys Lys Ala Ser Gly Asp Thr Phe Thr Ser Tyr Trp
            20                  25                  30

Met His Trp Val Lys Gln Arg His Gly His Gly Pro Glu Trp Ile Gly
        35                  40                  45
```

```
Asn Ile Tyr Pro Gly Ser Gly Gly Thr Asn Tyr Ala Glu Lys Phe Lys
    50                  55                  60

Asn Lys Val Thr Leu Thr Val Asp Arg Ser Ser Arg Thr Val Tyr Met
65                  70                  75                  80

His Leu Ser Arg Leu Thr Ser Glu Asp Phe Ala Val Tyr Tyr Cys Thr
                85                  90                  95

Arg Ser Gly Gly Pro Tyr Phe Phe Asp Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Met Thr Gln Thr Pro Leu Ser Leu Pro Val Ser Leu
    130                 135                 140

Gly Asp Gln Ala Ser Ile Ser Cys Arg Ser Ser Gln Asn Ile Val His
145                 150                 155                 160

Asn Asn Gly Ile Thr Tyr Leu Glu Trp Tyr Leu Gln Arg Pro Gly Gln
                165                 170                 175

Ser Pro Lys Leu Leu Ile Tyr Lys Val Ser Asp Arg Phe Ser Gly Val
            180                 185                 190

Pro Asp Arg Phe Ser Gly Ser Gly Ser Gly Thr Asp Phe Thr Leu Lys
        195                 200                 205

Ile Ser Arg Val Glu Ala Glu Asp Leu Gly Ile Tyr Tyr Cys Phe Gln
    210                 215                 220

Gly Ser His His Pro Pro Thr Phe Gly Gly Gly Thr Lys Leu Glu
225                 230                 235
```

<210> SEQ ID NO 6
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
gtcaagctgc aggagtcagg gtctgagatg gcgaggcctg gagcttcagt gaagctgccc     60

tgcaaggctt ctggcgacac attcaccagt tactggatgc actgggtgaa gcagaggcat    120

ggacatggcc ctgagtggat cggaaatatt tatccaggta gtggtggtac taactacgct    180

gagaagttca agaacaaggt cactctgact gtagacaggt cctcccgcac agtctacatg    240

cacctcagca ggctgacatc tgaggacttt gcggtctatt attgtacaag atcgggggt     300

ccctacttct ttgactactg gggccaaggg accacggtca ccgtctcctc aggtggaggc    360

ggttcaggcg gaggtggctc tggcggtggc ggatcgatga cccaaactcc actctccctg    420

cctgtcagtc ttggagatca agcctccatc tcttgcagat ctagtcagaa cattgtacat    480

aataatggaa tcacctattt agaatggtac ctgcaaaggc caggccagtc tccaaagctc    540

ctgatctaca aagtttccga ccgattttct ggggtcccag acaggttcag tggcagtgga    600

tcagggacag atttcacact caagatcagc agagtagagg ctgaggatct gggaatttat    660

tactgctttc aaggttcaca tcatcctccc acgttcggcg gggggaccaa gctggaa       717
```

<210> SEQ ID NO 7
<211> LENGTH: 150
<212> TYPE: PRT
<213> ORGANISM: Homo sapiens
<220> FEATURE:
<221> NAME/KEY: MOD_RES
<222> LOCATION: (5)..(5)

```
<223> OTHER INFORMATION: Pro or Hyp
<220> FEATURE:
<221> NAME/KEY: MOD_RES
<222> LOCATION: (15)..(16)
<223> OTHER INFORMATION: Pro or Hyp
<220> FEATURE:
<221> NAME/KEY: MOD_RES
<222> LOCATION: (18)..(18)
<223> OTHER INFORMATION: Pro or Hyp
<220> FEATURE:
<221> NAME/KEY: MOD_RES
<222> LOCATION: (22)..(22)
<223> OTHER INFORMATION: Pro or Hyp
<220> FEATURE:
<221> NAME/KEY: MOD_RES
<222> LOCATION: (24)..(25)
<223> OTHER INFORMATION: Pro or Hyp
<220> FEATURE:
<221> NAME/KEY: MOD_RES
<222> LOCATION: (27)..(27)
<223> OTHER INFORMATION: Pro or Hyp
<220> FEATURE:
<221> NAME/KEY: MOD_RES
<222> LOCATION: (30)..(30)
<223> OTHER INFORMATION: Pro or Hyp
<220> FEATURE:
<221> NAME/KEY: MOD_RES
<222> LOCATION: (33)..(33)
<223> OTHER INFORMATION: Pro or Hyp
<220> FEATURE:
<221> NAME/KEY: MOD_RES
<222> LOCATION: (37)..(37)
<223> OTHER INFORMATION: Pro or Hyp
<220> FEATURE:
<221> NAME/KEY: MOD_RES
<222> LOCATION: (40)..(40)
<223> OTHER INFORMATION: Pro or Hyp
<220> FEATURE:
<221> NAME/KEY: MOD_RES
<222> LOCATION: (46)..(46)
<223> OTHER INFORMATION: Pro or Hyp
<220> FEATURE:
<221> NAME/KEY: MOD_RES
<222> LOCATION: (52)..(52)
<223> OTHER INFORMATION: Pro or Hyp
<220> FEATURE:
<221> NAME/KEY: MOD_RES
<222> LOCATION: (55)..(55)
<223> OTHER INFORMATION: Pro or Hyp
<220> FEATURE:
<221> NAME/KEY: MOD_RES
<222> LOCATION: (64)..(64)
<223> OTHER INFORMATION: Pro or Hyp
<220> FEATURE:
<221> NAME/KEY: MOD_RES
<222> LOCATION: (78)..(78)
<223> OTHER INFORMATION: Pro or Hyp
<220> FEATURE:
<221> NAME/KEY: MOD_RES
<222> LOCATION: (83)..(84)
<223> OTHER INFORMATION: Pro or Hyp
<220> FEATURE:
<221> NAME/KEY: MOD_RES
<222> LOCATION: (86)..(87)
<223> OTHER INFORMATION: Pro or Hyp
<220> FEATURE:
<221> NAME/KEY: MOD_RES
<222> LOCATION: (89)..(89)
<223> OTHER INFORMATION: Pro or Hyp
<220> FEATURE:
<221> NAME/KEY: MOD_RES
<222> LOCATION: (92)..(93)
<223> OTHER INFORMATION: Pro or Hyp
<220> FEATURE:
<221> NAME/KEY: MOD_RES
<222> LOCATION: (100)..(101)
<223> OTHER INFORMATION: Pro or Hyp
<220> FEATURE:
<221> NAME/KEY: MOD_RES
```

```
<222> LOCATION: (104)..(104)
<223> OTHER INFORMATION: Pro or Hyp
<220> FEATURE:
<221> NAME/KEY: MOD_RES
<222> LOCATION: (107)..(107)
<223> OTHER INFORMATION: Pro or Hyp
<220> FEATURE:
<221> NAME/KEY: MOD_RES
<222> LOCATION: (116)..(116)
<223> OTHER INFORMATION: Pro or Hyp
<220> FEATURE:
<221> NAME/KEY: MOD_RES
<222> LOCATION: (122)..(122)
<223> OTHER INFORMATION: Pro or Hyp
<220> FEATURE:
<221> NAME/KEY: MOD_RES
<222> LOCATION: (124)..(125)
<223> OTHER INFORMATION: Pro or Hyp
<220> FEATURE:
<221> NAME/KEY: MOD_RES
<222> LOCATION: (130)..(130)
<223> OTHER INFORMATION: Pro or Hyp
<220> FEATURE:
<221> NAME/KEY: MOD_RES
<222> LOCATION: (142)..(142)
<223> OTHER INFORMATION: Pro or Hyp
<220> FEATURE:
<221> NAME/KEY: MOD_RES
<222> LOCATION: (147)..(147)
<223> OTHER INFORMATION: Pro or Hyp

<400> SEQUENCE: 7

Gly Gly Arg Glu Xaa Lys Ser Cys Asp Lys Thr His Thr Cys Xaa Xaa
1               5                   10                  15

Cys Xaa Arg Ser Ile Xaa Gly Xaa Xaa Gly Xaa Ile Gly Xaa Glu Gly
            20                  25                  30

Xaa Arg Gly Leu Xaa Gly Leu Xaa Gly Arg Asp Gly Val Xaa Gly Leu
        35                  40                  45

Val Gly Val Xaa Gly Arg Xaa Gly Val Arg Gly Leu Lys Gly Leu Xaa
    50                  55                  60

Gly Arg Asn Gly Glu Lys Gly Ser Gln Gly Phe Gly Tyr Xaa Gly Glu
65                  70                  75                  80

Gln Gly Xaa Xaa Gly Xaa Xaa Gly Xaa Glu Gly Xaa Xaa Gly Ile Ser
                85                  90                  95

Lys Glu Gly Xaa Xaa Gly Asp Xaa Gly Leu Xaa Gly Lys Asp Gly Asp
            100                 105                 110

His Gly Lys Xaa Gly Ile Gln Gly Gln Xaa Gly Xaa Xaa Gly Ile Cys
        115                 120                 125

Asp Xaa Ser Leu Cys Phe Ser Val Ile Ala Arg Arg Asp Xaa Phe Arg
    130                 135                 140

Lys Gly Xaa Asn Tyr Ser
145                 150


<210> SEQ ID NO 8
<211> LENGTH: 450
<212> TYPE: DNA
<213> ORGANISM: Homo sapiens

<400> SEQUENCE: 8

ggcggccgcg agcccaaatc ttgtgacaaa actcacacat gcccaccgtg cccaagatct      60

attcctgggc cacctggtcc gataggccca gagggtccca gaggattacc tggtttgcca     120

ggaagagatg gtgttcctgg attagtgggt gtccctggac gtccaggtgt cagaggatta     180

aaaggcctac caggaagaaa tggggaaaaa gggagccaag ggtttgggta tcctggagaa     240
```

```
caaggtcctc ctggtccccc aggtccagag ggccctcctg gaataagcaa agaaggtcct    300

ccaggagacc caggtctccc tggcaaagat ggagaccatg gaaaacctgg aatccaaggg    360

caaccaggcc ccccaggcat ctgcgaccca tcactatgtt ttagtgtaat tgccagaaga    420

gatccgttca gaaaaggacc aaactatagt                                     450


<210> SEQ ID NO 9
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ile Val Leu Thr Gln Ser Pro Pro Ile Met Ser Ala Ser Pro Gly
1               5                   10                  15

Glu Lys Val Thr Met Thr Cys Ser Ala Ser Ser Ser Val Ser Phe Met
            20                  25                  30

Tyr Trp Tyr Gln Gln Lys Pro Gly Ser Ser Pro Arg Leu Leu Ile Tyr
        35                  40                  45

Asp Ala Ser Ile Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Val Ala Thr Tyr Tyr Cys Gln Gln Trp Ser Asp Tyr Ser Pro Arg
                85                  90                  95

Thr Phe Gly Gly Gly Thr Lys Leu Glu Ile Gly Gly Gly Gly Ser Gly
            100                 105                 110

Gly Gly Gly Ser Gly Gly Gly Gly Ser Val Lys Leu Gln Glu Ser Gly
        115                 120                 125

Gly Gly Trp Val Gln Pro Gly Gly Ser Met Lys Leu Ser Cys Ile Ala
    130                 135                 140

Ser Gly Phe Thr Phe Ser Asn Tyr Trp Met Asn Trp Val Arg Gln Ser
145                 150                 155                 160

Pro Glu Lys Gly Leu Glu Trp Val Ala Glu Val Arg Leu Gln Ser Asp
                165                 170                 175

Asn Phe Thr Thr His Tyr Ala Glu Ser Val Lys Gly Arg Phe Thr Ile
            180                 185                 190

Ser Arg Asp Asp Ser Lys Ser Gly Val Tyr Leu Gln Met Asn Asn Leu
        195                 200                 205

Gly Ala Glu Asp Thr Gly Ile Tyr Tyr Cys Thr Pro Phe Ala Tyr Trp
    210                 215                 220

Gly Gln Gly Thr Thr Val Thr Val Ser Ser
225                 230


<210> SEQ ID NO 10
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

gaaattgtgc tgacccagtc tccaccgatc atgtctgctt ctccagggga gaaggtcacc     60

atgacctgca gtgccagctc aagtgtaagt ttcatgtact ggtaccagca gaagccagga    120
```

```
tcctccccca gactcctgat ttatgacgca tccatcctgg cttctggagt ccctgttcgc    180

ttcagtggca gtgggtctgg gacctcttac tctctcacaa tcagccgaat ggaggctgaa    240

gatgttgcca cttattactg ccaacaatgg agtgattact cacccaggac gttcggtgga    300

ggcaccaagc tggaaattgg gggaggcggt tcaggcggag gtggctctgg cggtggcgga    360

tcggtgaaac tgcaggagtc tggaggaggc tgggtgcaac ctggaggatc catgaaactc    420

tcctgtattg cctctggatt cactttcagt aactactgga tgaactgggt ccgccagtct    480

ccagagaagg ggcttgagtg ggttgctgaa gttagattgc aatctgataa ttttacaaca    540

cattatgcgg agtctgtgaa agggaggttc accatctcaa gagatgattc caaaagtggt    600

gtctacctgc aaatgaacaa cttaggagct gaagacactg gcatttatta ttgtaccccg    660

tttgcttatt ggggccaagg gaccacggtc accgtctcct ca                       702


<210> SEQ ID NO 11
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Pro Lys Ser Cys Asp Lys Thr His Thr Cys Pro Pro Cys Pro Arg
1               5                   10                  15

Ser Ile Pro Gly Pro Pro Gly Pro Pro Gly Pro Pro Gly Pro Pro Gly
            20                  25                  30

Pro Pro Gly Pro Pro Gly Pro Pro Gly Pro Pro Gly Pro Pro Gly Pro
        35                  40                  45

Pro Gly Ile Cys Asp Pro Ser Leu Cys Phe Ser Val Ile Ala Arg Arg
    50                  55                  60

Asp Pro Phe Arg Lys Gly Pro Asn Tyr
65                  70


<210> SEQ ID NO 12
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

gagcccaaat cttgtgacaa aactcacaca tgcccaccgt gcccaagatc tattcctggg     60

ccacctggtc ccccaggtcc tccaggaccc ccagggcccc caggcccccc cgggccgcct    120

ggacccccag ggccaccagg ccccccaggc atctgcgacc catcactatg ttttagtgta    180

attgccagaa gagatccgtt cagaaaagga ccaaactat                           219


<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pro or Hyp
<220> FEATURE:
<221> NAME/KEY: MOD_RES
```

<222> LOCATION: (5)..(6)
<223> OTHER INFORMATION: Pro or Hyp
<220> FEATURE:
<221> NAME/KEY: MOD_RES
<222> LOCATION: (8)..(9)
<223> OTHER INFORMATION: Pro or Hyp
<220> FEATURE:
<221> NAME/KEY: MOD_RES
<222> LOCATION: (11)..(12)
<223> OTHER INFORMATION: Pro or Hyp
<220> FEATURE:
<221> NAME/KEY: MOD_RES
<222> LOCATION: (14)..(15)
<223> OTHER INFORMATION: Pro or Hyp
<220> FEATURE:
<221> NAME/KEY: MOD_RES
<222> LOCATION: (17)..(18)
<223> OTHER INFORMATION: Pro or Hyp
<220> FEATURE:
<221> NAME/KEY: MOD_RES
<222> LOCATION: (20)..(21)
<223> OTHER INFORMATION: Pro or Hyp
<220> FEATURE:
<221> NAME/KEY: MOD_RES
<222> LOCATION: (23)..(24)
<223> OTHER INFORMATION: Pro or Hyp
<220> FEATURE:
<221> NAME/KEY: MOD_RES
<222> LOCATION: (26)..(27)
<223> OTHER INFORMATION: Pro or Hyp
<220> FEATURE:
<221> NAME/KEY: MOD_RES
<222> LOCATION: (29)..(30)
<223> OTHER INFORMATION: Pro or Hyp
<220> FEATURE:
<221> NAME/KEY: MOD_RES
<222> LOCATION: (32)..(33)
<223> OTHER INFORMATION: Pro or Hyp
<220> FEATURE:
<221> NAME/KEY: MOD_RES
<222> LOCATION: (35)..(35)
<223> OTHER INFORMATION: Pro or Hyp

<400> SEQUENCE: 13

```
Gly Ser Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Ser Ser Gly Gly
        35
```

<210> SEQ ID NO 14
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
ggcagccctg ggccacctgg tcccccaggt cctccaggac ccccagggcc cccaggcccc     60

cccgggccgc ctggaccccc agggccacca ggccccccag gcccttcctc tggcgga       117
```

<210> SEQ ID NO 15
<211> LENGTH: 48
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES

```
<222> LOCATION: (3)..(4)
<223> OTHER INFORMATION: Pro or Hyp
<220> FEATURE:
<221> NAME/KEY: MOD_RES
<222> LOCATION: (6)..(6)
<223> OTHER INFORMATION: Pro or Hyp
<220> FEATURE:
<221> NAME/KEY: MOD_RES
<222> LOCATION: (10)..(10)
<223> OTHER INFORMATION: Pro or Hyp
<220> FEATURE:
<221> NAME/KEY: MOD_RES
<222> LOCATION: (12)..(13)
<223> OTHER INFORMATION: Pro or Hyp
<220> FEATURE:
<221> NAME/KEY: MOD_RES
<222> LOCATION: (15)..(16)
<223> OTHER INFORMATION: Pro or Hyp
<220> FEATURE:
<221> NAME/KEY: MOD_RES
<222> LOCATION: (18)..(19)
<223> OTHER INFORMATION: Pro or Hyp
<220> FEATURE:
<221> NAME/KEY: MOD_RES
<222> LOCATION: (21)..(22)
<223> OTHER INFORMATION: Pro or Hyp
<220> FEATURE:
<221> NAME/KEY: MOD_RES
<222> LOCATION: (24)..(25)
<223> OTHER INFORMATION: Pro or Hyp
<220> FEATURE:
<221> NAME/KEY: MOD_RES
<222> LOCATION: (27)..(28)
<223> OTHER INFORMATION: Pro or Hyp
<220> FEATURE:
<221> NAME/KEY: MOD_RES
<222> LOCATION: (30)..(31)
<223> OTHER INFORMATION: Pro or Hyp
<220> FEATURE:
<221> NAME/KEY: MOD_RES
<222> LOCATION: (33)..(34)
<223> OTHER INFORMATION: Pro or Hyp
<220> FEATURE:
<221> NAME/KEY: MOD_RES
<222> LOCATION: (36)..(37)
<223> OTHER INFORMATION: Pro or Hyp
<220> FEATURE:
<221> NAME/KEY: MOD_RES
<222> LOCATION: (39)..(40)
<223> OTHER INFORMATION: Pro or Hyp
<220> FEATURE:
<221> NAME/KEY: MOD_RES
<222> LOCATION: (45)..(45)
<223> OTHER INFORMATION: Pro or Hyp

<400> SEQUENCE: 15

Thr Cys Xaa Xaa Cys Xaa Arg Ser Ile Xaa Gly Xaa Xaa Gly Xaa Xaa
1               5                   10                  15

Gly Xaa Xaa Gly Xaa Xaa Gly Xaa Xaa Gly Xaa Xaa Gly Xaa Xaa Gly
            20                  25                  30

Xaa Xaa Gly Xaa Xaa Gly Xaa Xaa Gly Ile Cys Asp Xaa Ser Leu Cys
        35                  40                  45


<210> SEQ ID NO 16
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

acatgcccac cgtgcccaag atctattcct gggccacctg gtcccccagg tcctccagga     60
```

cccccagggc ccccaggccc ccccgggccg cctggacccc cagggccacc aggcccccca 120
ggcatctgcg acccatcact atgt 144

<210> SEQ ID NO 17
<211> LENGTH: 66
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Pro or Hyp
<220> FEATURE:
<221> NAME/KEY: MOD_RES
<222> LOCATION: (12)..(13)
<223> OTHER INFORMATION: Pro or Hyp
<220> FEATURE:
<221> NAME/KEY: MOD_RES
<222> LOCATION: (15)..(15)
<223> OTHER INFORMATION: Pro or Hyp
<220> FEATURE:
<221> NAME/KEY: MOD_RES
<222> LOCATION: (19)..(19)
<223> OTHER INFORMATION: Pro or Hyp
<220> FEATURE:
<221> NAME/KEY: MOD_RES
<222> LOCATION: (21)..(22)
<223> OTHER INFORMATION: Pro or Hyp
<220> FEATURE:
<221> NAME/KEY: MOD_RES
<222> LOCATION: (24)..(25)
<223> OTHER INFORMATION: Pro or Hyp
<220> FEATURE:
<221> NAME/KEY: MOD_RES
<222> LOCATION: (27)..(28)
<223> OTHER INFORMATION: Pro or Hyp
<220> FEATURE:
<221> NAME/KEY: MOD_RES
<222> LOCATION: (30)..(31)
<223> OTHER INFORMATION: Pro or Hyp
<220> FEATURE:
<221> NAME/KEY: MOD_RES
<222> LOCATION: (33)..(34)
<223> OTHER INFORMATION: Pro or Hyp
<220> FEATURE:
<221> NAME/KEY: MOD_RES
<222> LOCATION: (37)..(37)
<223> OTHER INFORMATION: Pro or Hyp
<220> FEATURE:
<221> NAME/KEY: MOD_RES
<222> LOCATION: (40)..(40)
<223> OTHER INFORMATION: Pro or Hyp
<220> FEATURE:
<221> NAME/KEY: MOD_RES
<222> LOCATION: (42)..(43)
<223> OTHER INFORMATION: Pro or Hyp
<220> FEATURE:
<221> NAME/KEY: MOD_RES
<222> LOCATION: (45)..(46)
<223> OTHER INFORMATION: Pro or Hyp
<220> FEATURE:
<221> NAME/KEY: MOD_RES
<222> LOCATION: (48)..(49)
<223> OTHER INFORMATION: Pro or Hyp
<220> FEATURE:
<221> NAME/KEY: MOD_RES
<222> LOCATION: (51)..(52)
<223> OTHER INFORMATION: Pro or Hyp
<220> FEATURE:
<221> NAME/KEY: MOD_RES
<222> LOCATION: (54)..(55)
<223> OTHER INFORMATION: Pro or Hyp
<220> FEATURE:
<221> NAME/KEY: MOD_RES
<222> LOCATION: (57)..(58)

```
<223> OTHER INFORMATION: Pro or Hyp
<220> FEATURE:
<221> NAME/KEY: MOD_RES
<222> LOCATION: (63)..(63)
<223> OTHER INFORMATION: Pro or Hyp

<400> SEQUENCE: 17

Glu Xaa Lys Ser Gly Asp Lys Thr His Thr Cys Xaa Xaa Cys Xaa Arg
1               5                   10                  15

Ser Ile Xaa Gly Xaa Xaa Gly Xaa Xaa Gly Xaa Xaa Gly Xaa Xaa Gly
            20                  25                  30

Xaa Xaa Gly Lys Xaa Gly Lys Xaa Gly Xaa Xaa Gly Xaa Xaa Gly Xaa
        35                  40                  45

Xaa Gly Xaa Xaa Gly Xaa Xaa Gly Xaa Xaa Gly Ile Cys Asp Xaa Ser
    50                  55                  60

Leu Cys
65


<210> SEQ ID NO 18
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

gagcccaaat ctggtgacaa aactcacaca tgcccaccgt gcccaagatc tattcctggg     60

ccacctggtc ccccaggtcc tccaggaccc ccagggcccc caggtaaacc tggaaaacca    120

gggcccccag gcccccccgg gccgcctgga cccccagggc caccaggccc cccaggcatc    180

tgcgacccat cactatgt                                                  198


<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (12)..(12)
<223> OTHER INFORMATION: Hyp
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
```

```
<221> NAME/KEY: MOD_RES
<222> LOCATION: (24)..(24)
<223> OTHER INFORMATION: Hyp
<220> FEATURE:
<221> NAME/KEY: MOD_RES
<222> LOCATION: (27)..(27)
<223> OTHER INFORMATION: Hyp
<220> FEATURE:
<221> NAME/KEY: MOD_RES
<222> LOCATION: (30)..(30)
<223> OTHER INFORMATION: Hyp

<400> SEQUENCE: 19

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa
            20                  25                  30


<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro
            20                  25                  30


<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pro or Hyp
<220> FEATURE:
<221> NAME/KEY: MOD_RES
<222> LOCATION: (6)..(6)
<223> OTHER INFORMATION: Pro or Hyp
<220> FEATURE:
<221> NAME/KEY: MOD_RES
<222> LOCATION: (9)..(9)
<223> OTHER INFORMATION: Pro or Hyp
<220> FEATURE:
<221> NAME/KEY: MOD_RES
<222> LOCATION: (12)..(12)
<223> OTHER INFORMATION: Pro or Hyp
<220> FEATURE:
<221> NAME/KEY: MOD_RES
<222> LOCATION: (15)..(15)
<223> OTHER INFORMATION: Pro or Hyp
<220> FEATURE:
<221> NAME/KEY: MOD_RES
<222> LOCATION: (18)..(18)
<223> OTHER INFORMATION: Pro or Hyp
<220> FEATURE:
<221> NAME/KEY: MOD_RES
<222> LOCATION: (21)..(21)
<223> OTHER INFORMATION: Pro or Hyp
<220> FEATURE:
<221> NAME/KEY: MOD_RES
<222> LOCATION: (24)..(24)
<223> OTHER INFORMATION: Pro or Hyp
<220> FEATURE:
<221> NAME/KEY: MOD_RES
```

<222> LOCATION: (27)..(27)
<223> OTHER INFORMATION: Pro or Hyp
<220> FEATURE:
<221> NAME/KEY: MOD_RES
<222> LOCATION: (30)..(30)
<223> OTHER INFORMATION: Pro or Hyp

<400> SEQUENCE: 21

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa
            20                  25                  30

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Pro or Hyp
<220> FEATURE:
<221> NAME/KEY: MOD_RES
<222> LOCATION: (6)..(6)
<223> OTHER INFORMATION: Pro or Hyp
<220> FEATURE:
<221> NAME/KEY: MOD_RES
<222> LOCATION: (9)..(9)
<223> OTHER INFORMATION: Pro or Hyp
<220> FEATURE:
<221> NAME/KEY: MOD_RES
<222> LOCATION: (12)..(12)
<223> OTHER INFORMATION: Pro or Hyp
<220> FEATURE:
<221> NAME/KEY: MOD_RES
<222> LOCATION: (15)..(15)
<223> OTHER INFORMATION: Pro or Hyp
<220> FEATURE:
<221> NAME/KEY: MOD_RES
<222> LOCATION: (24)..(24)
<223> OTHER INFORMATION: Pro or Hyp
<220> FEATURE:
<221> NAME/KEY: MOD_RES
<222> LOCATION: (27)..(27)
<223> OTHER INFORMATION: Pro or Hyp
<220> FEATURE:
<221> NAME/KEY: MOD_RES
<222> LOCATION: (30)..(30)
<223> OTHER INFORMATION: Pro or Hyp
<220> FEATURE:
<221> NAME/KEY: MOD_RES
<222> LOCATION: (33)..(33)
<223> OTHER INFORMATION: Pro or Hyp
<220> FEATURE:
<221> NAME/KEY: MOD_RES
<222> LOCATION: (36)..(36)
<223> OTHER INFORMATION: Pro or Hyp
<220> FEATURE:
<221> NAME/KEY: MOD_RES
<222> LOCATION: (39)..(39)
<223> OTHER INFORMATION: Pro or Hyp

<400> SEQUENCE: 22

Gly Pro Xaa Gly Pro Xaa Gly Pro Xaa Gly Pro Xaa Gly Pro Xaa Gly
1               5                   10                  15

Lys Pro Gly Lys Pro Gly Pro Xaa Gly Pro Xaa Gly Pro Xaa Gly Pro
            20                  25                  30

Xaa Gly Pro Xaa Gly Pro Xaa
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gly Ser Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
            20                  25                  30

Pro Gly Pro Ser
        35
```

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Thr Cys Pro Pro Cys Pro Arg Ser Ile Pro
1               5                   10
```

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gly Ile Cys Asp Pro Ser Leu Cys
1               5
```

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Gly Pro Pro Gly Pro Pro Gly Pro Pro Gly Pro Pro Gly Pro Pro Gly
1               5                   10                  15

Lys Pro Gly Lys Pro Gly Pro Pro Gly Pro Pro Gly Pro Pro Gly Pro
            20                  25                  30

Pro Gly Pro Pro Gly Pro Pro
        35
```

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)

```
<223> OTHER INFORMATION: Hyp
<220> FEATURE:
<221> NAME/KEY: MOD_RES
<222> LOCATION: (6)..(6)
<223> OTHER INFORMATION: Hyp
<220> FEATURE:
<221> NAME/KEY: MOD_RES
<222> LOCATION: (9)..(9)
<223> OTHER INFORMATION: Hyp
<220> FEATURE:
<221> NAME/KEY: MOD_RES
<222> LOCATION: (11)..(12)
<223> OTHER INFORMATION: Variable amino acid
<220> FEATURE:
<221> NAME/KEY: MOD_RES
<222> LOCATION: (15)..(15)
<223> OTHER INFORMATION: Hyp
<220> FEATURE:
<221> NAME/KEY: MOD_RES
<222> LOCATION: (18)..(18)
<223> OTHER INFORMATION: Hyp
<220> FEATURE:
<221> NAME/KEY: MOD_RES
<222> LOCATION: (21)..(21)
<223> OTHER INFORMATION: Hyp
<220> FEATURE:
<221> NAME/KEY: MOD_RES
<222> LOCATION: (24)..(24)
<223> OTHER INFORMATION: Hyp
<220> FEATURE:
<223> OTHER INFORMATION: See specification as filed for detailed
      description of substitutions and preferred embodiments

<400> SEQUENCE: 27

Gly Pro Xaa Gly Pro Xaa Gly Pro Xaa Gly Xaa Xaa Gly Pro Xaa Gly
1               5                   10                  15

Pro Xaa Gly Pro Xaa Gly Pro Xaa
            20


<210> SEQ ID NO 28
<211> LENGTH: 19
<212> TYPE: PRT
<213> ORGANISM: Homo sapiens

<400> SEQUENCE: 28

Glu Pro Lys Ser Cys Asp Lys Thr His Thr Cys Pro Pro Cys Pro Arg
1               5                   10                  15

Ser Ile Pro


<210> SEQ ID NO 29
<211> LENGTH: 27
<212> TYPE: PRT
<213> ORGANISM: Bateriophage T4

<400> SEQUENCE: 29

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25


<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

```
Gly Gly Gly Gly Ser Gly Gly Gly Gly Ser Gly Gly Gly Gly Ser
1               5                   10                  15


<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Ser Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro Gly Pro
            20                  25                  30

Pro Gly Pro Ser Ser Gly Gly
        35


<210> SEQ ID NO 32
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Thr Cys Pro Pro Cys Pro Arg Ser Ile Pro Gly Pro Pro Gly Pro Pro
1               5                   10                  15

Gly Pro Pro Gly Pro Pro Gly Pro Pro Gly Pro Pro Gly Pro Pro Gly
            20                  25                  30

Pro Pro Gly Pro Pro Gly Pro Pro Gly Ile Cys Asp Pro Ser Leu Cys
        35                  40                  45


<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)..(12)
<223> OTHER INFORMATION: Variable amino acid
<220> FEATURE:
<221> NAME/KEY: MOD_RES
<222> LOCATION: (14)..(15)
<223> OTHER INFORMATION: Variable amino acid

<400> SEQUENCE: 33

Gly Xaa Xaa Gly Xaa Xaa Gly Xaa Xaa Gly Xaa Xaa Gly Xaa Xaa
1               5                   10                  15
```